United States Patent
Rozhanskii et al.

(10) Patent No.: US 7,163,988 B2
(45) Date of Patent: Jan. 16, 2007

(54) AROMATIC SULFONIC ACID ESTER DERIVATIVE, POLYARYLENE, POLYARYLENE HAVING SULFONIC ACID GROUP AND PROCESS FOR PRODUCING THE SAME, AND POLYMER SOLID ELECTROLYTE AND PROTON-CONDUCTIVE MEMBRANE

(75) Inventors: Igor Rozhanskii, Tokyo (JP); Masayuki Takahashi, Tokyo (JP); Kohei Goto, Tokyo (JP); Yousuke Konno, Tokyo (JP); Toshihiro Ohtsuki, Tokyo (JP); Yoshitaka Yamakawa, Tokyo (JP); Toshiaki Kadota, Tokyo (JP)

(73) Assignee: JSR Corporation, Tokyo (JP)

( * ) Notice: Subject to any disclaimer, the term of this patent is extended or adjusted under 35 U.S.C. 154(b) by 455 days.

(21) Appl. No.: 10/642,694

(22) Filed: Aug. 19, 2003

(65) Prior Publication Data
US 2004/0044166 A1 Mar. 4, 2004

(30) Foreign Application Priority Data

Aug. 22, 2002 (JP) .............................. 2002-242508
Dec. 16, 2002 (JP) .............................. 2002-364229

(51) Int. Cl.
*C08F 283/08* (2006.01)
*C08G 61/10* (2006.01)

(52) U.S. Cl. .................... 525/535; 525/332.4; 525/288; 525/291; 528/86; 528/171; 528/255; 528/219; 528/373

(58) Field of Classification Search ............. 525/332.4, 525/288, 291, 535; 528/86, 171, 205, 219, 528/391, 373
See application file for complete search history.

(56) References Cited

U.S. PATENT DOCUMENTS

2002/0164513 A1  11/2002  Asano et al.

FOREIGN PATENT DOCUMENTS

| DE | 102 01 886 | 8/2002 |
| EP | 0 041 780 | 12/1981 |
| EP | 1 138 712 | 10/2001 |
| EP | 1 245 554 | 10/2002 |

*Primary Examiner*—Duc Truong
(74) *Attorney, Agent, or Firm*—Oblon, Spivak, McClelland, Maier & Neustadt, P.C.

(57) ABSTRACT

Disclosed is an aromatic sulfonic acid ester derivative represented by the formula (1);

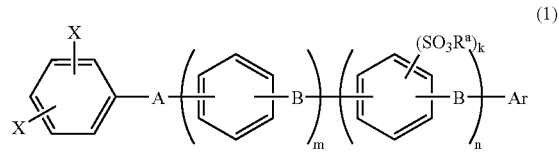

in the formula, X is an atom or a group selected from a halogen atom excluding fluorine, $-OSO_3CH_3$ and $-OSO_3CF_3$, A is a divalent electron attractive group, B is a divalent electron donating group or a direct bonding, $R^a$ is a hydrocarbon group of 1 to 20 carbon atoms, Ar is an aromatic group having a substituent of $-SO_3R^b$ (wherein $R^b$ is a hydrocarbon group of 1 to 20 carbon atoms), m is an integer of 0 to 10, n is an integer of 0 to 10 and k is an integer of 1 to 4. Also disclosed is a process for producing a polyarylene having a sulfonic acid group, which process comprises the steps of coupling polymerization of an aromatic compound containing the derivative of the formula (1), to prepare a polyarylene and hydrolysis of the polyarylene, and which process has high safety and is easily capable of controlling the amount of sulfonoc acid group introduced into a polymer and the introducing position thereof.

9 Claims, 32 Drawing Sheets

AROMATIC SULFONIC ACID ESTER DERIVATIVE, POLYARYLENE, POLYARYLENE HAVING SULFONIC ACID GROUP AND PROCESS FOR PRODUCING THE SAME, AND POLYMER SOLID ELECTROLYTE AND PROTON-CONDUCTIVE MEMBRANE

FIELD OF THE INVENTION

The present invention relates to a novel aromatic sulfonic acid ester derivative, a polyarylene containing a repeating structural unit derived from the derivative, a polyarylene having s sulfonic acid group prepared by hydrolyzing the polyarylene and a process for producing the same, and further relates to a polymer solid electrolyte comprising the sulfonic group-containing polyarylene and a proton conductive membrane containing the polymer solid electrolyte.

BACKGROUND OF THE INVENTION

Electrolytes are frequently used in an (aqueous) solution state. However, the aqueous solution state is recently replaced with a solid state because the solid state has easy processing characteristics in the case of applying it to electric and electronic materials and there are recent tendencies of lightweight, thin, short and small size, and saving electric power.

Conventionally, both of inorganic compounds and organic compounds are known as a proton conductive material. An example of the inorganic compounds is uranyl phosphate, which is a hydrate. These inorganic compounds have insufficient contact in the interface and have many problems in forming a conductive membrane on a substrate or electrode.

On the other hand, examples of the organic compounds are polymers belonging to cation exchange resins, for example, sulfonated vinyl polymers such as polystyrene sulfonic acid, perfluoroalkyl sulfonic acid polymer represented by Nafion (Trade name, Du Pont Co., Ltd.), perfluoroalkyl carboxylic acid polymer, and polymers prepared by introducing a sulfonic acid group or phosphoric acid group into a heat resistant polymer such as polybenzimidazole or polyether ether ketone (Polymer Preprints, Japan, Vol. 42, No. 7, pp. 2490–2492 (1993), Polymer Preprints, Japan, Vol. 43, No. 3, pp. 735–736 (1994), Polymer Preprints, Japan, Vol. 42, No. 3, p. 730(1993)).

Sulfonated vinyl polymers such as polystyrene sulfonic acid, etc, however, have a problem of inferior chemical stability (durability). A perfluorosulfonic acid electrolyte membrane is difficult to be produced and very expensive. On this account, it has difficulties in application for general use, such as automobile and household fuel cells, etc and is applicable for specially limited uses. After the use thereof, the perfluorosulfonic acid electrolyte membrane, further, has a great environmental problem in waste treatment because it has a large amount of fluorine atom in its molecules. Polymers prepared by introducing a sulfonic acid group or phosphoric acid into a heat resistant polymer such as polybenzimidazole, polyether ether ketone etc also have a problem of inferior resistance to hot water and durability.

On the other hand, sulfonated aromatic polymers are known as a proton conductive material which is industrially produced in low cost and has excellent resistance to hot water and durability. The sulfonated aromatic polymers are usually prepared by polymerizing an aromatic compound to prepare a polymer and then allowing the polymer to react with a sulfonating agent to introduce a sulfonic acid group into the polymer.

However, conventional methods have many problems such that the production risk is high because of using a large amount of the sulfonating agent such as concentrated sulfuric acid, fuming sulfuric acid, chlorosulfuric acid etc in introducing sulfonic acid, and further plant materials have limitation and the load of waste fluid treatment is high in recovering the polymer. The conventional methods, further, have problems of no facility of controlling the amount and the introducing position of the sulfonic acid group introduced into the polymer.

OBJECT OF THE INVENTION

The present invention is intended to solve the problems associated with the prior art as mentioned above, it is an object of the present invention to provide a proton conductive material having excellent resistance to hot water and durability which is industrially produced in low cost.

Another object of the present invention is to provide a process for producing a polyarylene having a sulfonic acid group which process can produce a polyarylene having a sulfonic acid without using a large amount of a sulfonating agent, and has a low load of treatment in recovering a polymer and facility in controlling the amount of the sulfonic acid group introduced into the polymer and the introducing position.

A further object of the present invention is to provide a polyarylene having a sulfonic acid group obtainable by the process.

A furthermore object of the present invention is to provide a novel aromatic sulfonic acid ester derivative suitable for use in production of the polyarylene having a sulfonic acid group and to provide a polyarylene.

A still further object of the present invention is to provide a polymer solid electrolyte comprising the polyarylene having a sulfonic acid group and a proton-conductive membrane comprising the polymer solid electrolyte.

SUMMARY OF THE INVENTION

The present invention provides the following novel aromatic sulfonic acid ester derivative, polyarylene, polyarylene having a sulfonic acid group and production process thereof, and further provides the polymer solid electrolyte, proton-conductive membrane and the production process thereof. Thus, the above objects of the present invention can be attained.

In the present invention, polyarylene shows a polymer obtainable by using, as a starting material, a dihalide compound having an aromatic ring or an aromatic compound having two groups represented by —OSO$_3$R (R is CH$_3$, CF$_3$ etc), and polymerization with direct bonding of aromatic rings.

(1) The aromatic sulfonic acid ester derivative represented by the formula (1);

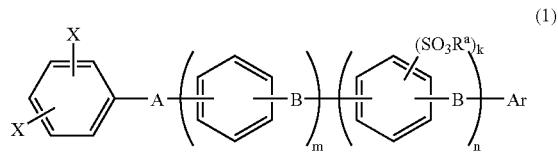

in which X is an atom or a group selected from a halogen atom excluding fluorine, —OSO$_3$CH$_3$ and —OSO$_3$CF$_3$, A is a divalent electron attractive group, B is a divalent electron donating group or a direct bonding, R$^a$ is a hydrocarbon group of 1 to 20 carbon atoms, Ar is an aromatic group having a substituent represented by —SO$_3$R$^b$ wherein R$^b$ is a hydrocarbon group of 1 to 20 carbon atoms, m is an integer of 0 to 10, n is an integer of 0 to 10 and k is an integer of 1 to 4.

(2) The polyarylene comprising repeating structural units derived from an aromatic compound, which contains at least repeating structural units represented by the formula (1');

$$\begin{array}{c}\text{(1')}\end{array}$$

in which A is a divalent electron attractive group, B is a divalent electron donating group or a direct bonding, R$^a$ is a hydrocarbon group of 1 to 20 carbon atoms, Ar is an aromatic group having a substituent represented by —SO$^3$R$^b$ wherein R$^b$ is a hydrocarbon group of 1 to 20 carbon atoms, m is an integer of 0 to 10, n is an integer of 0 to 10 and k is an integer of 1 to 4.

(3) The polyarylene comprising 0.5 to 100% by mole of repeating structural units represented by the formula (1') and 0 to 99.5% by mole of repeating structural units represented by the following formula (A');

$$\begin{array}{c}\text{(A')}\end{array}$$

in which R$^1$ to R$^8$ is identically or differently at least one atom or group selected from hydrogen, fluorine atom, alkyl group, fluorine substituted alkyl group, allyl group and aryl group, W is a divalent electron attractive group, T is a divalent organic group and p is 0 or a positive integer.

(4) The process for producing a polyarylene having a sulfonic acid group which process comprises the steps of coupling polymerizing an aromatic compound containing an aromatic sulfonic acid ester derivative represented by the formula (1) to prepare a polyarylene, and hydrolyzing the resulting polyarylene.

(5) The polymer solid electrolyte which comprises the polyarylene having a sulfonic acid group prepared by the process (4).

(6) The proton-conductive membrane containing the polymer solid electrolyte.

DETAILED DESCRIPTION OF PREFERRED EMBODIMENT

Figure 1:
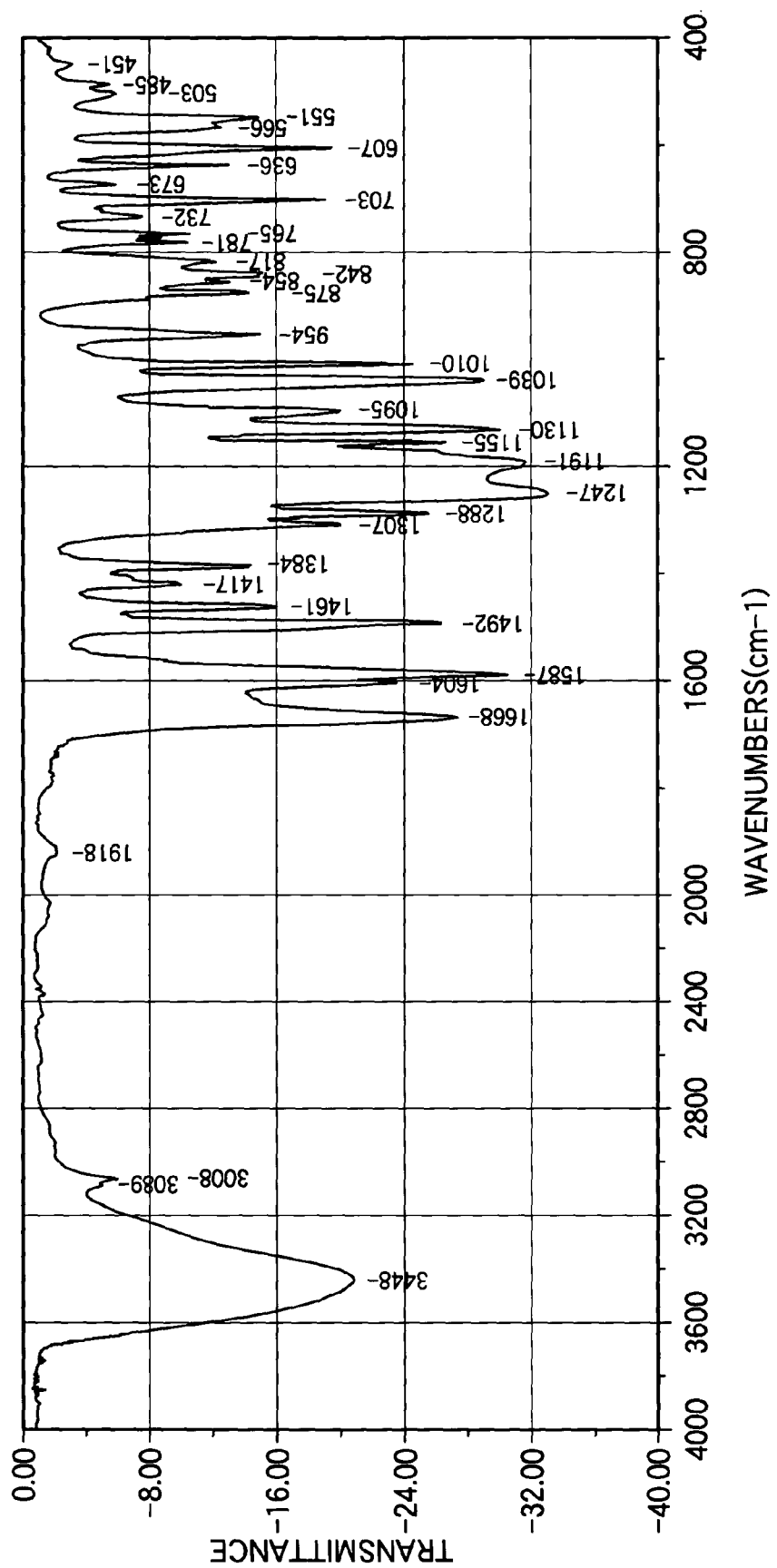
FIG. 1 is an IR spectrum of a white powder prepared in Example 1 (1).

The aromatic sulfonic acid ester derivative, polyarylene, polyarylene having a sulfonic acid and the production process of the same, and the polymer solid electrolyte and the proton conductive membrane will be described in detail hereinafter.

(Aromatic Sulfonic Acid Ester Derivative)

The aromatic sulfonic acid ester derivative according to the present invention is represented by the formula (1).

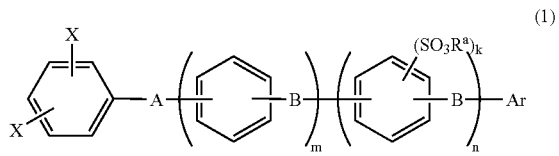
(1)

In the formula, X is an atom or a group selected from a halogen atom excluding fluorine (chlorine, bromine and iodine), —OSO$_3$CH$_3$ and —OSO$_3$CF$_3$.

A is a divalent electron attractive group, and examples thereof are —CO—, —CONH—, —(CF$_2$)$_p$— (herein p is an integer of 1 to 10), —C(CF$_3$)$_2$—, —COO—, —SO— and —SO$_2$—.

B is a divalent electron donating group or a direct bonding, and examples thereof are —O—, —S—, —CH=CH—, —C≡C—,

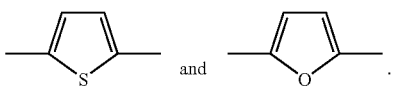

The electron attractive group means a group having a Hammett substituent constant of not less than 0.06 in the case that a phenyl group is at a m-position, and a Hammett substituent constant of not less than 0.01 in the case that a phenyl group is at a p-position.

$R^a$ is a hydrocarbon group of 1 to 20 carbon atoms, preferably a hydrocarbon group of 4 to 20 carbon atoms and examples thereof are linear hydrocarbon groups, branched hydrocarbon groups, alicyclic hydrocarbon groups and hydrocarbon groups having a 5-membered hetero ring, such as methyl, ethyl, n-propyl, iso-propyl, tert-butyl, iso-butyl, n-butyl, sec-butyl, neopentyl, cyclo-pentyl, hexyl, cyclohexyl, cyclopentylmethyl, cyclohexylmethyl, adamantyl, adamantylmethyl, 2-ethylhexyl, bicycle[2,2,1]heptyl, bicycle[2,2,1]heptylmethyl, tetrahydrofurfuryl, 2-methylbutyl, 3,3-dimethyl-2,4-dioxorane methyl, cyclohexylmethyl, adamantylmethyl and bicycle[2,2,1]heptylmethyl groups. Of these, n-butyl, neopentyl, tetrahydrofurfuryl, cyclopenthyl, cyclohexyl, cyclohexylmethyl, adamantylmethyl and bicyclo[2,2,1]heptylmethyl groups are preferred, and further, neopentyl group is more preferred.

Ar is an aromatic group having a substituent represented by —SO$_3$R$^b$, and exemplary aromatic groups include phenyl, naphthyl, anthracenyl and phenanthyl groups. Of these groups, phenyl and naphthyl groups are preferred.

With regard to the substituent —SO$_3$R$^b$, the aromatic group has one or two or more substituents, and when it has two or more substituents —SO$_3$R$^b$, these substituents may be the same or different each other.

$R^b$ is a hydrocarbon group of 1 to 20 carbon atoms, preferably 4 to 20 carbon atoms, and examples thereof are the hydrocarbon groups of 1 to 20 carbon atoms as described above. Of these, n-butyl, neopentyl, tetra-hydrofurfuryl, cyclopentyl, cyclohexyl, cyclohexylmethyl, adamantylm- ethyl, bicycle[2,2,1]heptylmethyl groups are preferred, and further neopentyl group is more preferred.

m is an integer of 0 to 10, preferably 0 to 2, n is an integer of 0 to 10, preferably 0 to 2 and k is an integer of 1 to 4.

More specific examples of the aromatic sulfonic acid ester derivative of the formula (1) according to the present invention include the following compounds of the types (a) to (c).

Compound of Type (a)

The compound of type (a) is a compound represented by the following formula (1-a).

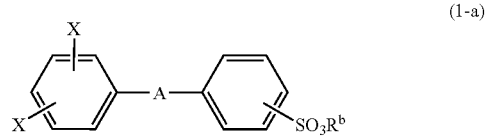
(1-a)

In the formula (1-a), X, A and R$^b$ have the same meanings as those in the formula (1).

In the aromatic sulfonic acid ester derivative of the formula (1-a), A is preferably —CO— or —SO$_2$—. R$^b$ is preferably neopentyl, tetrahydrofurfuryl, cyclopentylmethyl, cyclohexylmethyl, adamantylmethyl or bicycle[2,2,1]heptylmethyl group, and further, more preferably neopentyl group.

Examples of the aromatic sulfonic acid ester derivative of the formula (1-a) are as follows:

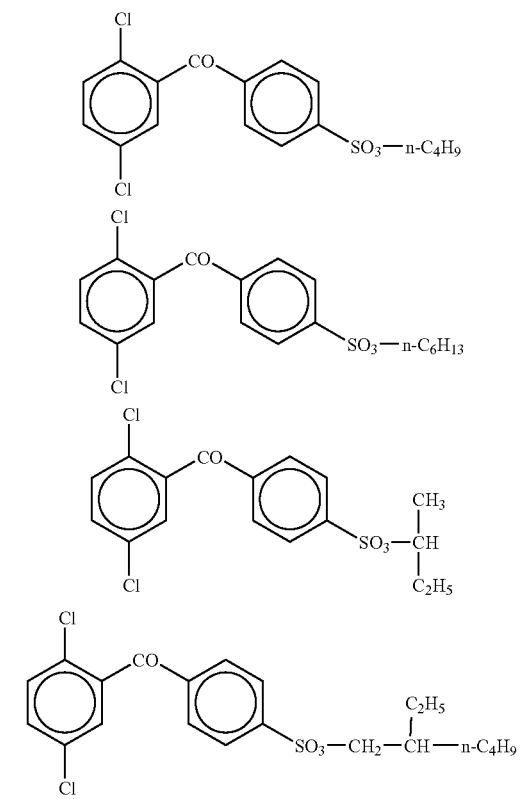

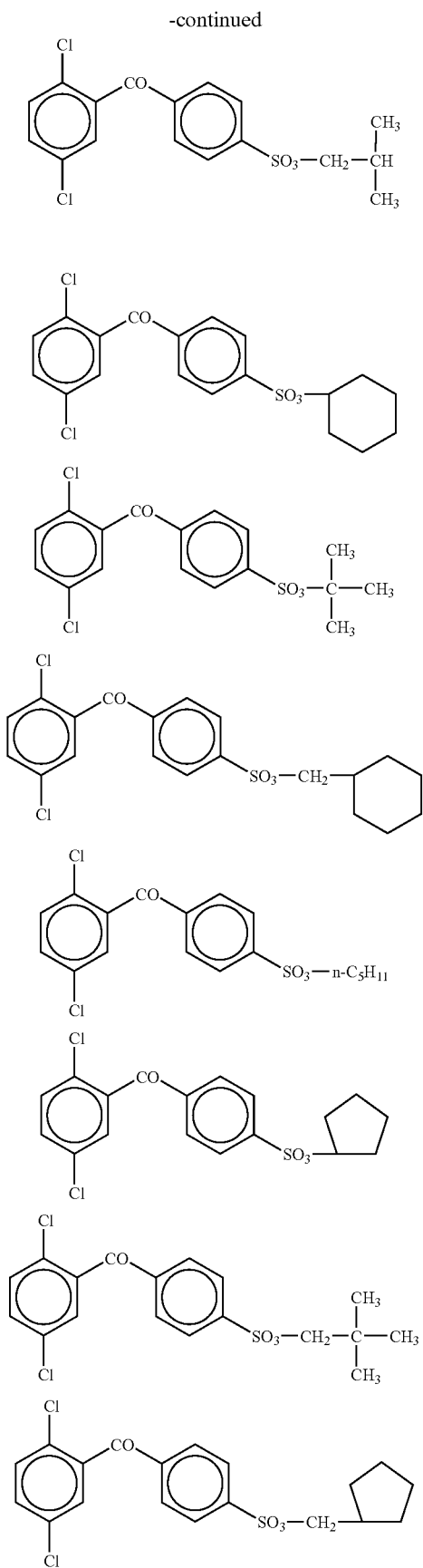
Further examples of the aromatic sulfonic acid ester derivative of the formula (1-a) include compounds obtainable by replacing chlorine atom with bromine atom or iodine atom in the above compounds, compounds obtainable by replacing —CO— with —SO$_2$— in the above compounds and compounds obtainable by replacing chlorine atom with bromine atom or iodine atom and —CO— with —SO$_2$— in the above compounds.

The R$^b$ group in the formula (1-a) is derived from primary alcohol. β carbon is preferably tertiary or quaternary carbon because it has excellent stability in polymerization steps and does not inhibit the polymerization nor induce cross-linking due to generation of sulfonic acid caused by de-esterification. Further, it is preferred that these ester groups be derived from primary alcohol and the β position be quaternary carbon.

Process for synthesizing the compound of type (a)

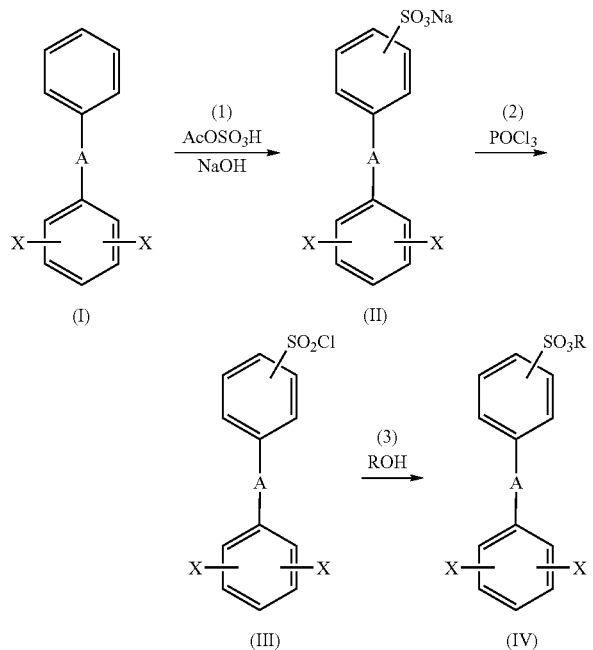

Step (1) Sulfonation of Compound (I) (for Example, a Method of Using Acetyl Sulfuric Acid and Sodium Hydroxide):

For example, a 1,2-dichloromethane as compound (I) solution of 2,5-dichlorobenzophenone is allowed to react with 5 mol times of a 1,2-dichloromethane solution of acetyl sulfate at 60° C. for 3 to 5 hr. After reacting, the reaction is finished with 1-propanol and poured into 3 mol times of a NaOH aqueous solution. The resulting solution is concentrated to obtain fine powdery 2,5-dichlorobenzophenone-3'-sodium sulfonate.

Step (2) Chlorination of Compound (II) (for Example a Method of Using Phosphoryl Chloride):

For example, the 2,5-dichlorobenzophenone-3'-sodium sulfonate as compound (II) is dissolved in about 3 to 4 times(weight/volume), based on the 2,5-dichlorobenzophenone-3'-sodium sulfonate, of a solvent (mixed solvent, sulfolane/acetylnitrile=4/6 (volume ratio), heated to 70° C. and allowed to react with phosphoryl chloride at about 10° C. for about 5 hr. After the reaction, the reactant is diluted with a large excess of cold water to precipitate a product. After filtration, the product is re-crystallized with toluene to obtain a purified crystal 2,5-dichlorobenzophenone-3'-sulfonic acid chloride.

When 5 to 10 mol times of chlorosulfonic acid is used in place of acetyl sulfuric acid used in the step (1), conversion to sulfonated chloride can be conducted at once.

Step (3) Esterification of Compound (III) (for Example, a Method of Using i-Butylalcohol):

For example, the 2,5-dichlorobenzophenone-3'-sulfonic acid chloride as compound (III) is added dropwise to equivalent amount or more (usually 1 to 3 mol times), based on the 2,5-dichlorobenzophenone-3'-sulfonic acid chloride, of a cooled mixed solution of i-butylalcohol and pyridine to perform reaction. The reaction is performed at up to 20° C. The reaction time, depending to the reaction scale, is about from 10 min to 5 hr. The reaction mixed solution is treated with dilute hydrochloric acid and washed with water and then an aimed product is extracted with ethyl acetate. The extract is concentrated and separated, and then re-crystallized with methanol to obtain an aromatic sulfonic acid ester derivative (compound IV).

Compound of Type (b)

The compound of type (b) is a compound represented by the following formula (1-b).

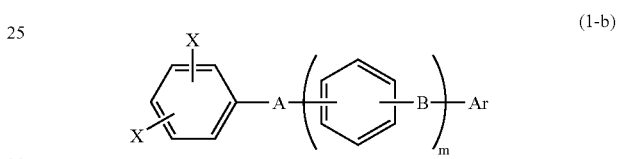

In the formula (1-b), X, A, B, Ar and m have the same meanings as those in the formula (1).

In the aromatic sulfonic acid ester derivative of the formula (1-b), B is preferably a divalent electron donating group, the Ar aromatic group having a substituent represented by —SO$_3$R$^b$ is preferably a polynuclear aromatic group having di-nuclear or more and R$^b$ is preferably a hydrocarbon group of 3 to 20 carbon atoms.

Preferable examples of the polynuclear aromatic group include naphthyl, antracenyl and phenanthyl groups and naphthyl group is most preferred.

One or two or more substituents —SO$_3$R$^b$ are present with replacement in the polynuclear aromatic group. When two or more substituents —SO$_3$R$^b$ are present, the substituents may be the same or different each other. In the present invention, the compound most preferably has a structure such that two substituents —SO$_3$R$^b$ are present in the polynuclear ring.

R$^b$ is preferably iso-propyl, n-butyl, neopentyl, tetrahydrofurfuryl, cyclopentyl, cyclohexyl, cyclohexyl methyl, adamanthylmethyl or bicycle[2,2,1]heptylmethyl group, and further preferably neopentyl group.

m is preferably an integer of 0 to 3.

Examples of the aromatic sulfonic acid ester derivative of the formula (1-b) are as follows:

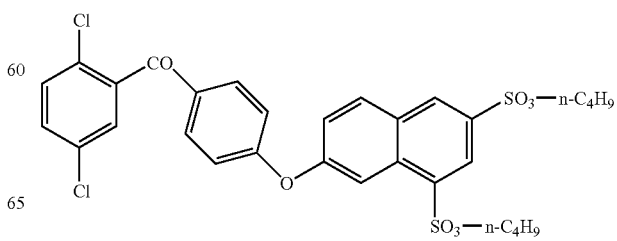

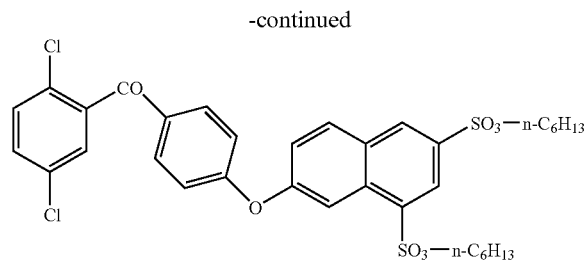

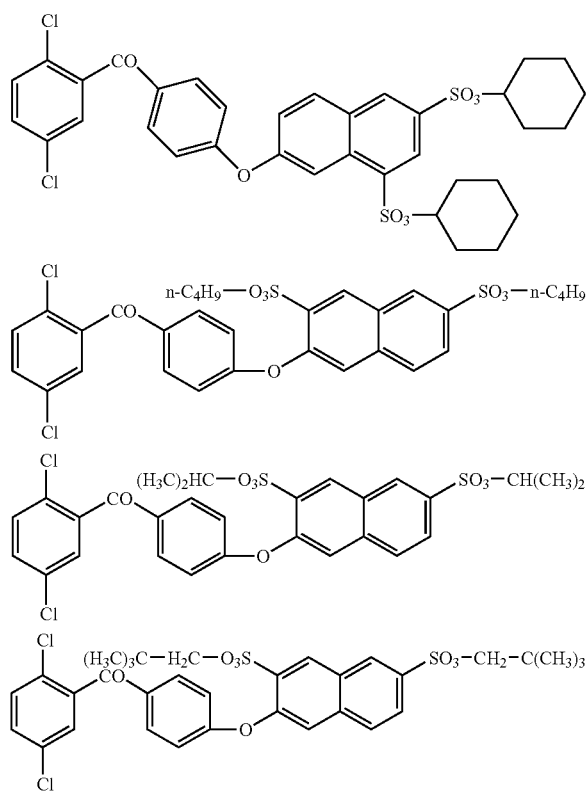

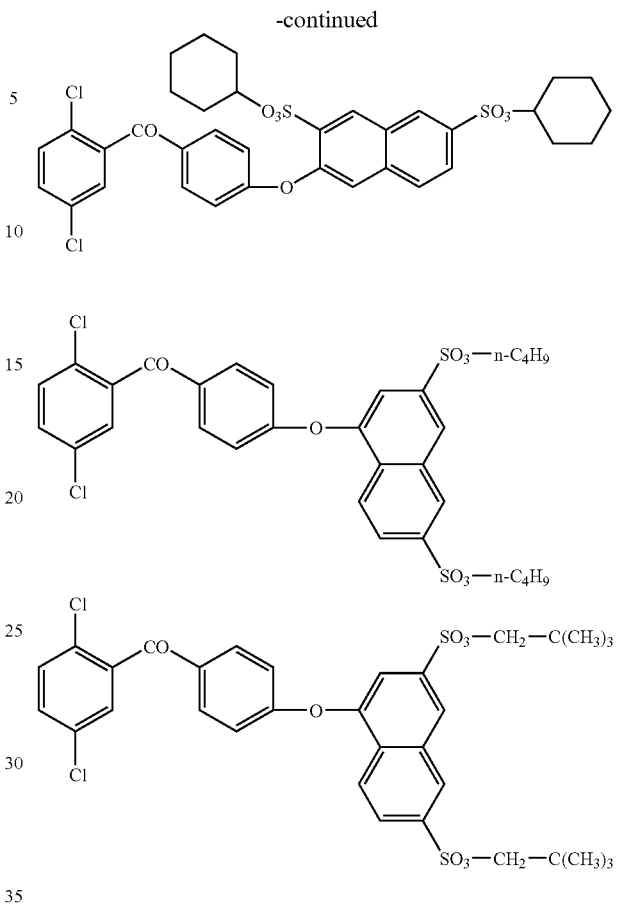

Further examples of the aromatic sulfonic acid ester derivative of the formula (1-b) include compounds obtainable by replacing chlorine atom with bromine atom or iodine atom in the above compounds, compounds obtainable by replacing —CO— with —SO$_2$— in the above compounds and compounds obtainable by replacing chlorine atom with bromine atom or iodine atom and —CO— with —SO$_2$— in the above compounds.

The $R^b$ group in the formula (1-b) is derived from primary alcohol. β carbon is preferably tertiary or quaternary carbon because it has excellent stability in polymerization steps and does not inhibit the polymerization nor induce cross-linking due to generation of sulfonic acid caused by de-esterification. Further, it is preferred that these ester groups be derived from primary alcohol and the β position be quaternary carbon.

Process for Synthesizing the Compound of Type (b)

The compound of type (b), for example, a compound of the formula (1-b) in which Ar is a naphthyl group having a substituent —SO$_3$R$^b$ and m is 1, i.e. a compound represented by the following formula (1-b-1) can be synthesized by, for example, the following method.

(1-b-1)

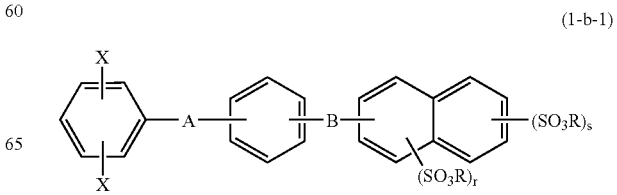

In the formula, A, B and X have the same meanings as those in the formula (1-b), r and s each are an integer of 0 to 4 and satisfy r+s≧1.

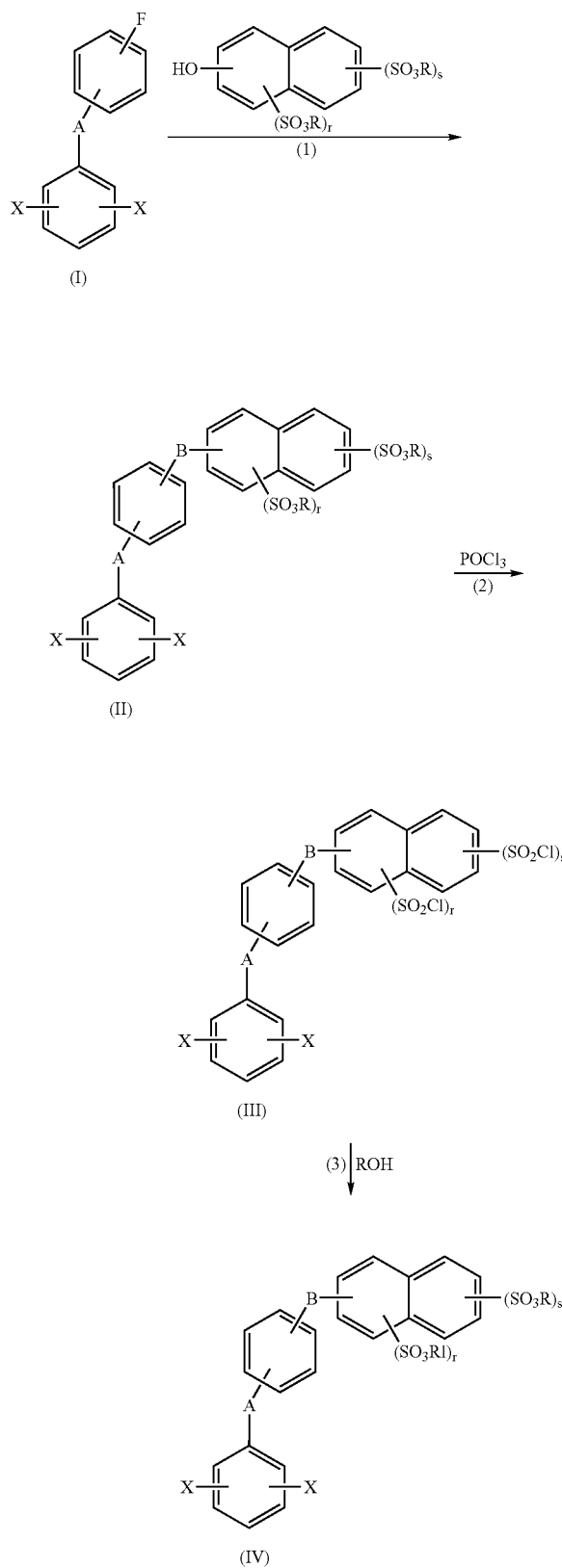

Step (1) Etherification:

By way of illustration, nucleophilic substitution reaction of 2,5-dichloro-4'-fluorobenzophenone as compound (I) with naphthol sulfonic acid is carried out in a non-proton polar solvent such as dimethylsulphoxide, N,N'-dimethylacetoamide, N-methyl pyrrolidone etc in the presence of potassium carbonate, sodium carbonate etc to thereby prepare a naphthalene sulfonic acid derivative. Examples of naphthol sulfonic acid include 2-naphthol-3,6-disulfonic acid, 2-naphthol-6,8-disulfonic acid, 1-naphthol-3,6-disulfonic acid, 2-naphthol-6-sulfonic acid, 1-naphthol-4-sulfonic acid and 2-naphthol-7-sulfonic acid. Of these, 2-naphthol-6,8-disulfonic acid is preferred.

Step (2) Conversion to Sulfonic Acid Chloride:

The naphthalene sulfonic acid derivative as compound (II) is allowed to react with phosphoryl chloride, or thionyl chloride or the like in an organic solvent such as acetonitrile to convert it to sulfonic acid chloride.

Step (3) Esterification:

The sulfonic acid chloride as compound (III) is allowed to react with alcohol in an organic solvent such as pyridine, etc to obtain an aromatic sulfonic acid ester derivative (compound IV).

Compound of Type (c)

The compound type (c) is a compound represented by the following formula (1-c).

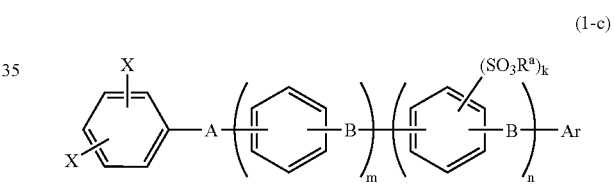

In the formula (1-c), X, A, B, Ar, $R^a$, m, n and k have the same meanings as those in the formula (1), provided that m+n≧1. When n=0, Ar is a phenyl group.

Examples of the aromatic sulfonic acid ester derivative of the formula (1-c) according to the present invention include the following compounds.

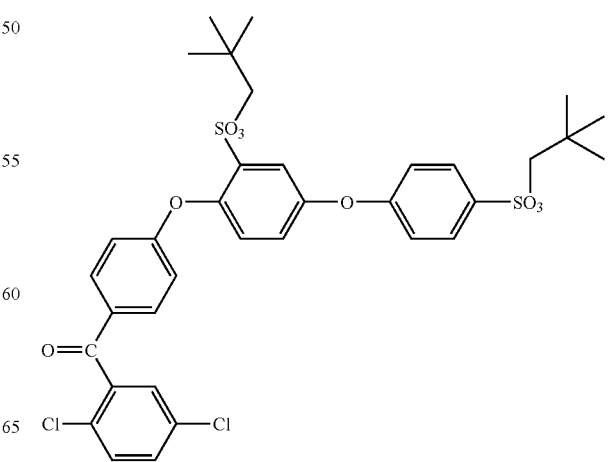

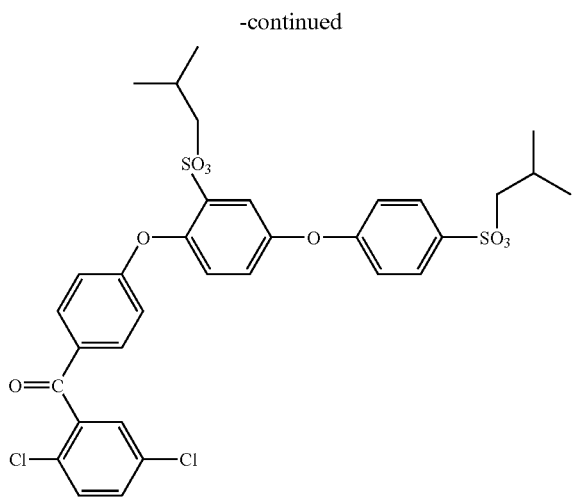
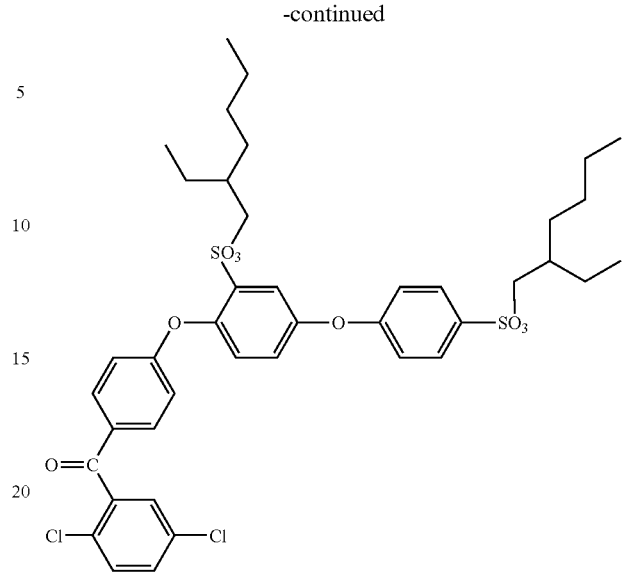
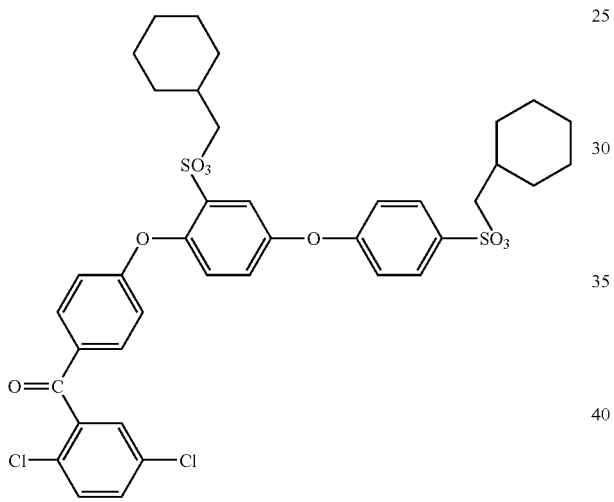
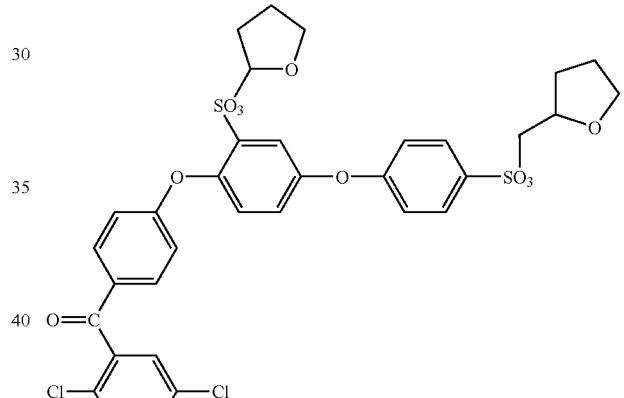
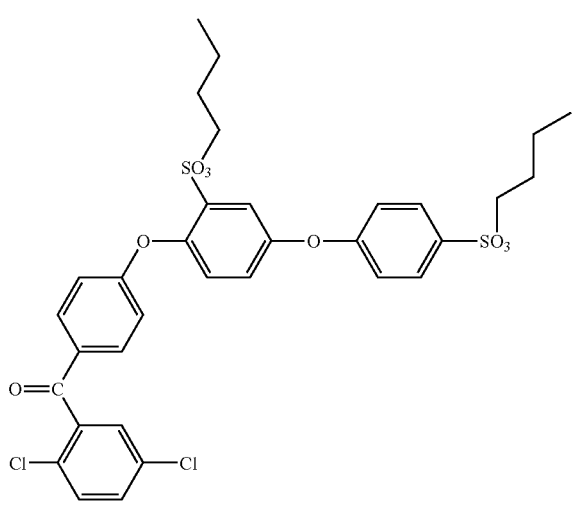
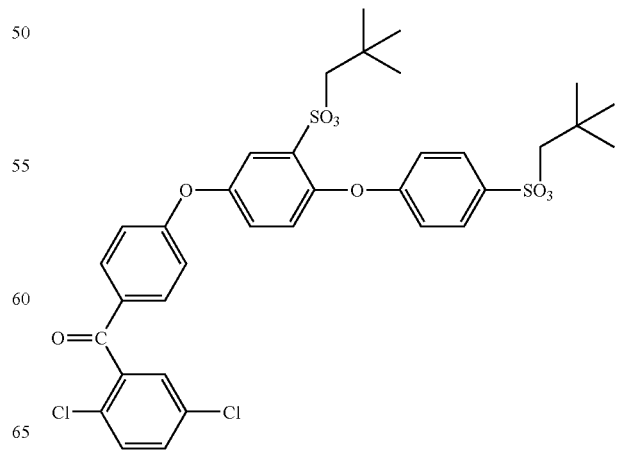

-continued
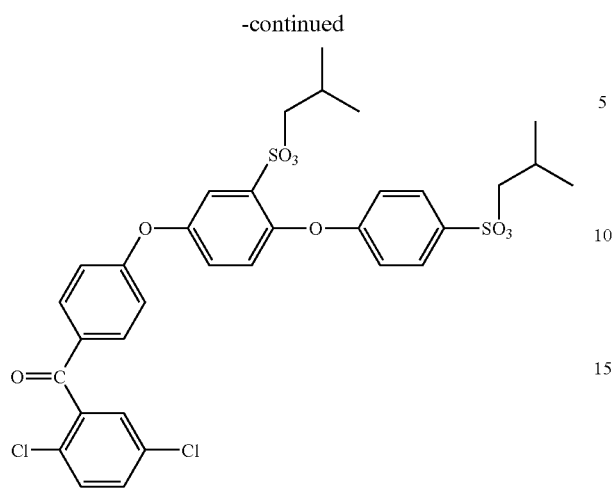
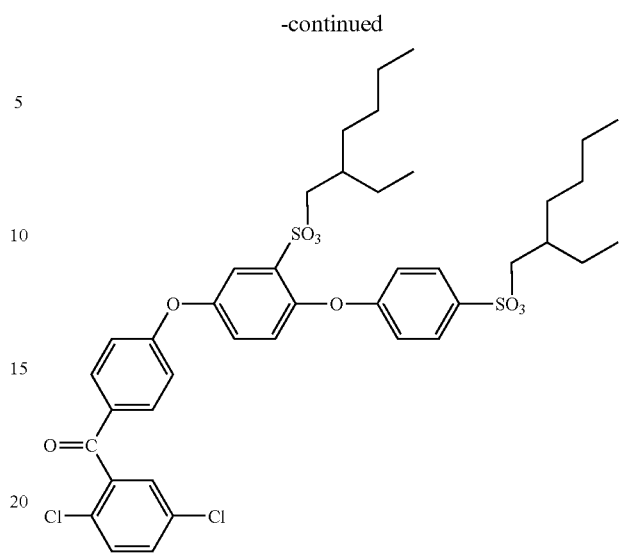
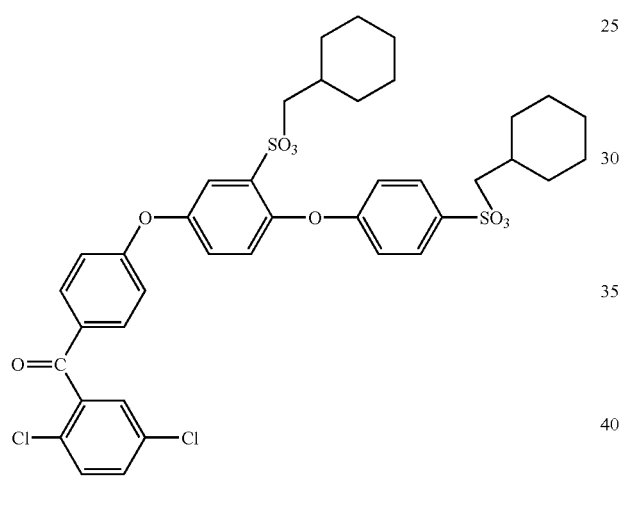
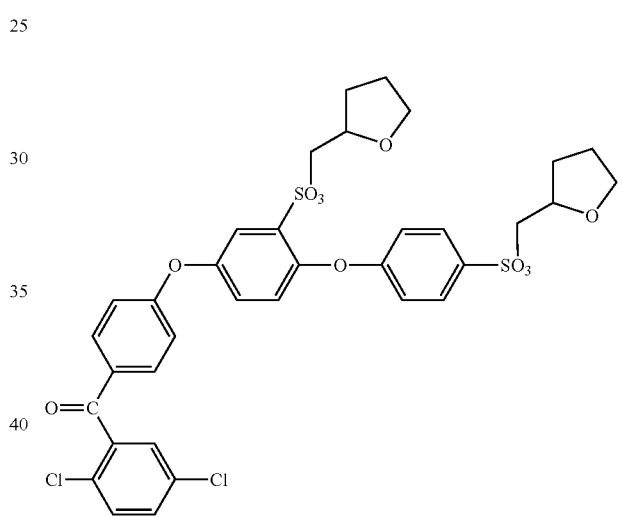
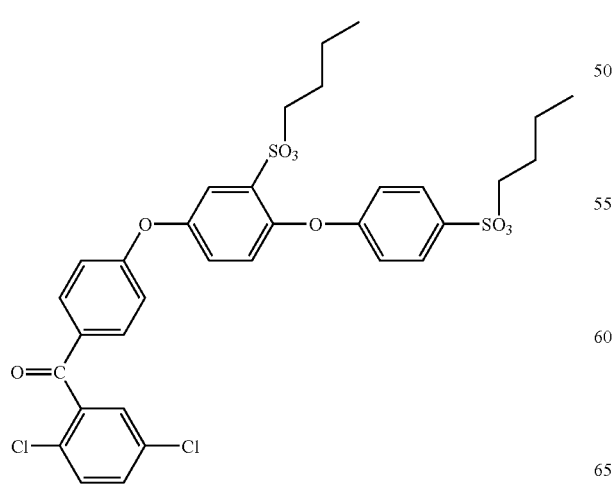
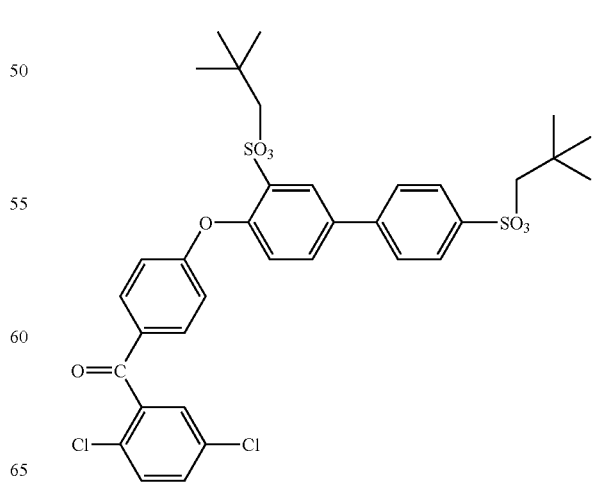

-continued
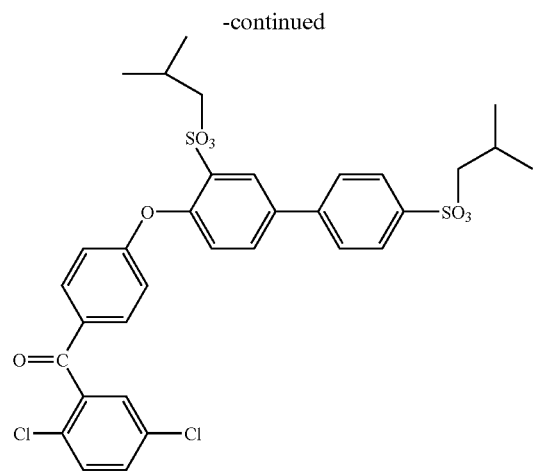
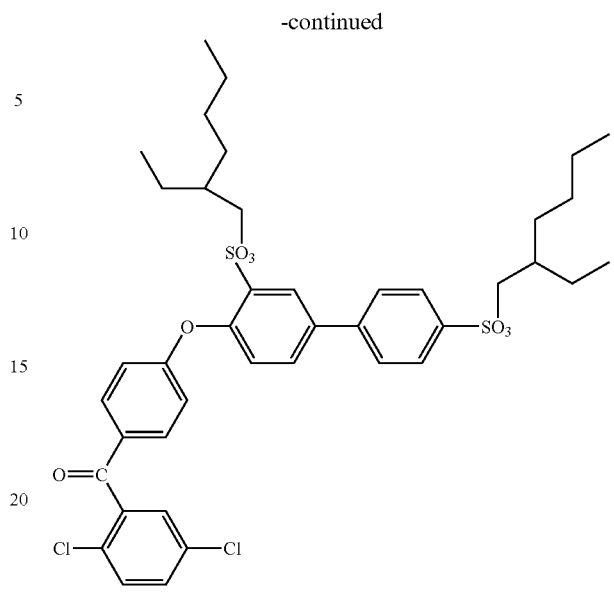
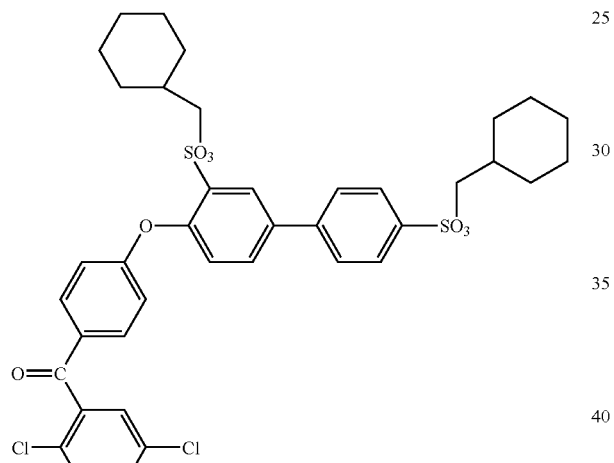
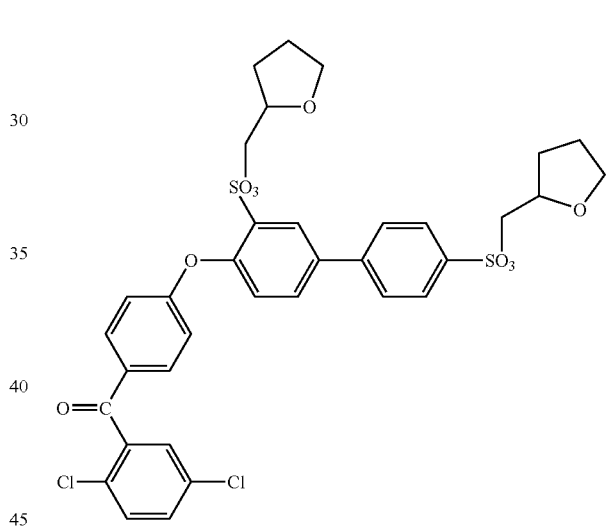
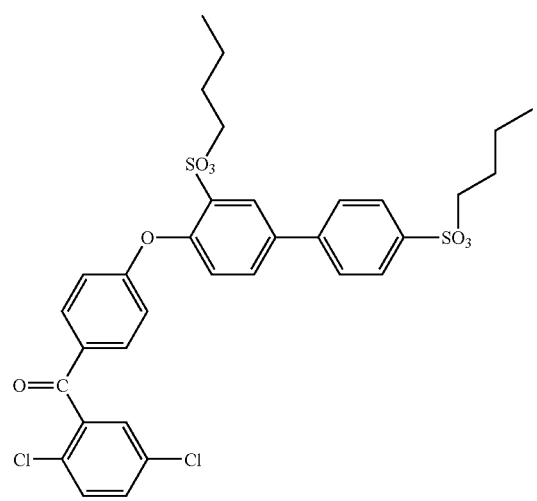
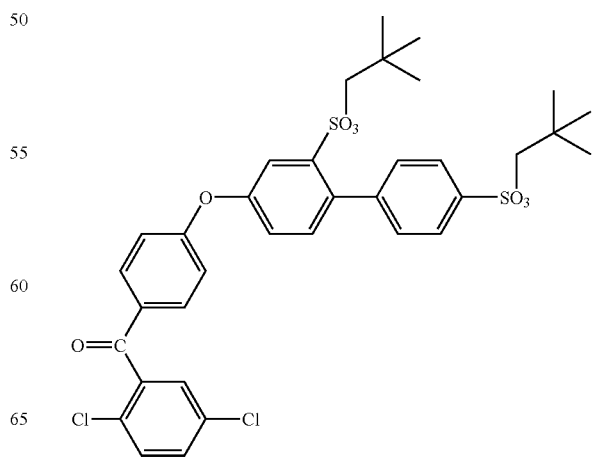

-continued

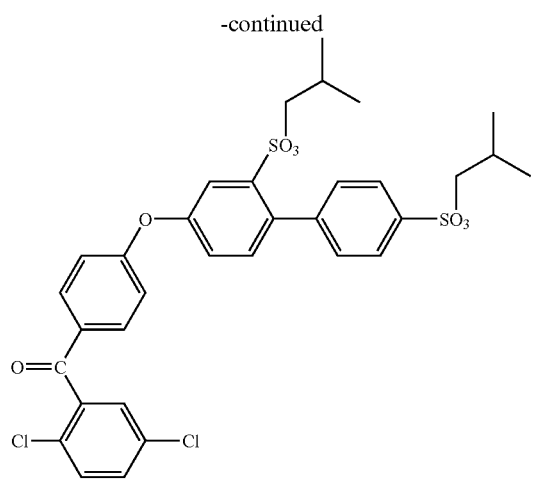

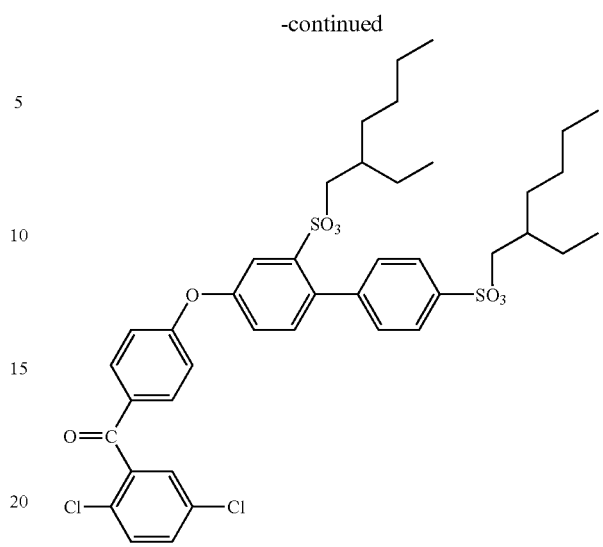

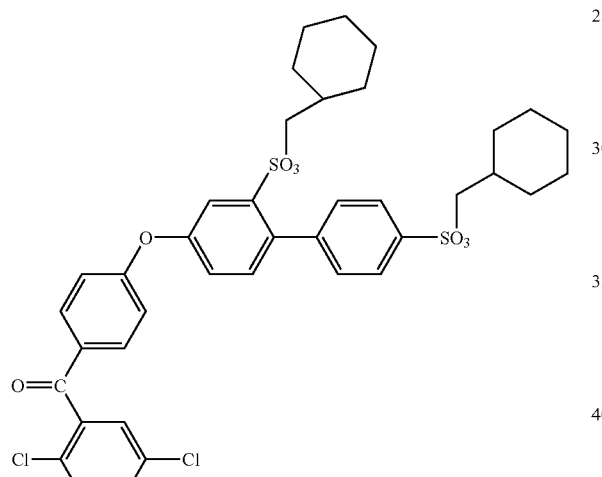

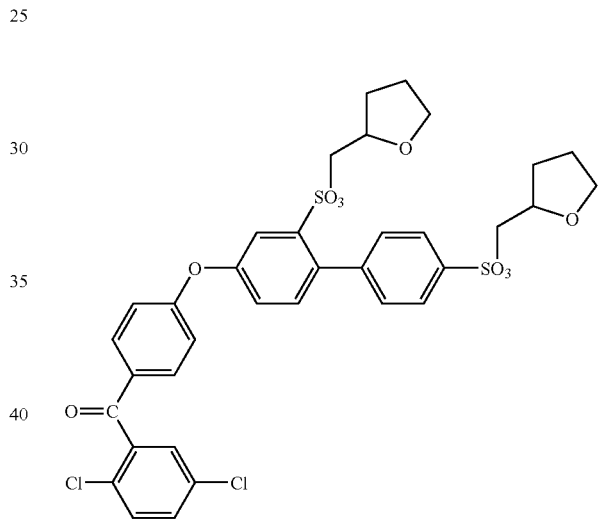

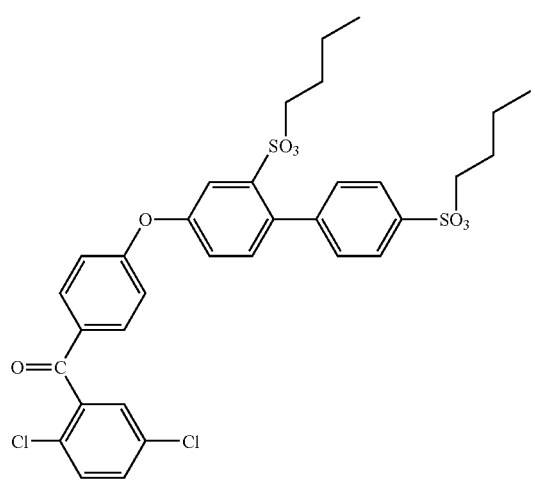

Further examples of the aromatic sulfonic acid ester derivative of the formula (1-c) include compounds obtainable by replacing chlorine atom with bromine atom or iodine atom in the above compounds, compounds obtainable by replacing —CO— with —SO$_2$— in the above compounds and compounds obtainable by replacing chlorine atom with bromine atom or iodine atom and —CO— with —SO$_2$— in the above compounds.

The R$^b$ group in the formula (1-c) is derived from primary alcohol. β carbon is preferably tertiary or quaternary carbon because it has excellent stability in polymerization steps and does not inhibit the polymerization nor induce cross-linking due to generation of sulfonic acid caused by de-esterification. Further, it is preferred that these ester groups be derived from primary alcohol and the β position be quaternary carbon.

Process for Synthesizing the Compound of Type (c)

The compound of type (c) can be synthesized by the following method.

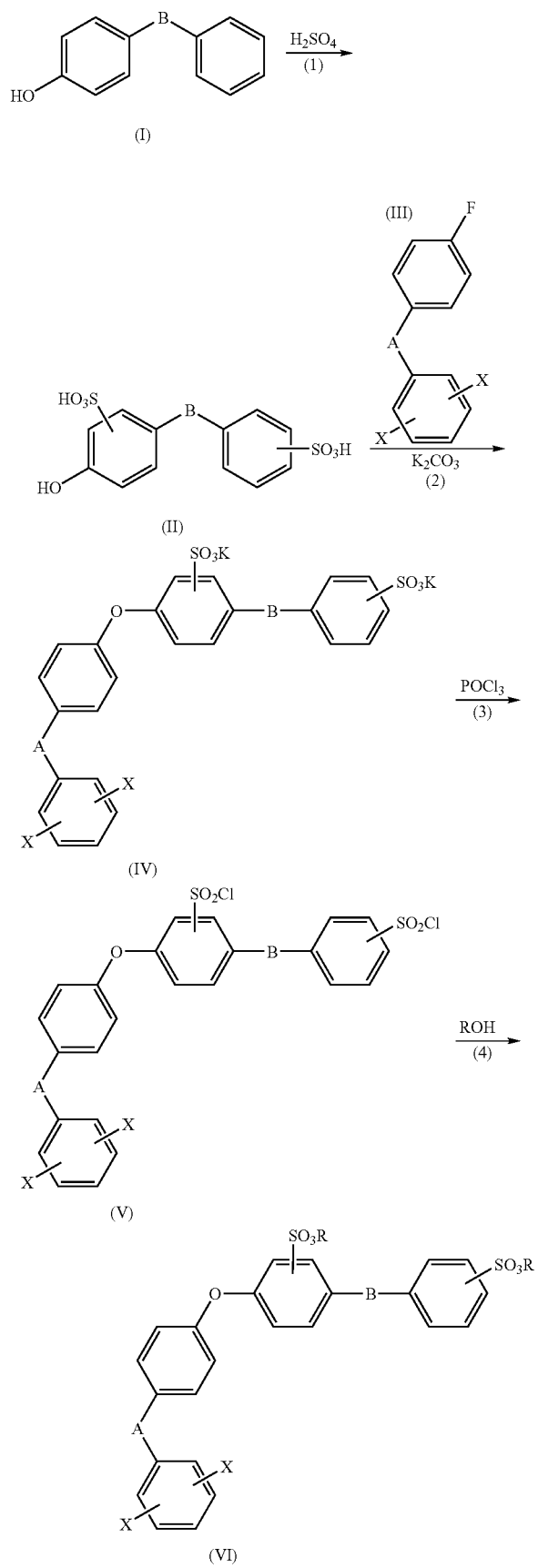

Step (1) Sulfonation:

By way of illustration, 4-phenoxyphenol as compound (I) is reacted in concentrated sulfuric acid at room temperature for 3 hr to obtain a sulfonated product. Using 4-phenylphenol or 4-(4-phenoxy)phenoxy phenol, corresponding sulfonated products can be obtained by the same method as above.

Further, in place of concentrated sulfuric acid, sulfonation may be conducted using a sulfonating agent such as anhydrous sulfonic acid, fuming sulfuric acid, chlorosulfonic acid etc or a complex of these acids and dioxane, acetic acid etc. The position or the number of sulfonic acid for introduction can be regulated by the sulfonating agent for use or the reaction temperature. In the case of isolating the sulfonated product, it may be in the form of free sulfonic acid, or it may be neutralized with an alkali aqueous solution to be a sulfonate such as potassium salt, sodium salt etc.

Step (2) Etherification:

By way of illustration, nucleophilic substitution reaction of 2,5-dichloro-4'-flurobenzophenone as comound (III) and a disulfonate of 4-phenoxy phenol as compound (II) is carried out in the presence of potassium carbonate. Non-proton polar solvents such as N,N-dimethyl acetoamide, dimethylsulfoxide, N-methylpyrrolidone, sulfolane etc can be used as a solvent. Further, the reaction can be advanced smoothly by removing water generated in the beginning of the reaction from the system using a solvent capable of causing azeotropy with water, such as toluene, etc. The reaction temperature is preferably from 100° C. to the boiling point of the solvent. In the case of using 2,5-dichloro-4'-fluorobenzophenone, a fluoro group having higher reactivity than a chloro group selectively reacts and thereby etherification is conducted.

Step (3) Chlorination of Sulfonic Acid:

By way of illustration, the potassium salt of disulfonate of 2,5-dichloro-4'-(4-phenoxy)phenoxy benzophenone as compound (IV), obtained by the above reaction, is allowed to react with phosphoryl chloride, or thionyl chloride or the like etc in an inert solvent such as acetonitrile, etc to convert the sulfonate (potassium salt) into a disulfonyl chloride.

Step (4) Esterification:

By way of illustration, the disulfonyl chloride of 2,5-dichloro-4'-(4-phenoxy)phenoxy benzophenone as compound (V) is allowed to react with various kinds of alcohols having 4 or more carbon atoms in a basic solvent such as pyridine, etc to obtain an aromatic sulfonic acid ester derivative (compound VI).

(Polyarylene Having a Sulfonic Acid Group)

The polyarylene having a sulfonic acid group according to the present invention is prepared by solely polymerizing at least one monomer selected from aromatic sulfonic acid ester derivatives represented by the formula (1), or copolymerizing at least one monomer selected from aromatic sulfonic acid ester derivatives of the formula (1) and other aromatic monomer, preferably at least one monomer selected from compounds represented by the following formula (A), to prepare a polyarylene, followed by hydrolysis of the polyarylene.

(A)

$$\left(\begin{array}{c}R^1\ R^2\\ \\R^3\ R^4\end{array}\right)-W-\left(\begin{array}{c}R^5\ R^6\\ \\R^7\ R^8\end{array}\right)-T-\left(\begin{array}{c}R^5\ R^6\\ \\R^7\ R^8\end{array}\right)-W-\left(\begin{array}{c}R^1\ R^2\\ \\R^3\ R^4\end{array}\right)-R''$$

(with R' on the left)

In the formula (A), R' and R" are identically or differently each a halogen atom excluding fluorine atom or a compound represented by —$OSO_2Z$ wherein Z is an alkyl group, fluorine-substituted alkyl group or aryl group. Exemplary alkyl groups represented by Z are methyl group and ethyl group, an exemplary fluorine-substituted alkyl group is trifluoromethyl group, and exemplary aryl groups are phenyl group and p-tolyl group.

$R^1$ to $R^8$, which may be the same or different, each are at least one atom or group selected from hydrogen, fluorine atom, alkyl group, fluorine-substituted alkyl group, allyl group and aryl group.

Exemplary alkyl groups are methyl, ethyl, propyl, butyl, amyl and hexyl groups, and methyl and ethyl groups are preferred.

Exemplary fluorine-substituted alkyl groups are trifluoromethyl, perfluoroethyl, perfluoropropyl, perfluorobutyl, perfluoropentyl, and perfluorohexyl groups, and trifluoromethyl and pentafluoroethyl are preferred.

An exemplary allyl group is propenyl group.

Exemplary aryl groups are phenyl and pentafluorophenyl groups.

W shows a divalent electron attractive group and examples of the electron attractive group include the same as described above.

T is a divalent organic group and may be an electron attractive group or electron-donating group. Examples of the electron attractive group and electron-donating group include the same as described above.

P is 0 or a positive integer and has a maximum of generally 100, preferably 80.

Examples of the compound represented by the formula (A), in the case that p=0, include 4,4'-dichlorobenzophenone, 4,4'-dichlorobenzanilide, bis(chlorophenyl)difluoromethane, 2,2-bis(4-chlorophenyl)hexafluoropropane, 4-chloro benzoic acid-4-chlorophenyl, bis(4-chlorophenyl) sulfoxide, bis(4-chlorophenyl)sulfone, compounds obtainable by replacing chlorine atom with bromine atom or iodine atom in these compounds, and compounds obtainable by replacing at least one halogen atom substituted at the 4-position to the 3-position.

Examples of the compound represented by the formula (A), in the case that p=1, include 4,4'-bis(4-chlorobenzoyl) diphenylether, 4,4'-bis(4-chlorobenzoylamino)diphenylether, 4,4'-bis(4-chlorophenylsulfonyl)diphenylether, 4,4'-bis(4-chlorophenyl)diphenylether dicarboxylate, 4,4'-bis[(4-chlorophenyl)-1,1,1,3,3,3-hexafluoropropyl]diphenylether, 4,4'-bis[(4-chlorophenyl)-1,1,1,3,3,3-hexafluoropropyl]diphenyl ether, 4,4'-bis[(4-chlorophenyl) tetrafluoroethyl]diphenylether, compounds obtainable by replacing chlorine atom with bromine atom or iodine atom in these compounds, compounds obtainable by replacing at least one halogen atom substituted at the 4-position to the 3-position and compounds obtainable by replacing at least one halogen atom substituted at the 4-position of diphenyl ether to the 3-position.

Further examples of the compound represented by the formula (A) include 2,2-bis[4-{4-(4-chlorobenzoyl) phenoxy}phenyl]1,1,1,3,3,3-hexafluoropropane, bis[4-{4-(4-chlorobenzoyl)phenoxy}phenyl]sulfone and compounds represented by the following formulas.

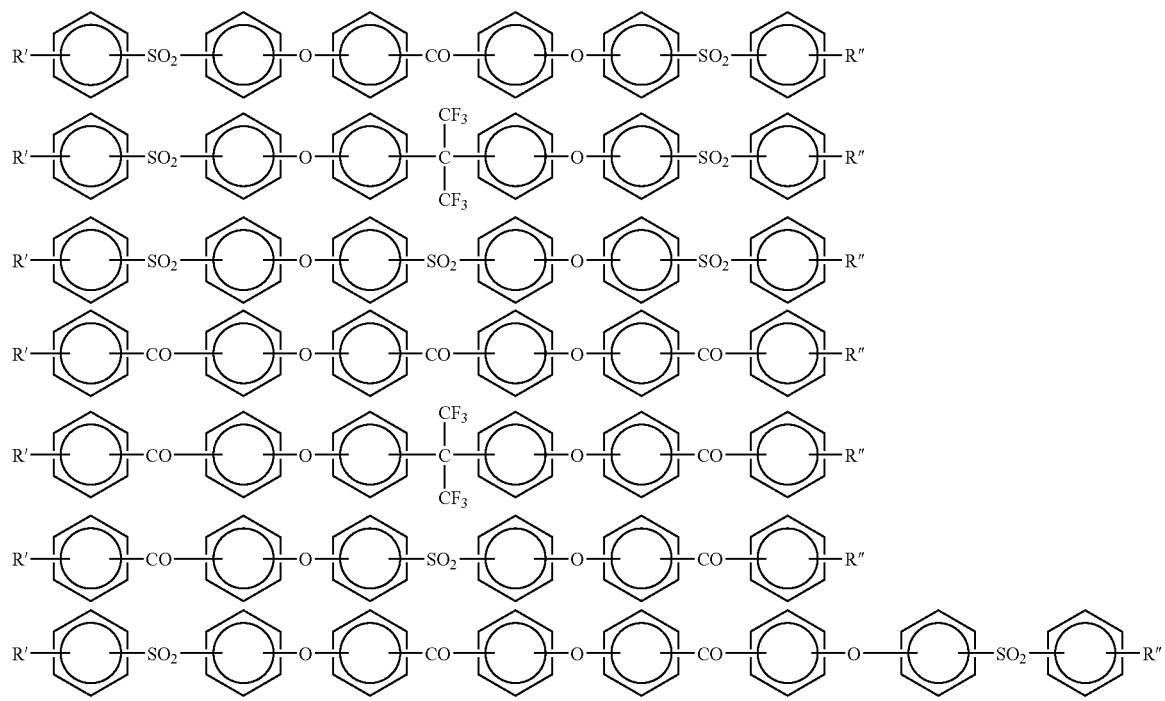

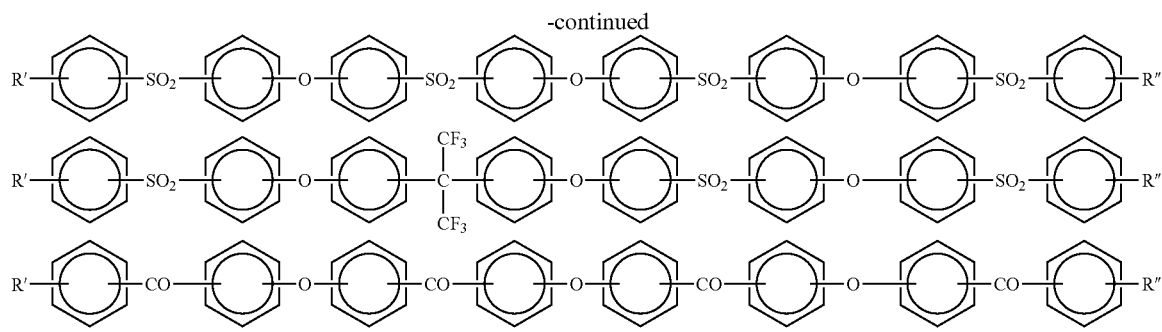

The compounds represented by the formula (A) can be synthesized by, for example, the following method.

First, in order to make bisphenol linked with the electron attractive groups into a corresponding alkali metal salt of bisphenol, an alkali metal such as lithium, sodium, potas- The most preferred method comprises using, as an active aromatic dihalide, a chlorofluoro compound which ends each have a reactivity different halogen atom because fluorine atom preferentially causes nucleophilic substitution reaction with phenoxide so that it is suitable for obtaining the aimed activated chloro end having compound.

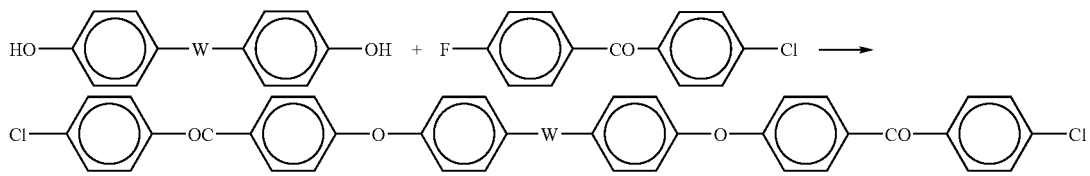

sium etc, hydrogenated alkali metal, alkali metal hydrate, alkali metal carbonate etc are added in a polar solvent having a high dielectric constant such as N-methyl-2-pyrrolidone, N,N-dimethylacetoamide, sulfolane, diphenylsulfone, dimethylsulfoxide etc.

Generally, alkali metal is reacted in a slight excess amount for hydroxyl group of phenol and is usually used in an amount of from 1.1 to 2 equivalent times, preferably 1.2 to 1.5 equivalent times. In this procedure, in the presence of a solvent azeotropic with water such as benzene, toluene, xylene, hexane, cyclohexane, octane, chlorobenzene, dioxane, tetrahydrofurane, anisole, phenetole etc, an aromatic dihalide compound substituted with a halogen atom such as fluorine, chlorine etc which compound is activated by an electron attractive group is reacted. Examples of the aromatic dihalide compound are 4,4'-difluorobenzophenone, 4,4'-dichlorobenzophenone, 4,4'-chlorofluorobenzophenone, bis(4-chlorophenyl)sulfone, bis(4-fluorophenyl)sulfone, 4-fluorophenyl-4'-chlorophenyl sulfone, bis(3-nitro-4-chlorophenyl)sulfone, 2,6-dichlorobenzonitrile, 2,6-difluorobenzonitrile, hexafluorobenzene, decafluorobiphenyl, 2,5-difluorobenzophenone, 1,3-bis(4-chlorobenzoyl)benzene etc. From the standpoint of reactivity, fluorine compounds are preferred. However, in consideration of the following aromatic coupling reaction, it is necessary to arrange aromatic nucleophilic substitution reaction so that the end is a chlorine atom. The active aromatic dihalide is used in an amount of from 2 to 4 mol times, preferably 2.2 to 2.8 mole times per bisphenol. Before the aromatic nucleophilic substitution reaction, the bisphenol may be previously made into an alkali metal salt of bisphenol. The reaction temperature is from 60° C. to 300° C., preferably 80° C. to 250° C. The reaction time is from 15 min to 100 hr, preferably 1 hr to 24 hr.

In the formula, W is the same as defined in the formula (A).

Further, there is a process of synthesizing a flexible compound comprising the aimed electron attractive group and the electron donating group by combing the nucleophilic substitution reaction and electrophilic substitution reaction, as described in JP-A-2(1990)-159.

Specifically, an aromatic bishalide activated with an electro attractive group, for example, (4-chlorophenyl) sulfone and phenol are subjected to nucleophilic substitution reaction to prepare a bisphenoxy substituent. Subsequently, this substituent is subjected to Friedel-Crafts reaction with 4-chloro benzoic acid chloride, to obtain the aimed compound. The above-described compounds are applicable for the aromatic bishalide activated with an electro attractive group used herein. Although the phenol compound may be substituted, the un-substituted phenol compound is preferred from the standpoint of heat resistance and flexing characteristics. The alkali metal salt is preferred for phenol substitution reaction, and preferable examples of the alkali metal compound used herein include the compounds as described above. The alkali metal compound is used in an amount of 1.2 to 2 mol times per 1 mol of phenol. In the reaction, the polar solvent as described above or an azeotropic solvent with water can be used. The bisphenoxy compound is reacted with, as an acylation agent, chlorobenzoic acid chloride in the presence of an activating agent for Friedel-Crafts reaction, for example, a Lewis acid such as aluminum chloride, boron tri-bromide, zinc chloride etc. The chlorobenzoic acid chloride is used in an amount of from 2 to 4 mol times, preferably 2.2 to 3 mol times per the bisphenoxy compound. The activating agent for Friedel-Crafts reaction is used in an amount of from 1.1 to 2 equivalent times per 1 mol of the activated halide compound such as chloro benzoic acid used as an acylation agent. The reaction time is from 15 min to 10 hr, and the reaction time is from −20° C. to 80° C. The solvent used herein include chlrobenzene, nitrobenzene etc which are inactive to Friedel-Crafts reaction.

Further, the compounds represented by the formula (A) wherein p is 2 or more include compounds obtainable by combining bisphenol which is a source of providing an ethereal oxygen as an electron donating group T and at least one group selected from >C=O, —SO$_2$— and >C(CF$_3$)$_2$ as an electron attractive group W. Specifically, the compounds are prepared by subjecting an alkali metal salt of bisphenol such as 2,2-bis(4-hydroxyphenyl)-1,1,1,3,3,3,-hexafluoropropane, 2,2-bis(4-hydroxyphenyl)ketone, 2,2-bis(4-hydroxyphenyl)sulfone etc to substitution reaction with an excess amount of an active aromatic halide compound such as 4,4-dichlorobenzophenone, bis(4-chlorophenyl)sulfone in the presence of the polar solvent such as N-methyl-2-pyrrolidone, N,N-demethylacetoamide, sulfolane etc and then successively polymerizing with the above described synthesizing method of the monomer.

Examples of these compounds include compounds represented by the following formulas.

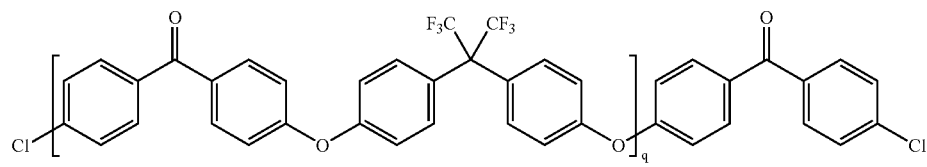

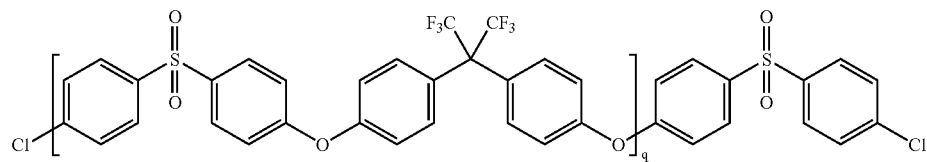

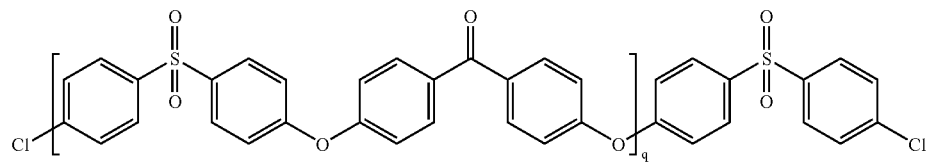

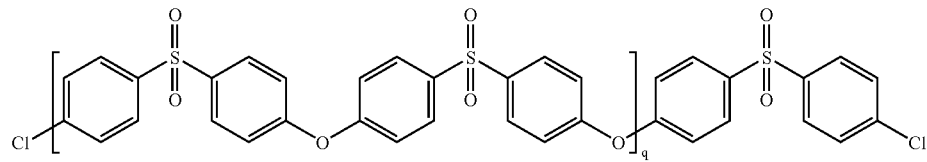

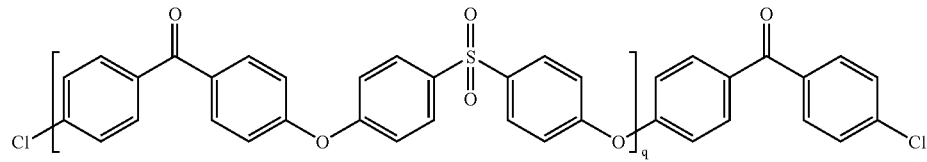

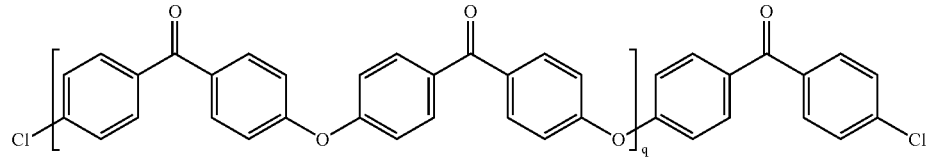

In the above formulas, q is an integer of 2 or more, preferably 2 to 100.

The polyarylene of the present invention comprises repeating structural units derived from an aromatic monomer, which contains at least repeating structural units represented by the following formula (1').

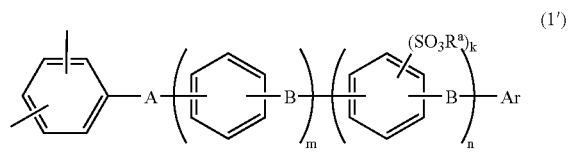

In the formula (1'), A, B, $R^a$ and Ar are the same group as those in formula (1), and m, n and k are also the same as those in the formula (1).

The repeating structural units constituting the polyarylene of the present invention other than formula (1') are represented by, for example, the formula (A').

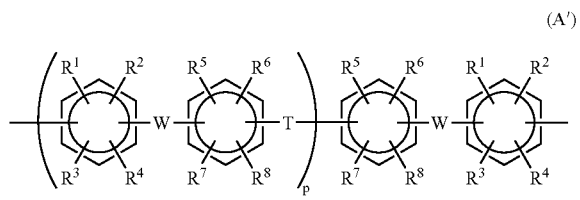

In the formula (A'), $R^1$ to $R^8$, W and T are the same atoms or groups as those in formula (A), and p is also the same number as that in the formula (A).

The content proportion of the repeating structural units of the formula (1') contained in the polyarylene of the present invention, which is not particularly limited, is preferably from 0.5 to 100 mol %, more preferably 10 to 99.999 mol %. Further, the content proportion of the repeating structural units of the formula (A') contained in the polyarylene of the present invention is preferably from 0 to 99.5 mol %, more preferably 0.001 to 90 mol %.

(Synthesis of Polyarylene)

The polyarylene of the present invention is prepared by reacting at least one monomer selected from the aromatic sulfonic acid ester derivatives represented by the formula (1) in the presence of a catalyst or by allowing at least one monomer selected from the aromatic sulfonic acid ester derivatives represented by the formula (1) in an amount of from 0.5 to 100 mol %, more preferably 10 to 99.999 mol % to react with other aromatic monomer, preferably at least one monomer selected from the compounds represented by the formula (A) in an amount of from 0 to 99.5 mol %, preferably 0.001 to 90 mol % in the presence of a catalyst. The catalyst used in the reaction is a catalyst system containing a transition metal compound. The catalyst system comprises (1) a transition metal salt and a compound for a ligand (hereinafter referred to "ligand component"), or a transition metal complex having a ligand coordinated (containing a copper salt), and (2) a reducing agent and optionally a salt in order to enhance the polymerization rate.

Examples of the transition metal salt include nickel compounds such as nickel chloride, nickel bromide, nickel iodide and nickel acetyl acetonate; palladium compounds such as palladium chloride, palladium bromide and palladium iodide; iron compounds such as ferric chloride, ferric bromide and ferric iodide; and cobalt compounds such as cobalt chloride, cobalt bromide and cobalt iodide. Of these nickel chloride and nickel bromide are preferred.

Examples of the ligand component include triphenyl phosphine, 2,2'-bipyridine, 1,5-cyclooctadiene, 1,3-bis (diphenylphosphino)propane etc. Of these, triphenylphosphine and 2,2'-bipyridine are preferred. The above compound used for the ligand component may be used singly or in combination with two or more.

Further, examples of the ligand-coordinated transition metal complex include nickel chloride bis(triphenyl phosphine), nickel bromide bis(triphenyl phosphine), nickel iodide bis(triphenyl phosphine), nickel nitride bis(triphenyl phosphine), nickel chloride(2,2'-bipyridine), nickel bromide (2,2'-bipyridine), nickel iodide(2,2'-bipyridine), nickel nitride(2,2'-bipyridine), bis(1,5-cyclooctadiene)nickel, tetrakis(triphenylphosphine)nickel, tetrakis(triphenylphosphite)nickel, tetrakis(triphenylphosphine)paradium etc. Of these, nickel chloride bis(triphenylphosphine) and nickel chloride(2,2'-bipyridine are preferred.

The reducing agent used in the above catalyst system include, for example, iron, zinc, manganese, aluminum, magnesium, sodium, calcium etc. Of these, zinc, magnesium and manganese are preferred. These reducing agents are further activated for use by allowing the reducing agents to contact with an acid such as organic acids, etc.

The salt used in the above catalyst system include sodium compounds such as sodium fluoride, sodium chloride, sodium bromide, sodium iodide and sodium sulfate; potassium compounds such as potassium fluoride, potassium chloride, potassium bromide, potassium iodide and potassium sulfate; and ammonium compounds such as tetraethyl ammonium fluoride, tetraethyl ammonium chloride, tetraethyl ammonium bromide, tetraethyl ammonium iodide and tetraethyl ammonium sulfate. Of these, sodium bromide, sodium iodide, potassium bromide, tetraethyl ammonium bromide and tetraethyl ammonium iodide are preferred.

With regard to the proportion of each component used, the transition metal salt or transition metal complex is usually used in an amount of from 0.0001 to 10 moles, preferably 0.01 to 0.5 mole based on 1 mole of the total amount of the monomers. When the amount is less than 0.0001 mole, the polymerization reaction occasionally does not proceed sufficiently, on the other hand, when the amount is over 10 moles, the molecular weight occasionally lowers.

In the catalyst system, when the transition metal salt and the ligand component are used, the ligand component is used in an amount of usually from 0.1 to 100 moles, preferably 1 to 10 moles based on 1 mole of the transition metal salt. When the amount is less than 0.1 mole, the catalyst activity is occasionally insufficient, on the other hand, when the amount is over 100 moles, the molecular weight occasionally lowers.

The amount of the reducing agent used is usually from 0.1 to 100 mole, preferably 1 to 10 mole based on 1 mole of the total amount of the monomers. When the amount is less than 0.1 mole, the polymerization occasionally does not proceed sufficiently, on the other hand, when it is over 100 moles, purification of the resulting polymer is occasionally difficult.

Additionally, when the salt is used, the amount thereof is usually from 0.001 to 100 moles, preferably 0.01 to 1 mole based on 1 mole of the total amount of the monomers. When the amount is less than 0.001 mole, the effect of increasing the polymerization rate is occasionally insufficient, on the other hand, when the amount is over 100 moles, purification of the resulting polymer is occasionally difficult.

The polymerization solvent used herein include tetrahydrofuran, cyclohexanone, dimethylsulfoxide, N,N-dimethylformamide, N,N-dimethylacetoamide, N-methyl-2-pyrrolidone, ν-butylolactone, sulfolane, ν-butylolactam, dimethylimidazolidinone, tetramethyl urea etc. Of these, tetrahydrofrane, N,N-dimethylformamide, N,N-dimethylacetoamide and N-methyl-2-pyrrolidone are preferred. These polymerization solvents are preferably dried sufficiently before use.

The concentration of the total of the monomers contained in the polymerization solvent is usually from 1 to 90% by weight, preferably 5 to 40% by weight.

Further, the polymerization temperature in polymerization is usually from 0 to 200° C., preferably 50 to 120° C. The polymerization time is usually 0.5 to 100 hr, preferably 1 to 40 hr.

In this manner, at least one monomer selected from the aromatic sulfonic acid ester derivatives represented by the formula (1) is (co)polymerized, or at least one monomer selected from the aromatic sulfonic acid ester derivatives represented by the formula (1) and at least one monomer selected from the compounds represented by the formula (A) are copolymerized to obtain a polymerization solution containing polyarylene.

The polyarylene thus obtained has a molecular weight, i.e. weigh average molecular weight in terms of polystyrene, as determined by Gel permeation chromatography (GNP), of from 10,000 to 1,000,000, preferably 20,000 to 800,000.

(Polyarylene Having a Sulfonic Acid Group)

The polyarylene having a sulfonic acid group according to the present invention is prepared by converting sulfonic acid ester groups ($—SO_3R^a$, $—SO_3R^b$) in repeating structural units of the formula (1') into a sulfonic acid group ($—SO_3H$) with hydrolysis of the above polyarylene.

Exemplary Hydrolyses Include:
(1) a process of introducing the above polyarylene into an excess amount of water or alcohol each containing a small amount of hydrochloric acid, and then stirring for 5 min or more.
(2) a process of reacting the above polyarylene in trifluoroacetic acid at a temperature of about from 80 to 120° C. for about 5 to 10 hr, and
(3) a process of reacting the above polyarylene in a solution containing 1 to 3 mol times of lithium bromide based on 1 mole of the sulfonic acid groups ($—SO_3R^a$, $—SO_3R^b$) contained in the polyarylene, for example, a solution of N-methyl pyrrolidone, at a temperature of about from 80 to 150° C. for about 3 to 10 hr, and thereafter adding hydrochloric acid.

The polyarylene having a sulfonic acid group thus obtained has a sulfonic acid amount of from 0.5 to 3 meq/g, preferably 0.8 to 2.8 meq/g. When the amount is less than 0.5 meq/g, the proton conductive properties is not increased, on the other hand, when the amount is over 3 meq/g, the hydrophilicity is enhanced and the resulting polyarylene is soluble in water, or even if insoluble in water, it is soluble in hot water, and further, even if it is not soluble in water, however, the durability is lowered.

The amount of the sulfonic acid group can be easily regulated by varying the proportion of the aromatic sulfonic acid ester derivative (1) and the compound (A), and further the kind of a monomer and the combination thereof.

The structure of the polyarylene having a sulfonic acid can be confirmed from C—O—C absorption at 1,230 to 1,250 cm$^{-1}$, or C=O absorption at 1,640 to 1,660 cm$^{-1}$ by infrared absorption spectrum, and further can be confirmed from the peak of aromatic proton at 6.8 to 8.0 ppm by nuclear magnetic resonance spectrum ($^1$H-NMR).

In the present invention, it is preferred that 90% or more of the sulfonic acid groups ($—SO_3R^a$, $—SO_3R^b$) contained in the polyarylene is converted to a sulfonic acid group ($—SO_3H$).

(Polymer Solid Electrolyte)

The polymer solid electrolyte according to the present invention comprises the polyarylene having a sulfonic acid group as described above.

The polymer solid electrolyte of the present invention is applicable to, for example, electrolytes for primary battery, electrolytes for secondary battery, proton-conductive membranes for fuel cell, display elements, various sensors, signal transmitting media, solid condenser, ion exchange membranes etc.

(Proton-conductive Membrane)

The proton-conductive membrane of the present invention comprises the polyarylene having a sulfonic acid group. In preparing the proton-conductive membrane from the polyarylene having a sulfonic acid group, inorganic acids such as sulfuric acid, phosphoric acid etc, organic acids containing carboxylic acid and an appropriate amount of water may be simultaneously used in addition to the polyarylene having a sulfonic acid group.

In the present invention, the polyarylene having a sulfonic acid group is dissolved in a solvent to prepare a solution, the resulting solution is cast onto a substrate by casting and molded into a film by a casting method of forming into a film and thereby the proton-conductive membrane can be prepared. In this case, the substrate is not particularly limited as long as it can be used for a usual solution casting method. For example, plastic or metal substrates are used, preferably substrates made of thermoplastic resins, such as polyethylene terephthalate (PET) film are used.

The solvent capable of dissolving the polyarylene having a sulfonic acid group include, for example, non-proton polar solvents such as N-methyl-2-pyrrolidone, N,N-dimethyl formamide, ν-butylolactone, N,N-dimethyl acetoamide, dimethylsulfoxide, dimethyl urea, dimethyl imidazolidinone etc, particularly, N-methyl-2-pyrrolidone (hereinafter referred to as "NMP") is preferred from the standpoint of solubility and solution viscosity. The non-proton polar solvents may be used singly or in combination with two or more.

As the solvent capable of dissolving the polyarylene having a sulfonic acid group, a mixture of the above non-proton polar solvent and alcohol may be used. Examples of the alcohol include methanol, ethanol, propyl alcohol, iso-propyl alcohol, sec-butyl alcohol, tert-butyl alcohol etc, and particularly, methanol is preferred because of having the effect of lowering the solution viscosity in a wide composition range. The alcohols may be used singly or in combination with two or more.

The solution viscosity, although depends the molecular weight of the polyarylene having a sulfonic acid group or the polymer concentration, is usually from 2,000 to 100,000 mPa·s, preferably 3,000 to 50,000 mPa·s. When the solution viscosity is less than 2,000 mPa·s, the solution has inferior retentivity during film forming and occasionally flows from the substrate. On the other hand, when it is over 100,000 mPa·s, the viscosity is too high and thereby extrusion from a die cannot be conducted and film forming with casting is occasionally difficult.

In the case of using a high boiling point-having solvent as the casting solvent, the film prepared in the above manner sometimes has a large amount of the solvent remained, but when the resulting green film is immersed in water, the solvent contained in the green film can be replaced with water and thereby the solvent remained in the resulting film can be decreased.

Applicable examples of the process of immersing the green film in water may be a batch method of immersing sheets in water and a continuous method of immersing a laminated film in a state of a membrane formed on a generally obtained substrate film (e.g. PET), or a membrane separated from the substrate, in water and then winding up.

The batch method is preferred because of depressing wrinkle forming caused on the surface of the film due to treatment with a process of fitting the treated film into a frame.

The green film is preferably immersed in water in a contact proportion of not less than 10 parts by weight, preferably 30 parts by weight per 1 part by weight of the green film. It is preferred to keep the contact proportion as large as possible in order to decrease the solvent amount remained in the resulting proton-conductive membrane. Further, it is effective for decreasing the solvent amount remained in the resulting proton-conductive membrane to change water used in immersing or keep the organic solvent concentration in water a fixed concentration or lower by overflowing. It is effective for depressing the in-plane distribution of the organic solvent remained in the proton-conductive membrane to homogenize the organic solvent concentration in water with stirring, etc.

The proton-conductive membrane prepared by such a method has a dried thickness of usually from 10 to 100 μm, preferably 20 to 80 μm.

In the present invention, furthermore, the polyarylene is molded into a film by the above described method without hydrolysis, and thereafter subjected to hydrolysis in the same method as described above and thereby the proton-conductive membrane comprised of the polyarylene having a sulfonic acid group can be also prepared.

The aromatic sulfonic acid ester derivative and polyarylene according to the present invention are used for the polyarylene having a sulfonic acid as described above and the process for producing the same.

EXAMPLE

The present invention will be described in more detail with reference to the following non-limiting examples hereinafter.

In Examples, measurement on the amount of a sulfonic acid group, proton conductance and thermal decomposition initiating temperature, and evaluation on tensile strength properties, resistance to hot water and resistance to Fenton reagent were conducted in the following manner.

Measurement on the Amount of Sulfonic Acid Group

The resulting polyarylene having a sulfonic acid group was sufficiently washed with water until rinsing water was neutral, to remove free acid remained, and dried. A prescribed amount of the resulting product was weighed out and dissolved in a THF/water mixed solvent, and titration was carried out using phenolphthalein as an indicator and a NaOH standard solution, and the amount of sulfonic acid was determined from a neutralization point.

Measurement on Proton Conductance

Alternating current resistance was determined by holding a platinum wire ($\phi$=0.5 mm) on the surface of a strip-like cut film having a width of 5 mm and retaining a sample in a constant temperature and constant moisture apparatus and measuring alternating current impedance between the platinum wires. That is, impedance at an alternating current of 10 kHz was measured in the environment as described later. A chemical impedance measuring system (manufactured by NF circuit design block Co., Ltd.) was used as a resistance measuring apparatus and JW241 manufactured by Yamato Scientific Co. Ltd. was used as a constant temperature and constant moisture apparatus. Five platinum wires were holed at a distance of 5 mm, the distance between the wires was changed to from 5 to 20 mm and the alternating current resistance was measured. The specific resistance of the film was calculated from the wire distance and the gradient of the resistance, the alternating current impedance was calculated from the inverse number of the specific resistance, and the proton conductance was calculated from this impedance.

Specific resistance $R(\Omega\cdot cm)$=0.5 (cm)×film thickness (cm)×gradient between resistance wires ($\Omega$/cm)

Tensile Strength Properties

A 3 mm×65 mm strip-like cut film specimen was prepared and measured on modulus of elasticity, breaking strength and elongation using a tensile tester.

Test for Resistance to Hot Water

A film was cut to a 2.0 cm×3.0 cm rectangle and weighed to prepare a test piece for the test. This film was put into a 250 mL polycarbonate bottle and therein about 100 mL of distilled water was added and heated at 120° C. for 24 hr using a pressure cooker tester (PC-242HS manufactured by HIRAYAMA MFS CORP). After completion of the test, each film was taken out from hot water and water present on the surface was lightly wiped with KIMWIPE (Trade Name). The film containing water was weighed to determine a water-content. Further, the dimension of the film was measured to determine a degree of swelling. Additionally, this film was dried for 5 hr with a vacuum dryer and thereby water was distilled off, and then the film prepared after the hot water test was weighed to determine a weight residue.

Test for Resistance to Fenton Reagent

A film was cut to a 3.0 cm×4.0 cm rectangle and weighed to prepare a test piece for the test. Each test piece was immersed in 200 mL of distilled water for 48 hr and thereby a residual solvent contained in the film was eluted. In this procedure, distilled water was changed twice. After the water immersing, the film was sandwiched with a filter and thereby water present on the surface was sucked up and then the film was air-dried over night and weighed.

A commercially available 30% hydrogen peroxide solution was diluted with distilled water to prepare a 3% hydrogen peroxide solution. To the solution, a ferrous sulfate-7-hydrate was added and dissolved so that Fe(II) ion was 20 ppm, and thereby Fenton reagent was regulated. 200 mL of this solution was poured into a 250 mL polyester bottle and heated and kept at 45° C. using a water bath. After it was confirmed that the solution temperature was 45° C., each film was introduced into the bottle and heated for 26 hr. After the passage of 26 hr, a solid was taken out from the solution and air-dried over night. The solid was weighed to determine a weight residue.

Thermal Decomposition Temperature

The decomposition temperature of polyarylene having a sulfonic acid group measured with TGA (Thermogravimetric analysis) (in a nitrogen atmosphere, temperature-elevating rate of 20° C./min) was taken as a thermal decomposition temperature.

Example 1

(1) Preparation of Sodium Salt of 4-[4-(2,5-dichlorobenzoyl)phenoxy]benzene sulfonic acid (A-SO₃Na)

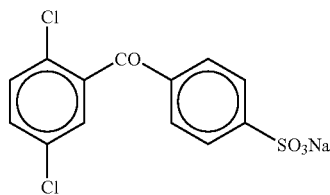

Figure 2:
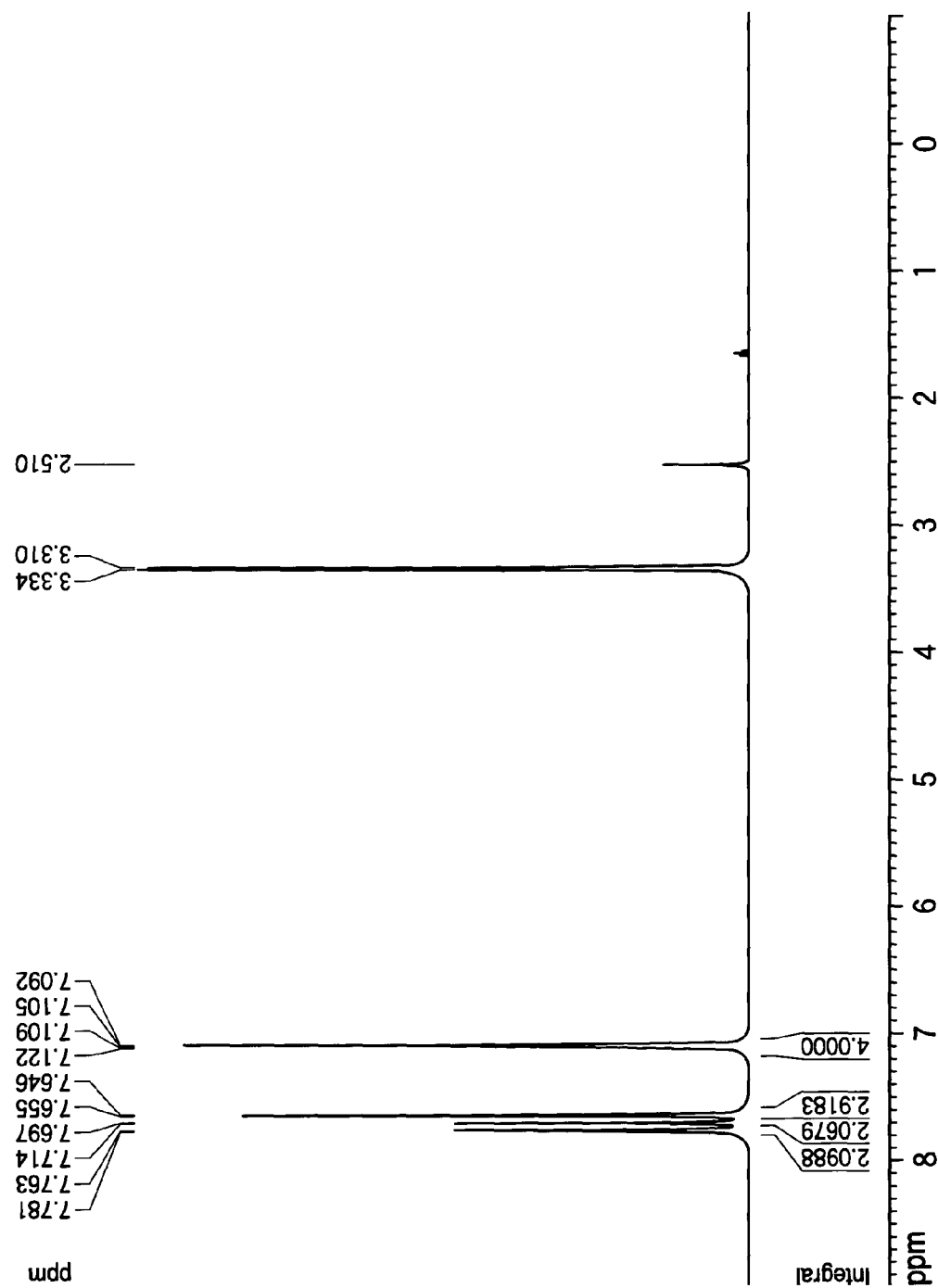
FIG. 2 is an NMR spectrum of a white powder prepared in Example 1 (1).
Figure 3:
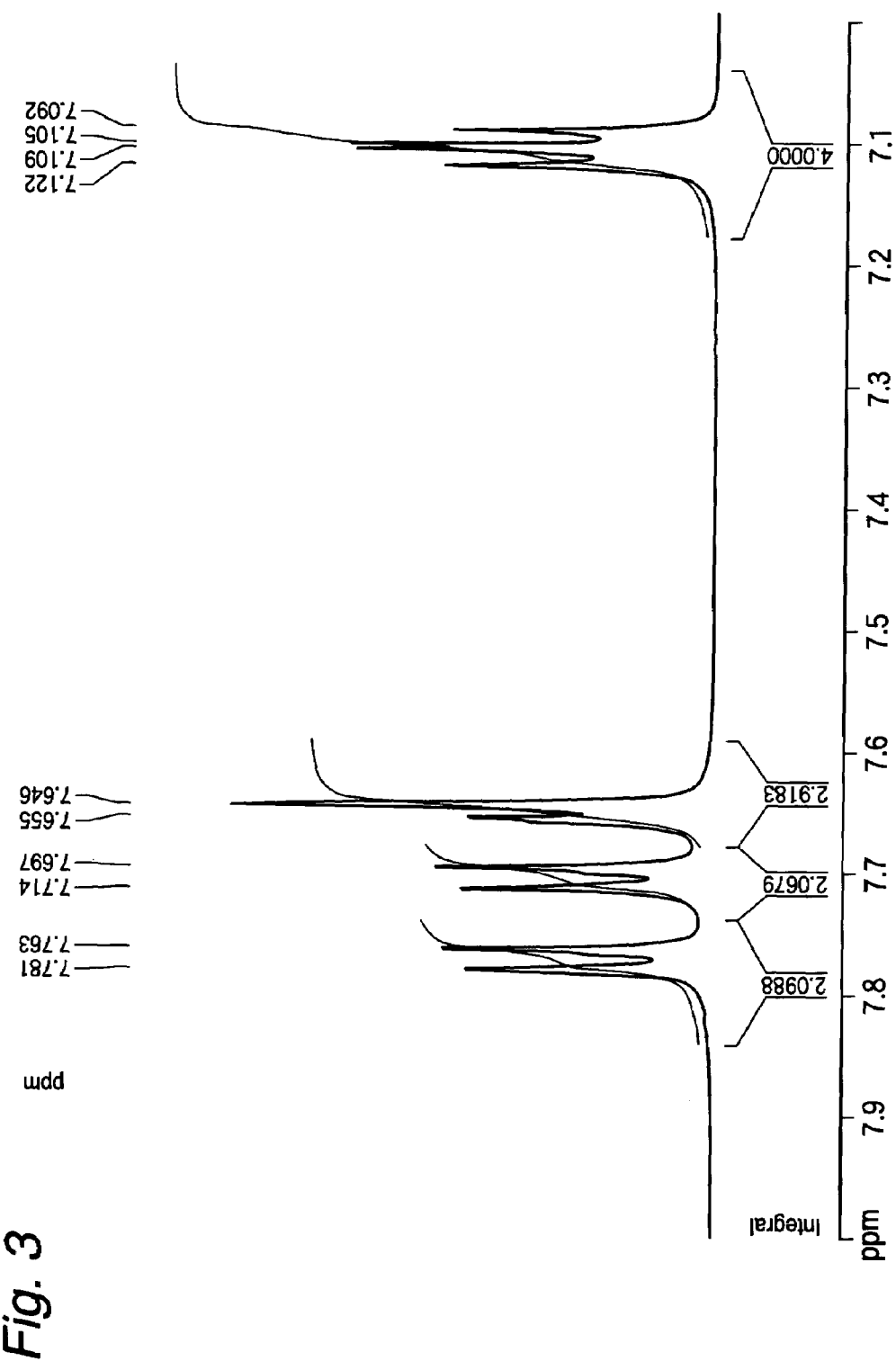
FIG. 3 is an NMR spectrum of a white powder prepared in Example 1 (1).

To a three-necked flask equipped with a stirrer and a cooling tube, 2,5-dichloro-4'-phenoxybenzophenone (A, 137.3 g, 400 mmol) was added and subsequently, 500 mL of 1,2-dichloroethane(1,2-DCE) was added and dissolved. Additionally, a 2M acetyl sulfuric acid newly prepared from 56 mL of concentrated sulfuric acid, 152 mL of acetic anhydride and 400 mL of 1,2-DCE was added to the solution with stirring and reacted in an oil bath at 60° C. for 3 hr. After the prescribed time, the reaction was stopped by adding 300 mL of 1-propanol. Subsequently, the reaction solution was concentrated until the volume was 400 mL, and then a NaOH aqueous solution (120 g(3 mol)/water 400 mL) was added. 1,2-DCE remained in the solution was distilled off with azeotrope and then the resulting transparent pale yellow solution was cooled to obtain a precipitate and the precipitate deposited was filtered. The precipitate was vacuum dried at 70° C. and thereby the aimed sodium salt of 4-[4-(2,5-dichlorobenzoyl)phenoxy]benzene sulfonic acid (A-SO₃Na) was obtained as a white fine powder. The crude crystal was used to the following step without purification. With regard to the resulting white powder, the IR spectrum is shown in FIG. 1 and the NMR spectrum is shown in FIGS. 2 and 3.

(2) Preparation of 4-[4-(2,5-dichlorobenzoyl)phenoxy]benzene sulfonic acid chloride (A-SO₂Cl)

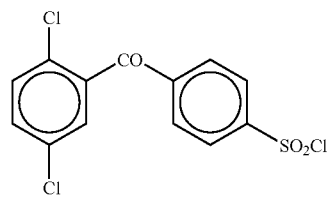

Figure 4:
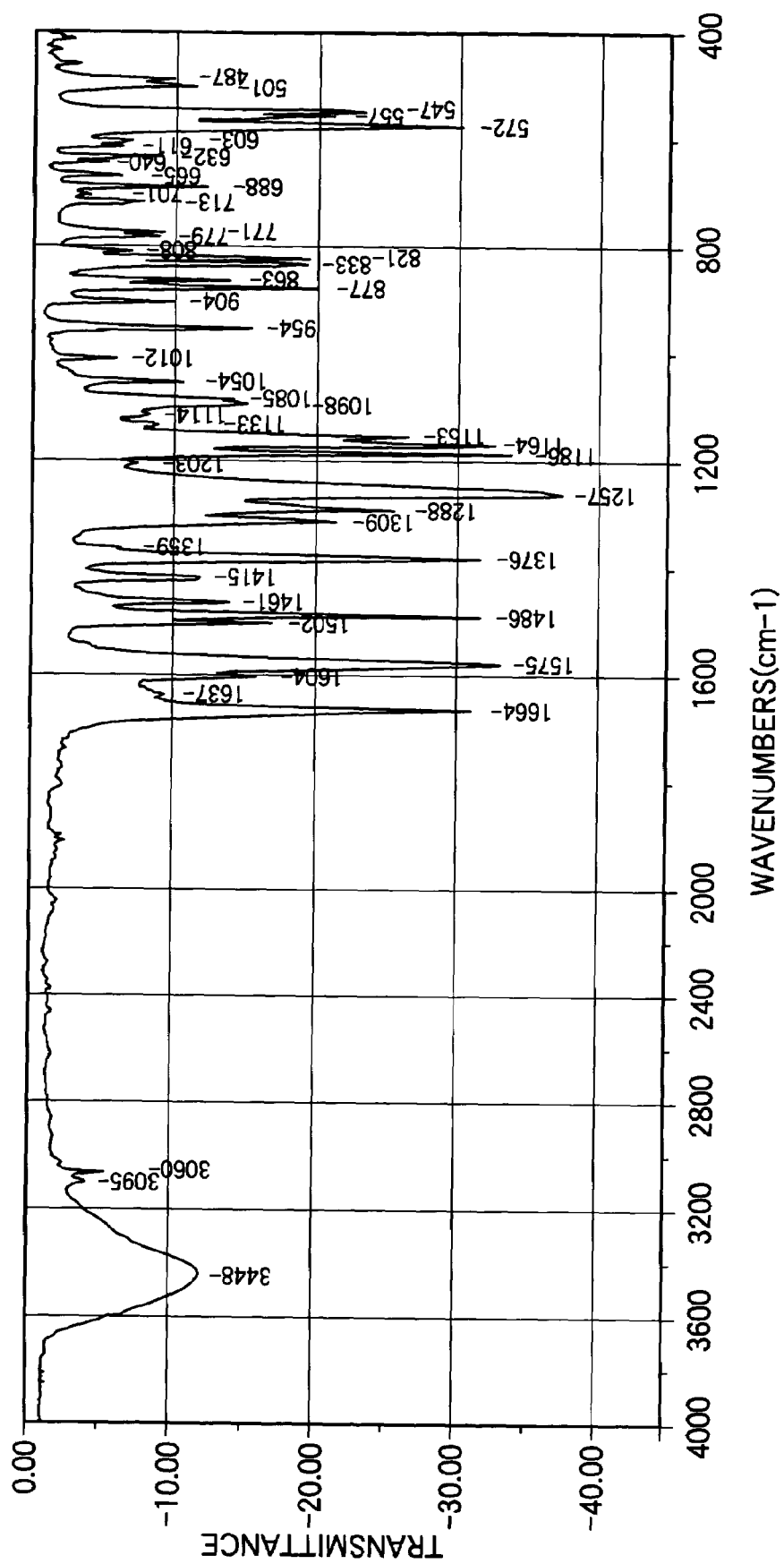
FIG. 4 is an IR spectrum of a white crystal prepared in Example 1 (2).
Figure 5:
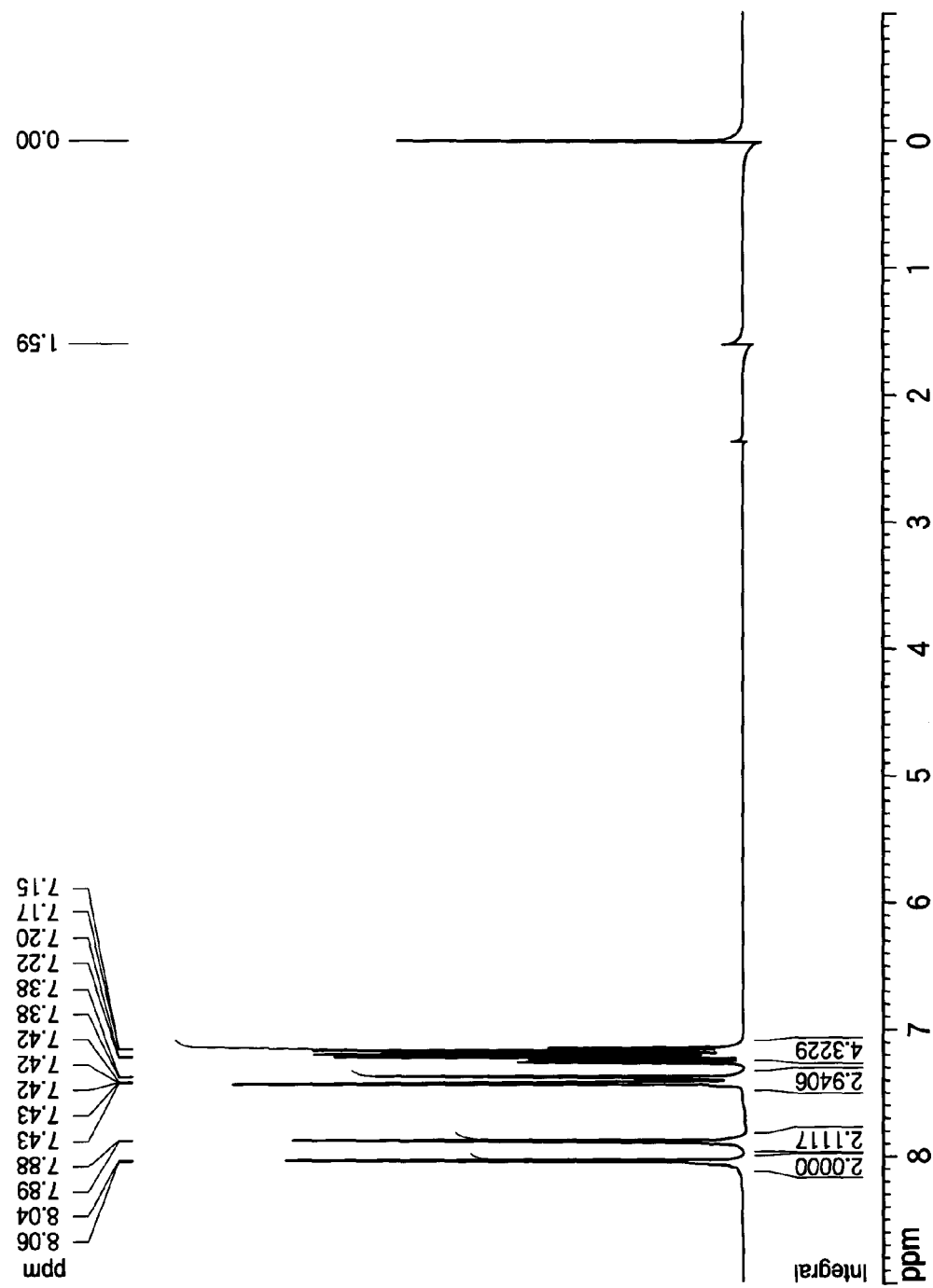
FIG. 5 is an NMR spectrum of a white crystal prepared in Example 1 (2).
Figure 6:
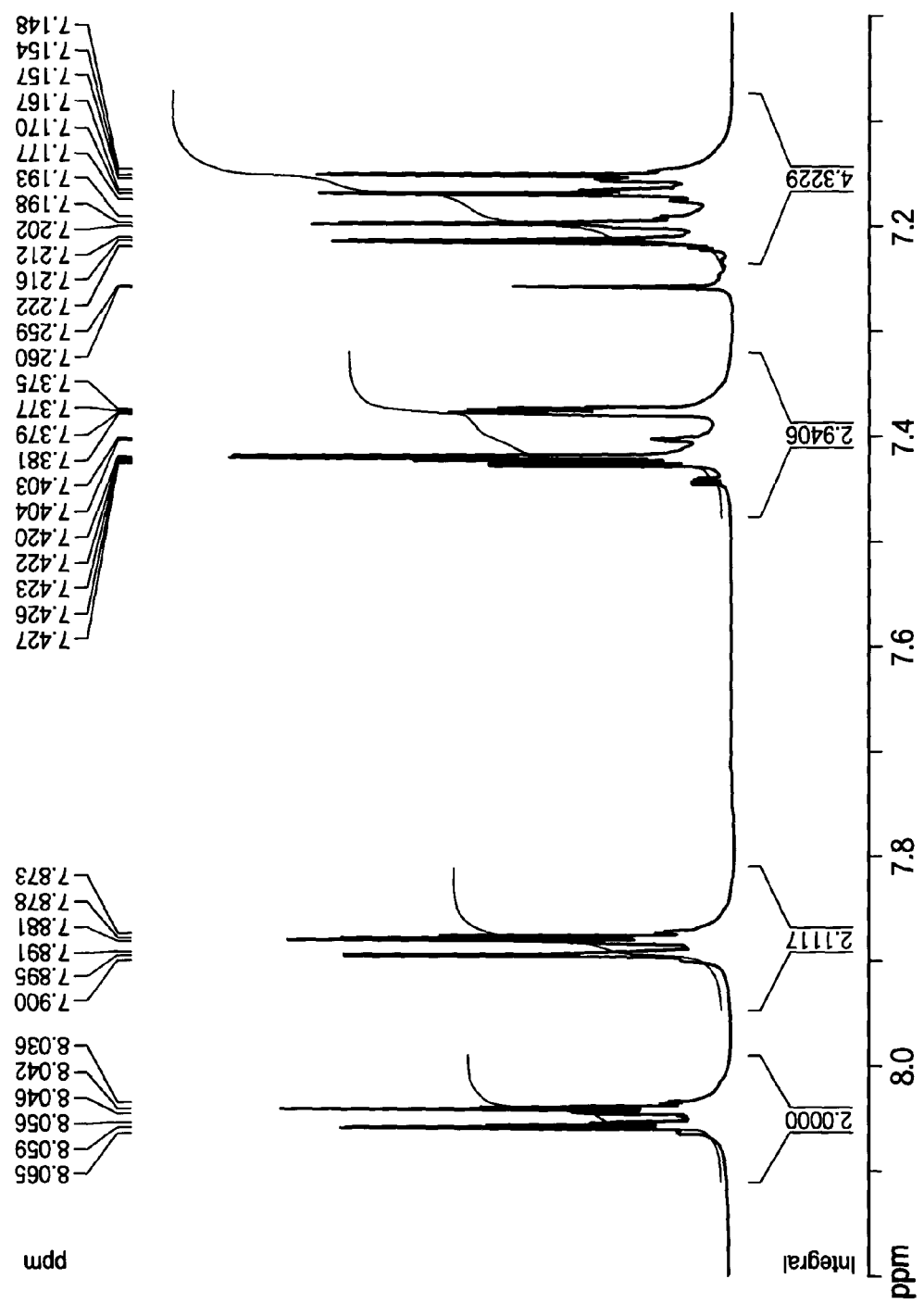
FIG. 6 is an NMR spectrum of a white crystal prepared in Example 1 (2).

To 215 g (about 400 mmol) of the crude crystal of A-SO₃Na, 300 mL of acetonitrile and 200 mL of sulfolane as a solvent were added, and further phosphoryl trichloride (245.3 g, 1.6 mole) was added and then reacted at 70° C. to obtain a reaction mixture. Further, 5 mL of N,N-dimethyl acetoamide was added thereto and the resulting yellow suspension was stirred at 71 to 73° C. for 40 min and then cooled to 3° C. To the suspension, 1 L of cool water was added at a rate such that the temperature of the reaction system was not over 10° C. The resulting precipitate was collected, washed with cool water and re-crystallized with 350 mL of toluene to obtain 153 g of the aimed white crystalline A-SO₂Cl having a melting point of from 130.5 to 131.5° C. (yield: 87% on the basis of A). The IR spectrum is shown in FIG. 4 and the NMR spectrum is shown in FIGS. 5 and 6.

(3) Preparation of 4-[4-(2,5-dichlorobenzoyl)phenoxy]benzene sulfonic acid iso-butyl(A-SO₃iso-Bu)

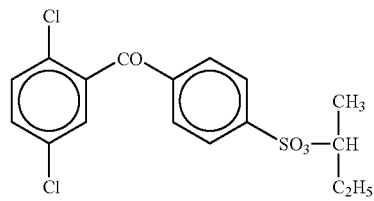

Figure 7:
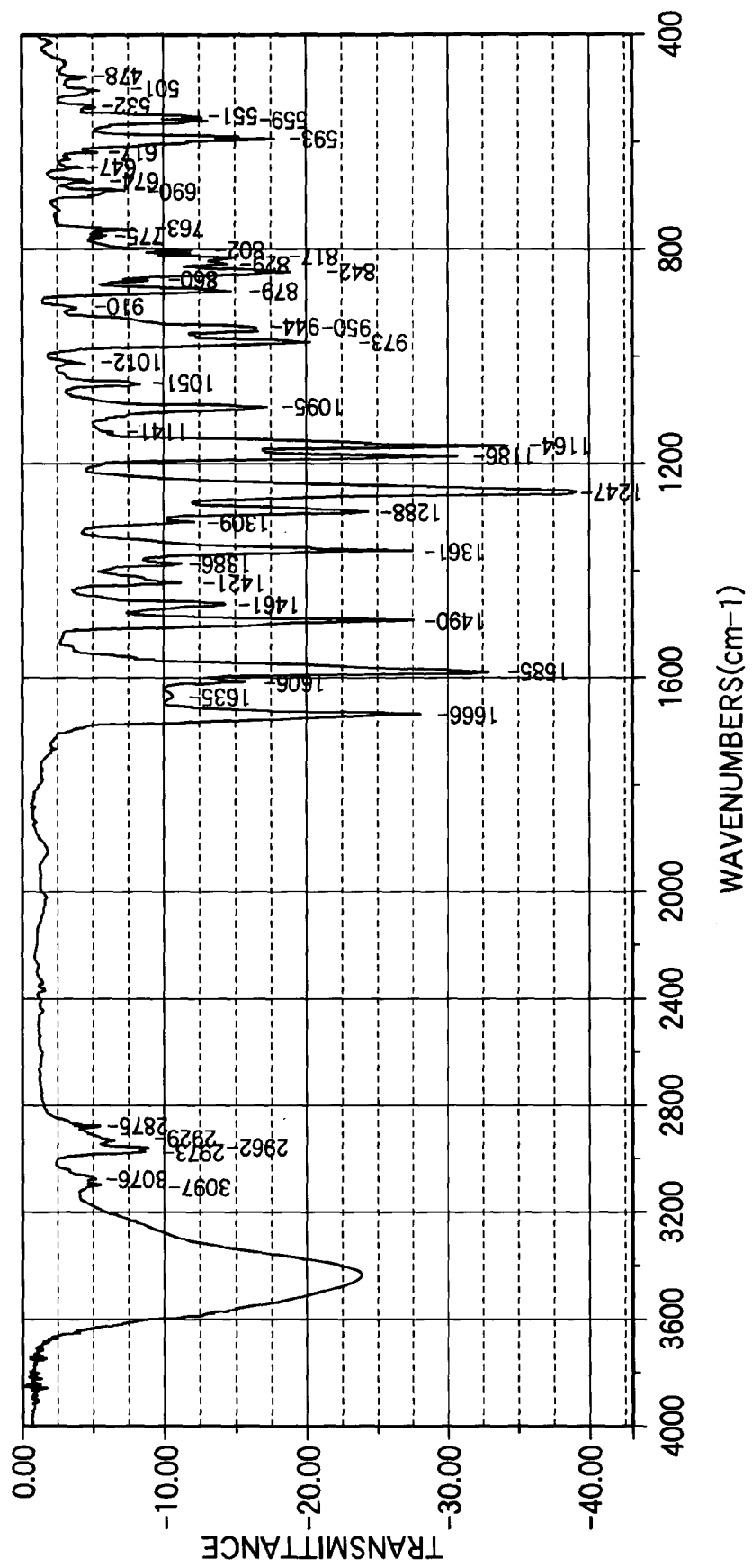
FIG. 7 is an IR spectrum of a white crystal prepared in Example 1 (3).
Figure 8:
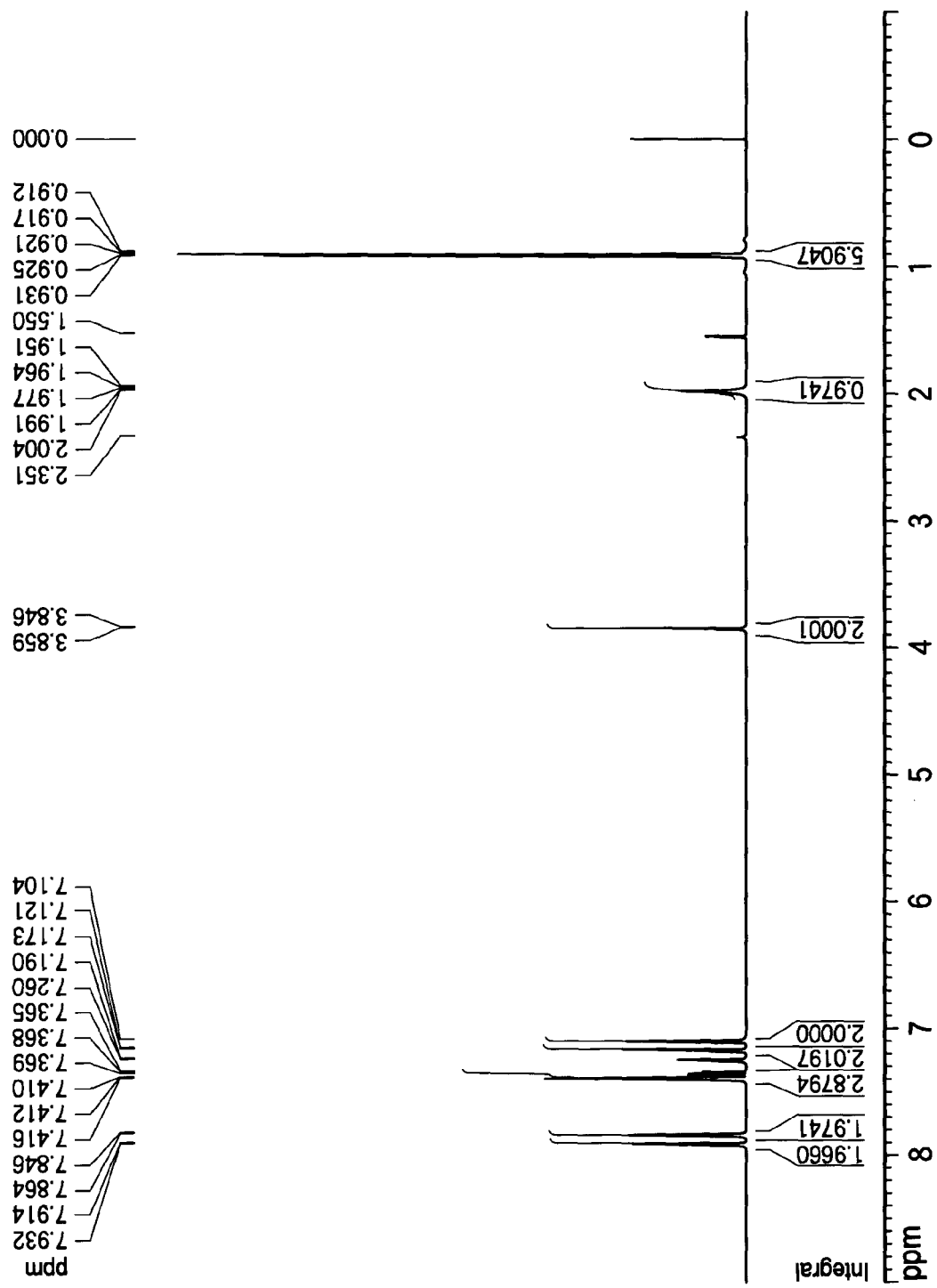
FIG. 8 is an NMR spectrum of a white crystal prepared in Example 1 (3).
Figure 9:
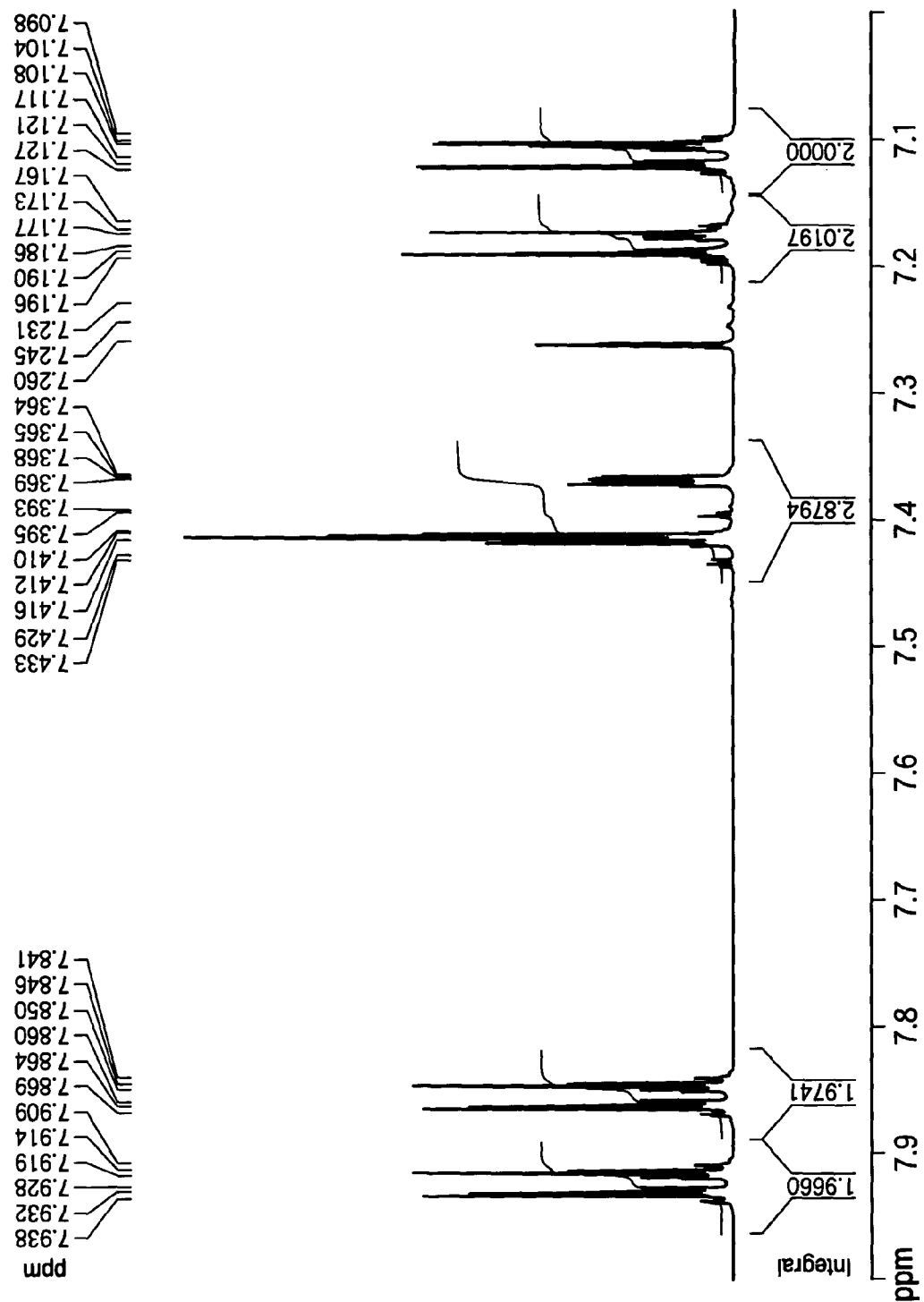
FIG. 9 is an NMR spectrum of a white crystal prepared in Example 1 (3).

22.09 g (50 mmol) of A-SO₂Cl was added dropwise into 2-methyl-1-propanol (4.0 g, 55 mmol) and 30 mL of pyridine with cooling by stirring mechanically over 40 min. As a result, a concentrated suspension was obtained and further the stirring was continued at 12 to 15° C. for additional 1 hr. 30 mL of concentrated hydrochloric acid and 100 g of ice water were added at once to the suspension. The suspension was stirred so that it became homogeneous gradually. Subsequently, the homogeneous suspension was quickly filtered with a Buchner funnel. A white viscous precipitate was recovered. The precipitate was re-dissolved in 300 mL of ethyl acetate and washed with water by a separating funnel. The resulting organic layer was dried with magnesium sulfate and the solvent was distilled off under reduced pressure. After concentration, a pale yellow oily liquid was dissolved in 30 mL of hot hexane and allowed to stand in a freezer for several days to obtain 16.67 g of the aimed white crystalline A-SO3i-Bu having a melting point of 73 to 74° C. in a yield of 70%. The IR spectrum is shown in FIG. 7 and the NMR spectrum is shown in FIGS. 8 and 9.

Example 2

Preparation of 4-[4-(2,5-dichlorobenzoyl)phenoxy]benzene sulfonic acid neo-pentyl (A-SO₃neo-Pe)

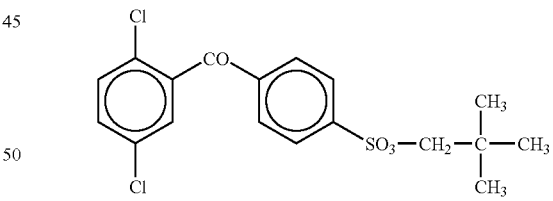

The same A-SO₂Cl (22.09 g 50 mmol) as prepared in Example 1 (2) was added dropwise to 2,2-dimethyl-1-propanol (4.85 g, 55 mmol) and 30 mL of pyridine with cooling under mechanically stirring over 40 min. As a result, a concentrated suspension was prepared and the stirring thereof was continued at 12 to 15° C. for additional 1 hr.

Figure 10:
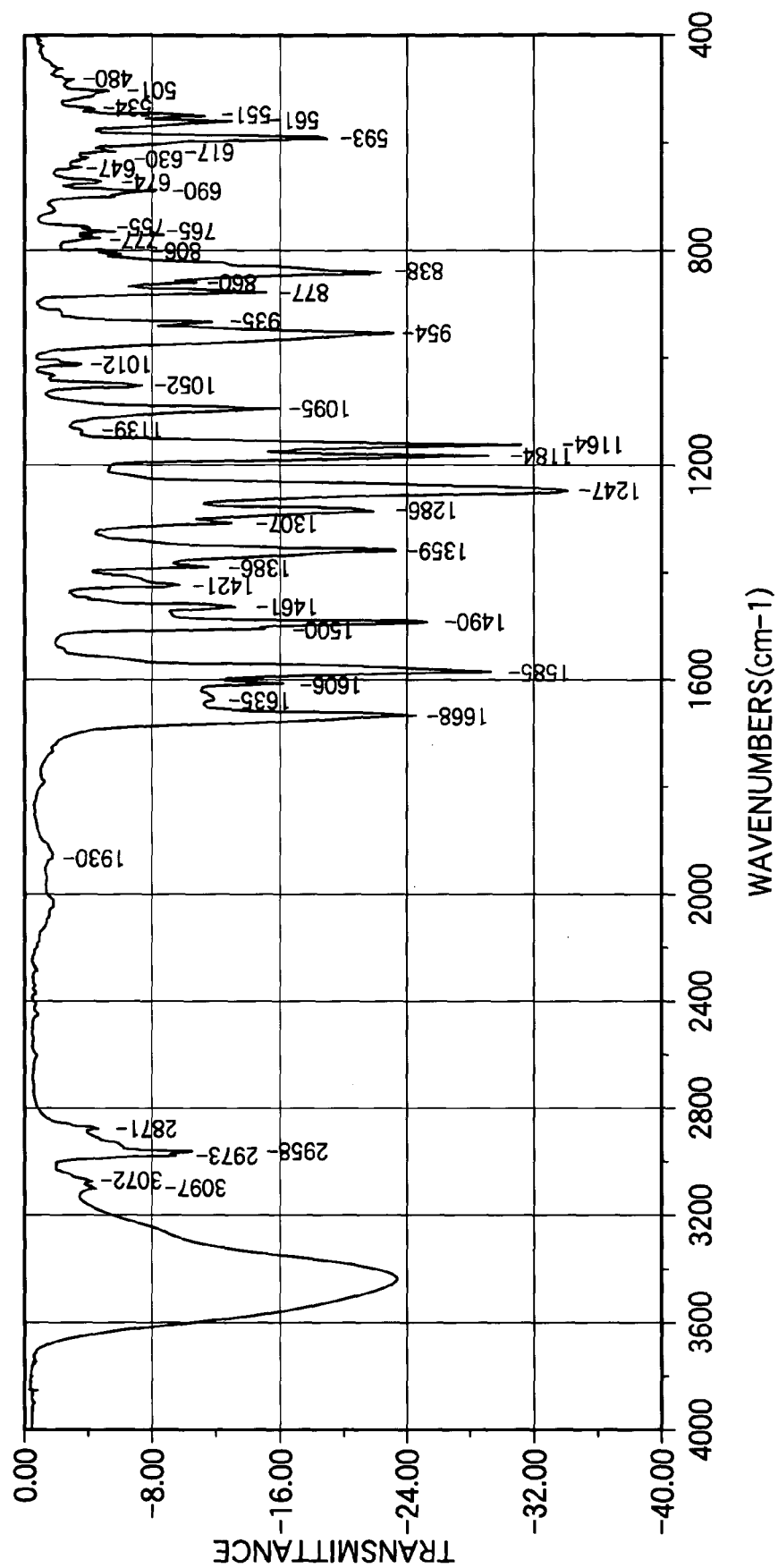
FIG. 10 is an IR spectrum of a white crystal prepared in Example 2.
Figure 11:
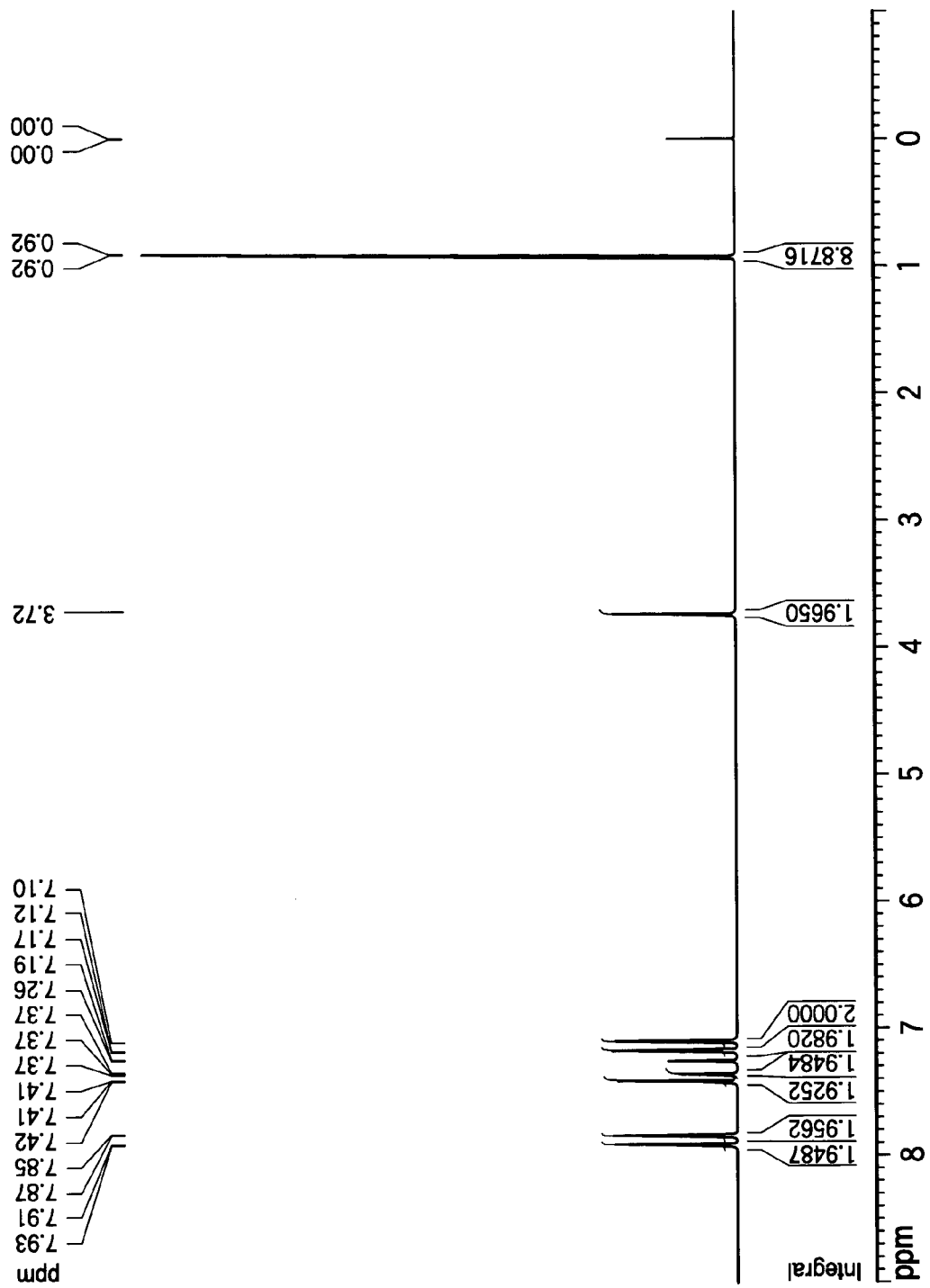
FIG. 11 is an NMR spectrum of a white crystal prepared in Example 2.
Figure 12:
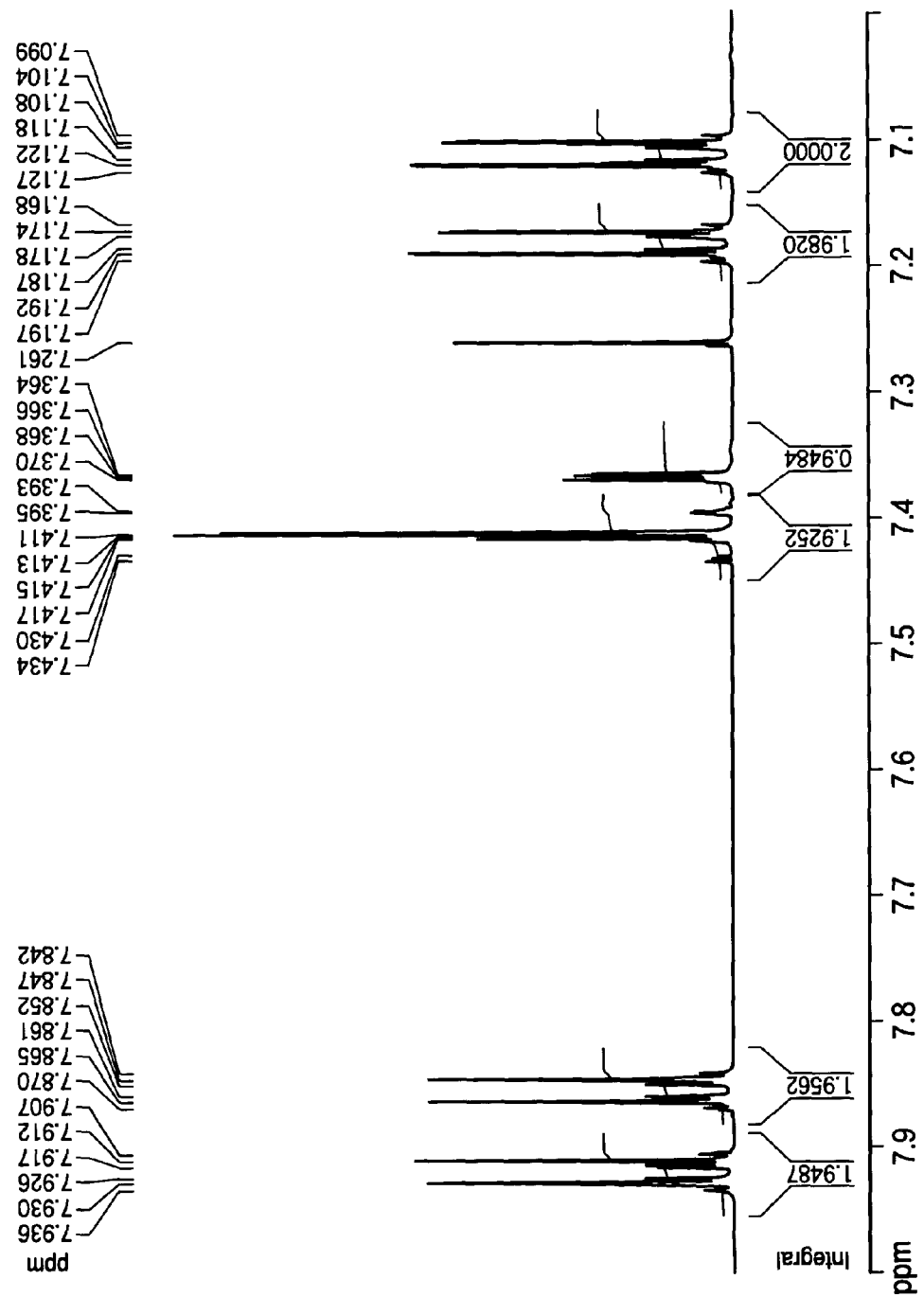
FIG. 12 is an NMR spectrum of a white crystal prepared in Example 2.

The suspension was allowed to react with 30 mL of concentrated hydrochloric acid and 100 g of ice to generate a precipitate. The precipitate was collected with filteration, washed with cool water and dried, and then was allowed to contact with 150 mL of boiling toluene. Insoluble components (the most thereof was a pyridinium salt of A-SO₃H) were removed with filtration and a filtrate was concentrated to prepare 40 mL of a concentrate. The concentrate was allowed to stand in a freezer to deposit a white crystalline A-SO₃neo-Pe (the meting point: 112.0 to 112.5° C). The amount was 16.92 g and the yield was 69%. The IR spectrum is shown in FIG. 10 and the NMR spectrum is shown in FIGS. 11 and 12.

Synthesis Example 1

Preparation of Oligomer (Reffered to as "BCPAF Oligomer")

To a 1 L three-necked flask equipped with a stirrer, a thermometer, a cooling tube, a Dean-Stark tube, and three-way cock for introducing nitrogen, 67.3 g (0.20 mol) of 2,2-bis(4-hydroxyphenyl)-1,1,1,3,3,3-hexafluoropropane (bisphenol AF), 60.3 g (0.24 mol) of 4,4'-dichlorobenzophenone (4,4'-DCBP), 71.9 g (0.52 mol) of potassium carbonate, 300 mL of N,N-dimethyl acetoamide (DMAc) and 150 mL of toluene were introduced and reacted in a nitrogen atmosphere with heat at 130° C. while stirring in an oil bath. The reaction was conducted while water generated from the reaction was subjected to azeotropy with toluene to remove through a Dean-Stark tube from the system. After the about 3 hr reaction, generation of water was not observed mostly. Thereafter, while the reaction temperature was gradually elevated until 150° C., the most of toluene was removed, and the reaction was continued at 150° C. for 10 hr. After the 10 hr reaction, 10.0 g (0.040 mol) of 4,4'-DCBP was added and the reaction was continued for additional 5 hr. The resulting reaction solution was allowed to stand for cooling and then a precipitated inorganic compound generated as a byproduct was removed with filtration, and the filtrate was introduced into 4 L of methanol. The precipitated product was recovered with filtration, dried and dissolved in 300 mL of tetrahydrofurane. The solution was re-precipitated in 4 L of methanol to obtain 95 g of the aimed polymer (yield: 85%).

The resultant polymer had a weight average molecular weight in terms of polystyrene, as determined by GPC(THF solvent), of 12,500. Further, the polymer was soluble in THF, NMP, DMAc and sulfolane and had Tg of 110° C. and a thermal decomposition temperature of 498° C.

The resultant polymer was an oligomer represented by the following formula (I) (hereinafter referred to as "BCPAF oligomer").

Synthesis Example 2

Preparation of Oligomer (Referred to as "BCPFL Oligomer")

The procedure of Synthesis Example 1 was repeated except that 80.6 g (0.23 mole) of 9,9-bis(4-hydroxyphenyl)fluorine (FLBP) was used instead of 67.3 g (0.20 mole) of 2,2-bis(4-hydroxyphenyl)-1,1,1,3,3,3-hexafluoropropane (bisphenol AF) and NMP was used as a solvent instead of DMAc to conduct the reaction and post-treatment. As a result, 103 g of the aimed polymer was obtained. (yield: 83%).

The resultant polymer had a weight average molecular weight in terms of polystyrene, as determined by GPC(THF solvent), of 12,300. Further, the polymer was soluble in THF, NMP and DMI and had Tg of 175° C. and a thermal decomposition temperature of 524° C.

The resultant polymer was an oligomer represented by the following formula (II) (hereinafter referred to as "BCPFL Oligomer").

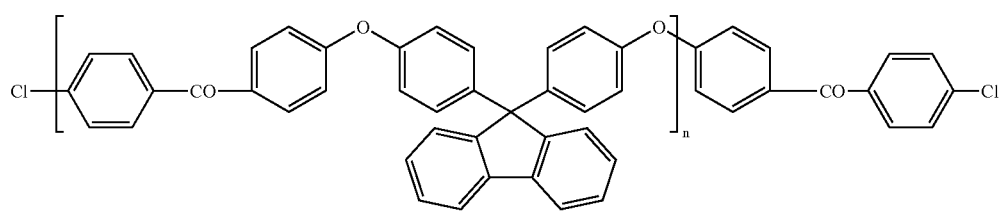

(II)

Polymerization of Polyarylene

Example 3

Preparation of Polyarylene having an -Butyl Group as a Protecting Group (PolyAB—SO₃i-Bu)

Dried N-methyl pyrrolidone (NMP) in an amount of 60 mL was added to a mixture of 15.34 g (32 mmol) of ASO₃i-butyl prepared in Example 1, 10.52 g (1.33 mmol) of BCPAF Oligomer obtained in Synthesis Example 1, 0.65 g (1 mmol) of Ni(PPh₃)₂Cl₂, 33.50 g (13.33 mmol) of PPh, 0.65 g (4.83 mmol) of NaI and 5.45 g (83.33 mmol) of zinc dust in a nitrogen atmosphere.

The reaction mixture was heated with stirring (finally heated to 74° C.) and reacted for 3 hr. During the reaction, the rise of viscosity in the reaction solution was observed. The polymerization reaction solution was diluted with 250 mL of THF, stirred for 30 min, and filtered using Celite (TM John-Manville) as a filtering assistant. The filtrate was poured in a large excess amount of 1500 mL of methanol and thereby coagulated. The resultant coagulum was collected

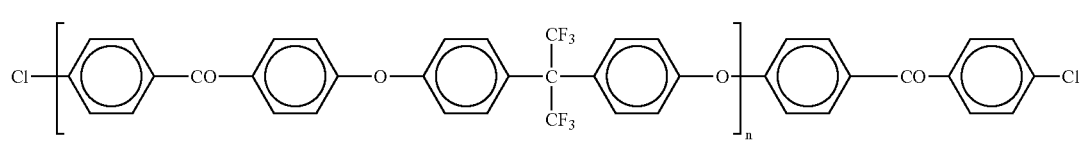

(I)

with filtration and air-dried, and further re-dissolved in THF/NMP (200 mL/30 mL) and coagulated and deposited by a large excess amount of 1500 mL of methanol. The thus treated coagulum was air-dried and then dried with heat to obtain 20.54 g of the aimed yellow flake-like polymer of a sulfonic acid derivative protected with I-butyl group (PolyAB—$SO_3$i-Bu) (yield: 78%).

Figure 13:
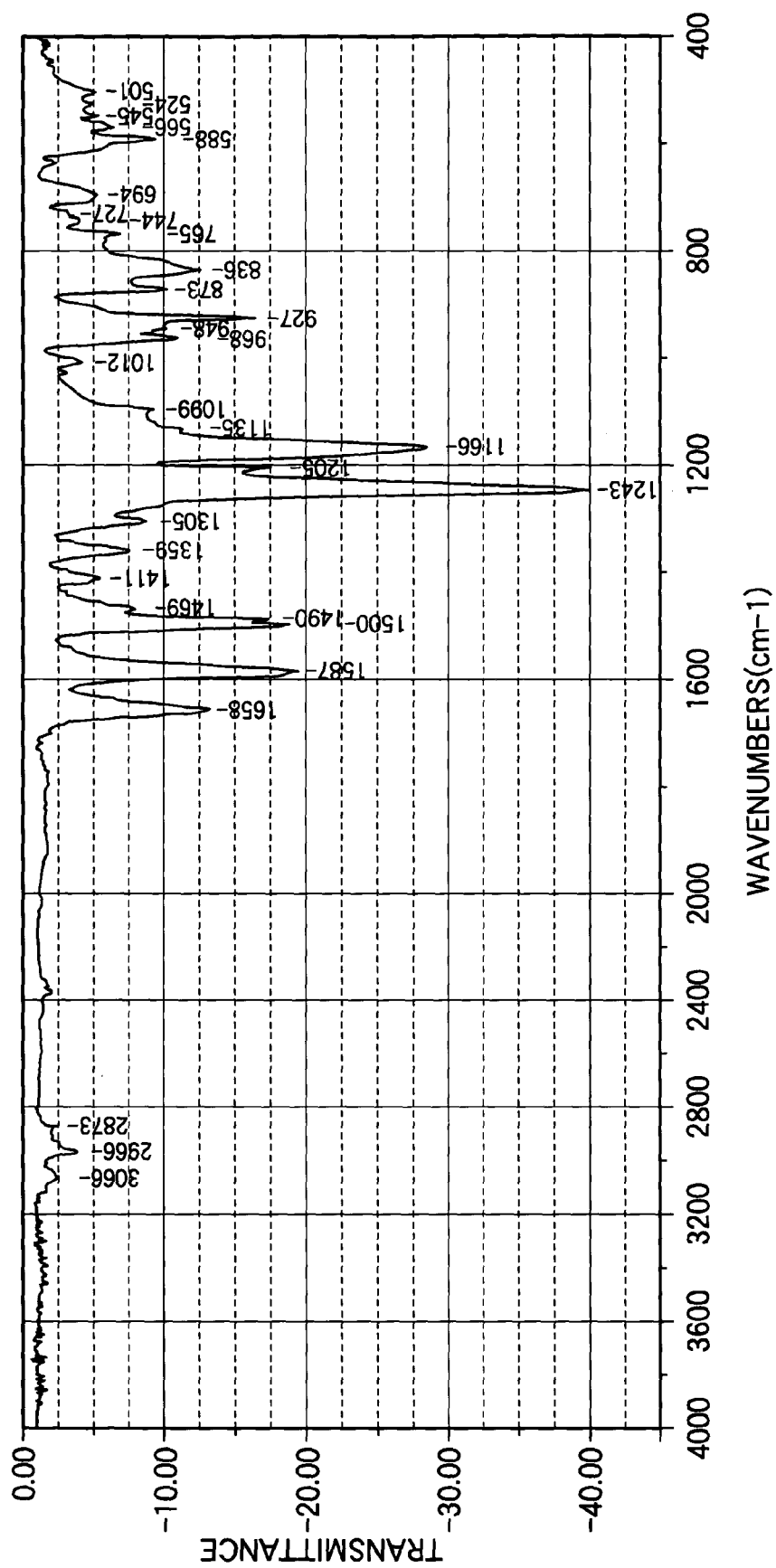
FIG. 13 is an IR spectrum of polyarylene prepared in Example 3.
Figure 14:
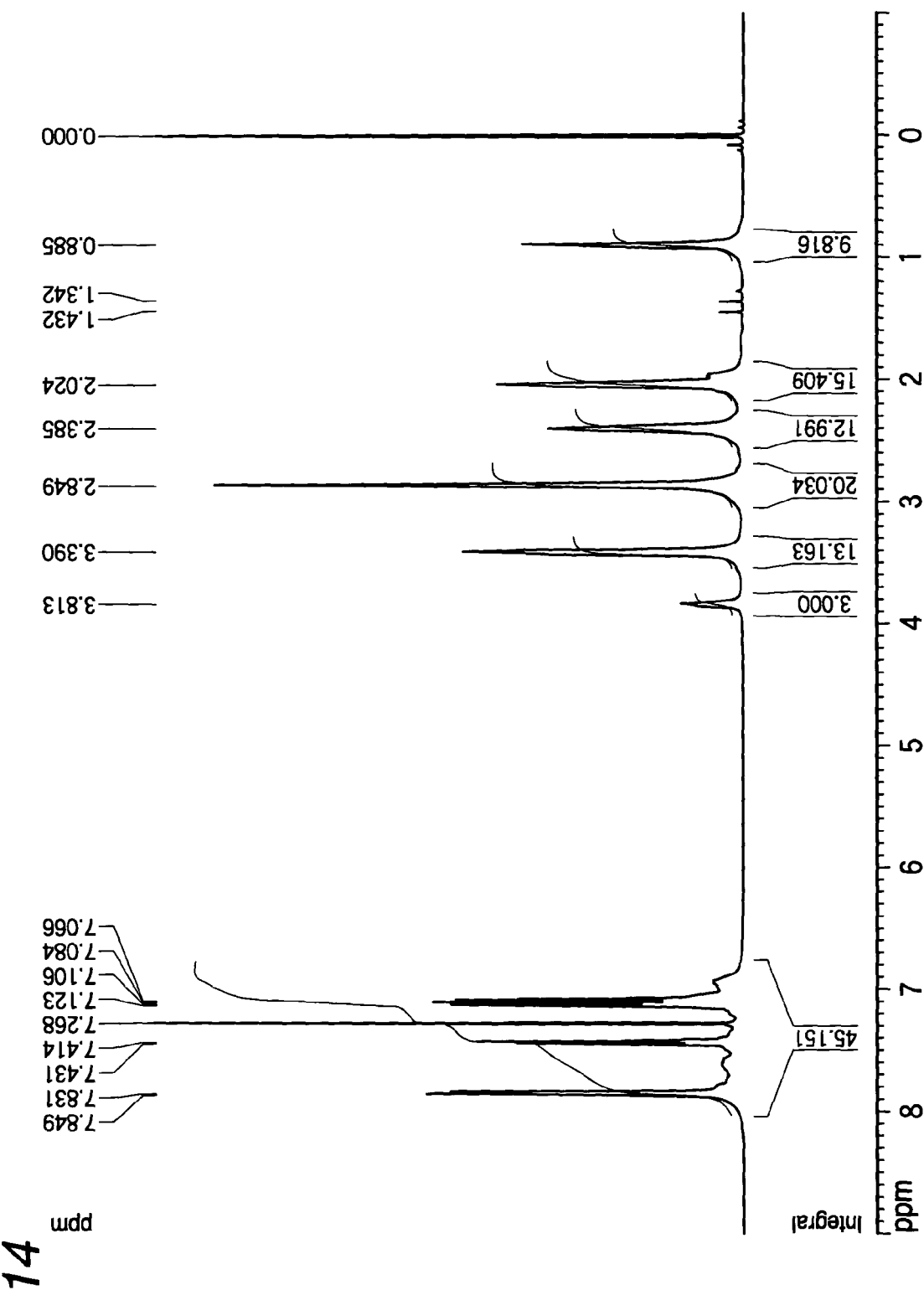
FIG. 14 is an NMR spectrum of polyarylene prepared in Example 3.

The resultant polymer had a number average molecular weight in terms of polystyrene, as determined by GPC(THF solvent), of 13,200 and a weight average molecular weight of 33,300. The IR spectrum is shown in FIG. 13 and the NMR spectrum is shown in FIG. 14.

Example 4

Preparation of Polyarylene having a Neo-pentyl Group as a Protecting Group (PolyAB—$SO_3$neo-Pe)

Using 39.46 g (98.33 mmol) of A-$SO_3$neo-Pe prepared in Example 2, 18.70 g (0.167 mmol) of BCPAF Oligomer prepared in Synthesis Example 1, 1.96 g (0.30 mmol) of Ni(PPh$_3$)$_2$Cl$_2$, 10.49 g (4.00 mmol) of PPh$_3$, 0.45 g (0.30 mmol) of NaI, 15.69 g (24.00 mmol) of zinc dust and 129 mL of dried NMP, the polymerization reaction was carried out in the same procedure as in Example 3. After 60 min from the beginnings of the polymerization reaction, the rise of viscosity in the reaction solution was observed. The polymerization reaction was continued with stirring for 3 hr. Thereafter, the polymerization reaction solution was diluted with THF, and subjected to post-treatment. As a result, 47.0 g of the aimed yellow fibrous copolymer of a sulfonic acid derivative protected with neo-pentyl group (PolyAB—$SO_3$neo-Pe) was obtained. (yield: 92%)

Figure 15:
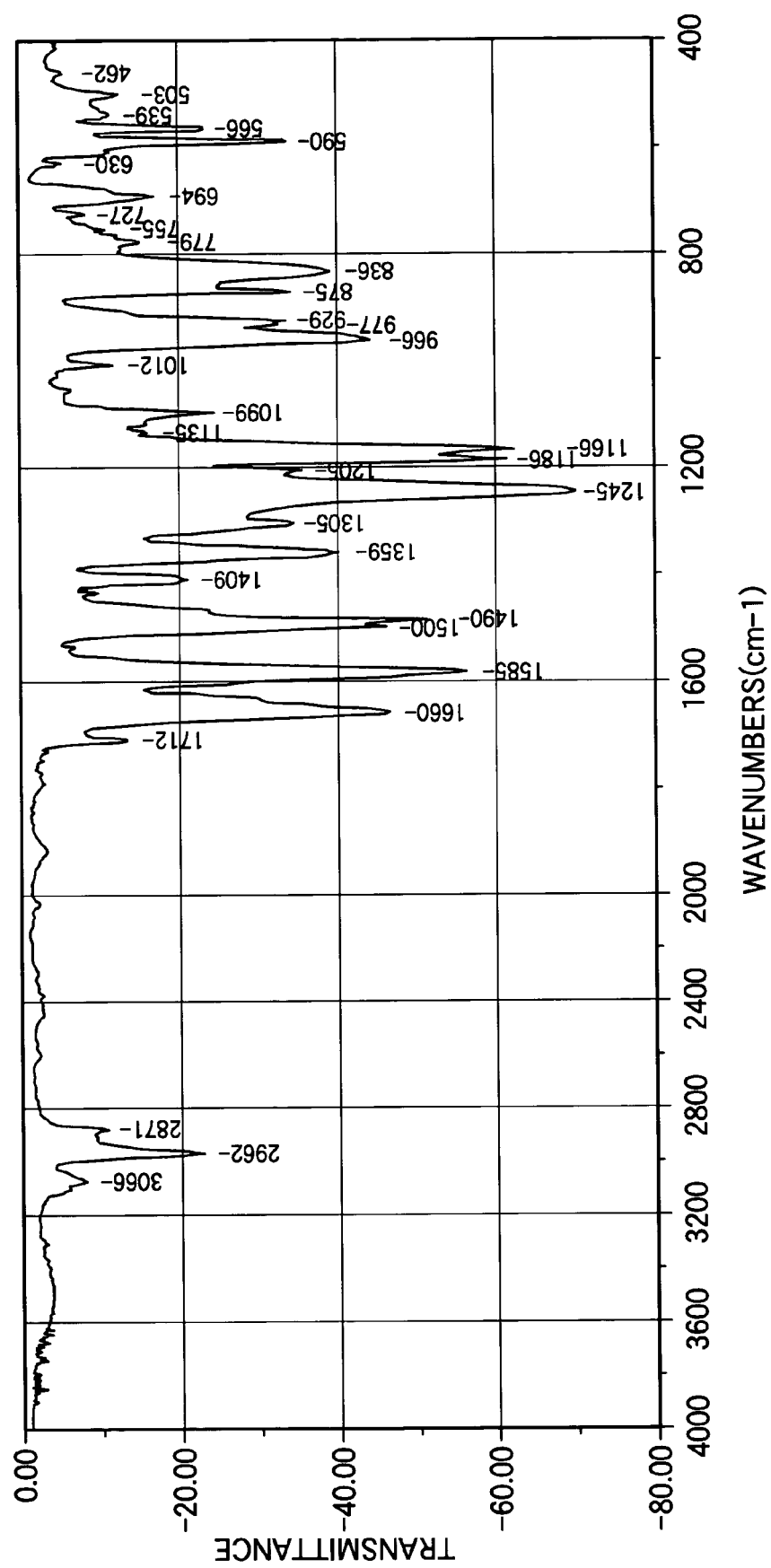
FIG. 15 is an IR spectrum of polyarylene prepared in Example 4.
Figure 16:
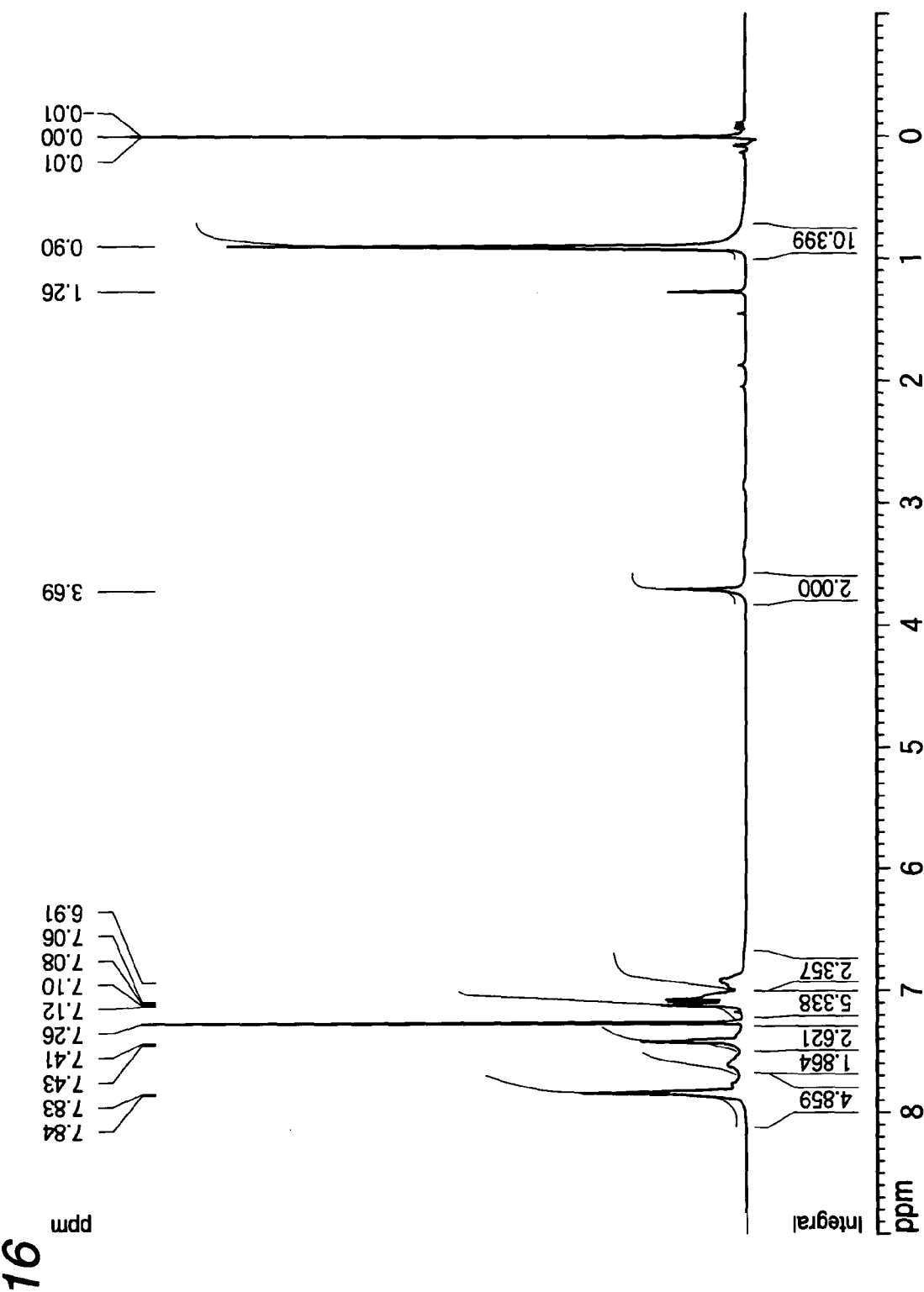
FIG. 16 is an NMR spectrum of polyarylene prepared in Example 4.
Figure 17:
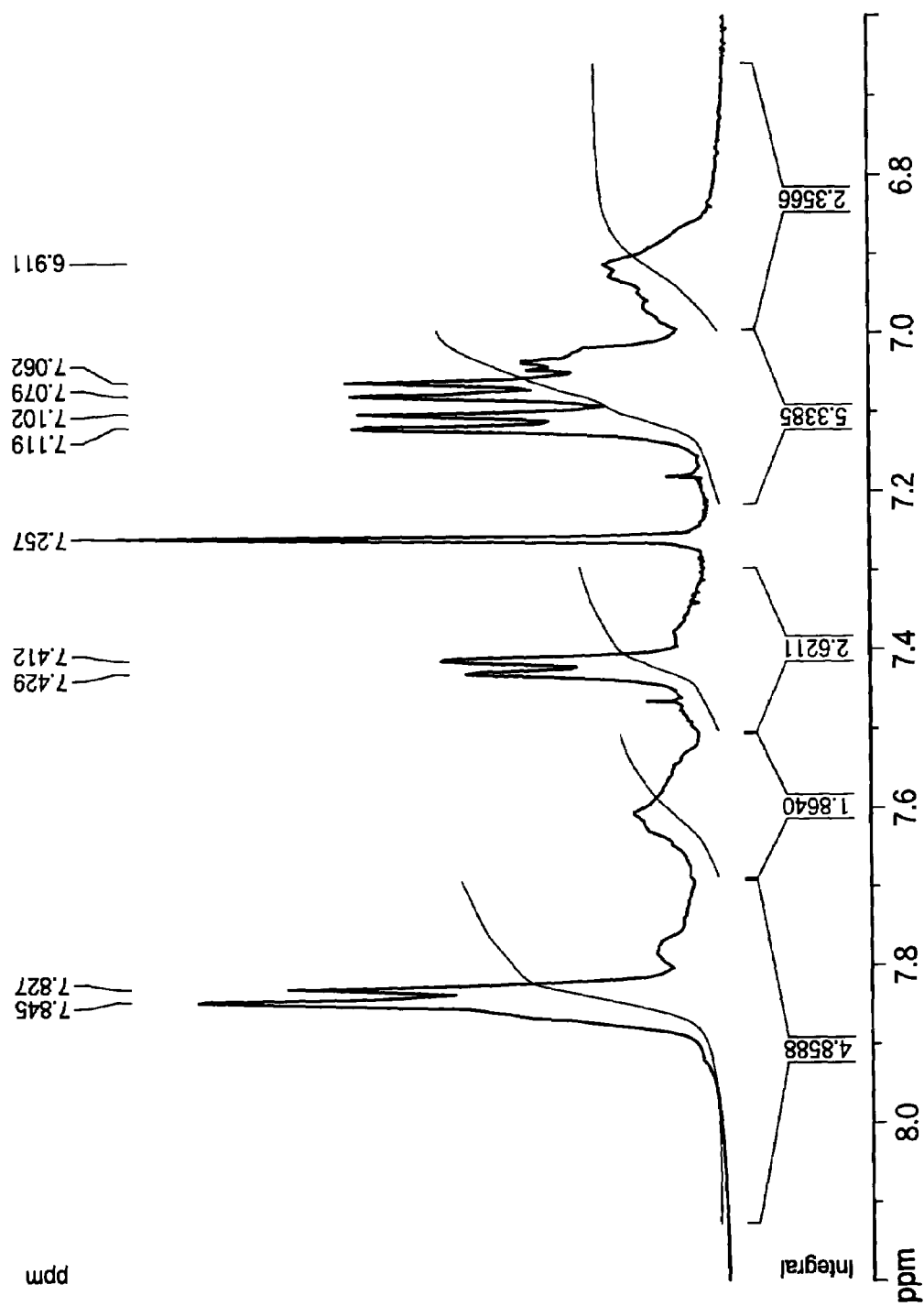
FIG. 17 is an NMR spectrum of polyarylene prepared in Example 4.

The resultant polymer had a number average molecular weight in terms of polystyrene, as determined by GPC(THF solvent), of 53,700 and a weight average molecular weight of 187,000. The IR spectrum is shown in FIG. 15 and the NMR spectrum is shown in FIGS. 16 and 17.

Example 5

Preparation of Polyarylene having a Neo-pentyl Group as a Protecting Group (PolyAB—$SO_3$neo-Pe)

Using 7.62 g (0.62 mmol) of BCPFL oligomer prepared in Synthesis Example 2 instead of 4.88 g (0.62 mmol) of BCPAF oligomer used in Example 4, and further 17.81 g (44.38 mmol) of A-$SO_3$neo-Pe prepared in Example 2, 0.88 g (1.35 mmol) of Ni(PPh$_3$)$_2$Cl$_2$, 4.72 g (18.00 mmol) of PPh$_3$, 0.20 g (1.35 mmol) of NaI, 7.06 g (108.00 mmol) of zinc dust and 60 mL of dried NMP, the polymerization reaction and the post-treatment were carried out in the same procedure as in Example 4.

As a result, 21.00 g of the aimed yellow fibrous copolymer of a sulfonic acid derivative protected with neo-pentyl group (PolyAB—$SO_3$neo-Pe) was obtained (yield: 77%).

Figure 18:
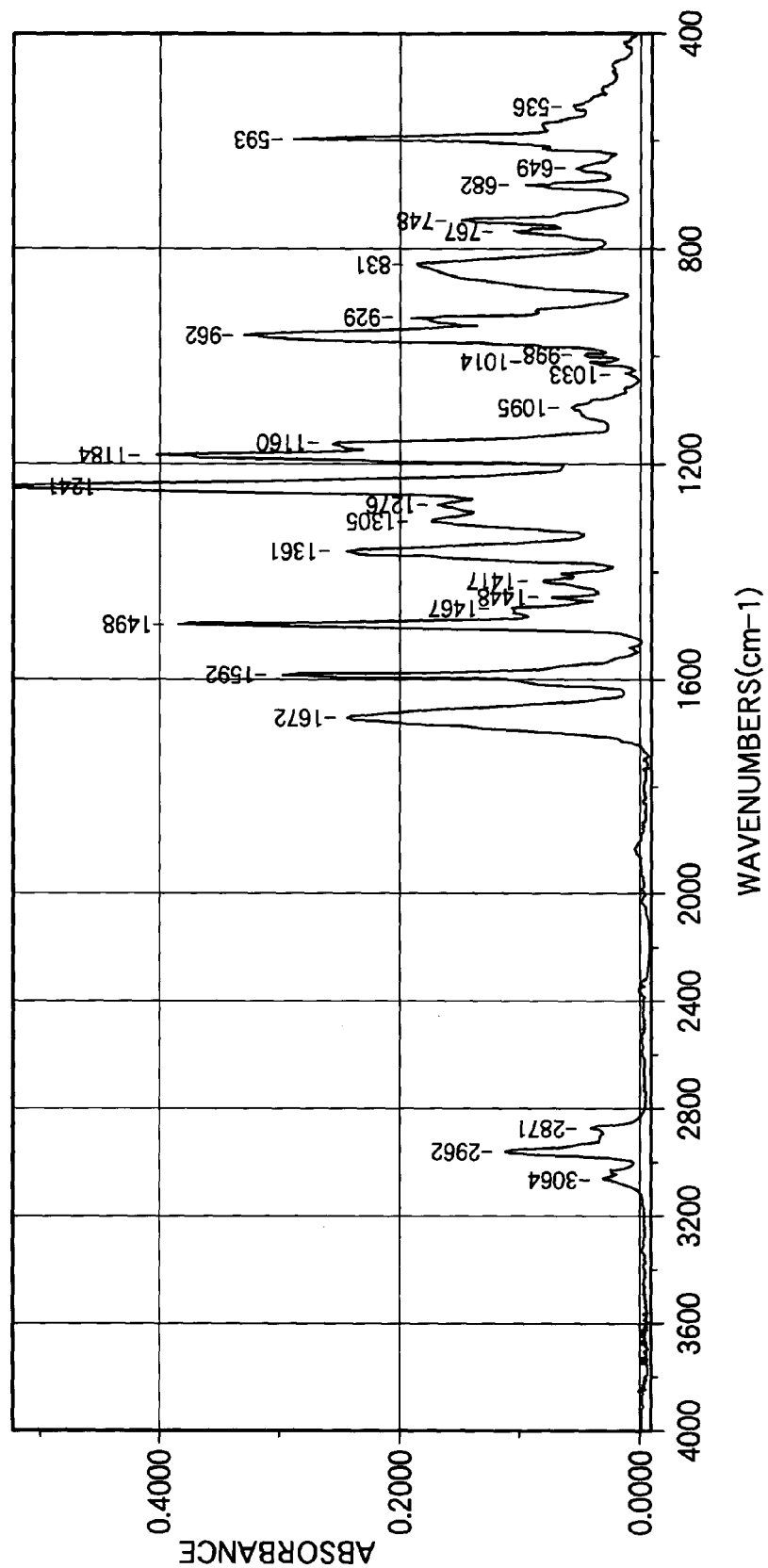
FIG. 18 is an NMR spectrum of polyarylene prepared in Example 5.

The resultant polymer had a number average molecular weight in terms of polystyrene, as determined by GPC(THF solvent), of 22,100 and a weight average molecular weight of 90,800. The IR spectrum is shown in FIG. 18.

Conversion to Polyarylene Having a Sulfonic Acid Group with Hydrolysis

Example 6

Conversion of Polyarylene having an i-Butyl Group as a Protecting Group (PolyAB—$SO_3$i-Bu) into Polyarylene having a Sulfonic Acid Group (PolyAB—$SO_3$H)

PolyAB—$SO_3$i-Bu prepared in Example 3 in an amount of 5.08 g (2.7 mmol based on $SO_3$i-Bu) was dissolved in 60 mL of NMP and heated to 90° C. To the reaction solution, a mixture of 50 mL of methanol and 8 mL of concentrated hydrochloric acid was added at once. The reaction was carried out in a suspension state in a mild refluxing condition for 10 hr. A distillation apparatus was set and an excess amount of methanol was distilled off and thereby a pale green colored transparent solution was obtained. The solution was cast on a glass plate to form a film. After the film formation, the film was immersed in water for 3 days, air-dried and vacuum-dried to obtain the film having a dried thickness of 50 μm. It was defined from IR spectrum and quantitative analysis of ion exchange volume that sulfonic acid ester group (—$SO_3$R) was quantitatively converted to sulfonic acid group (—$SO_3$H).

Figure 19:
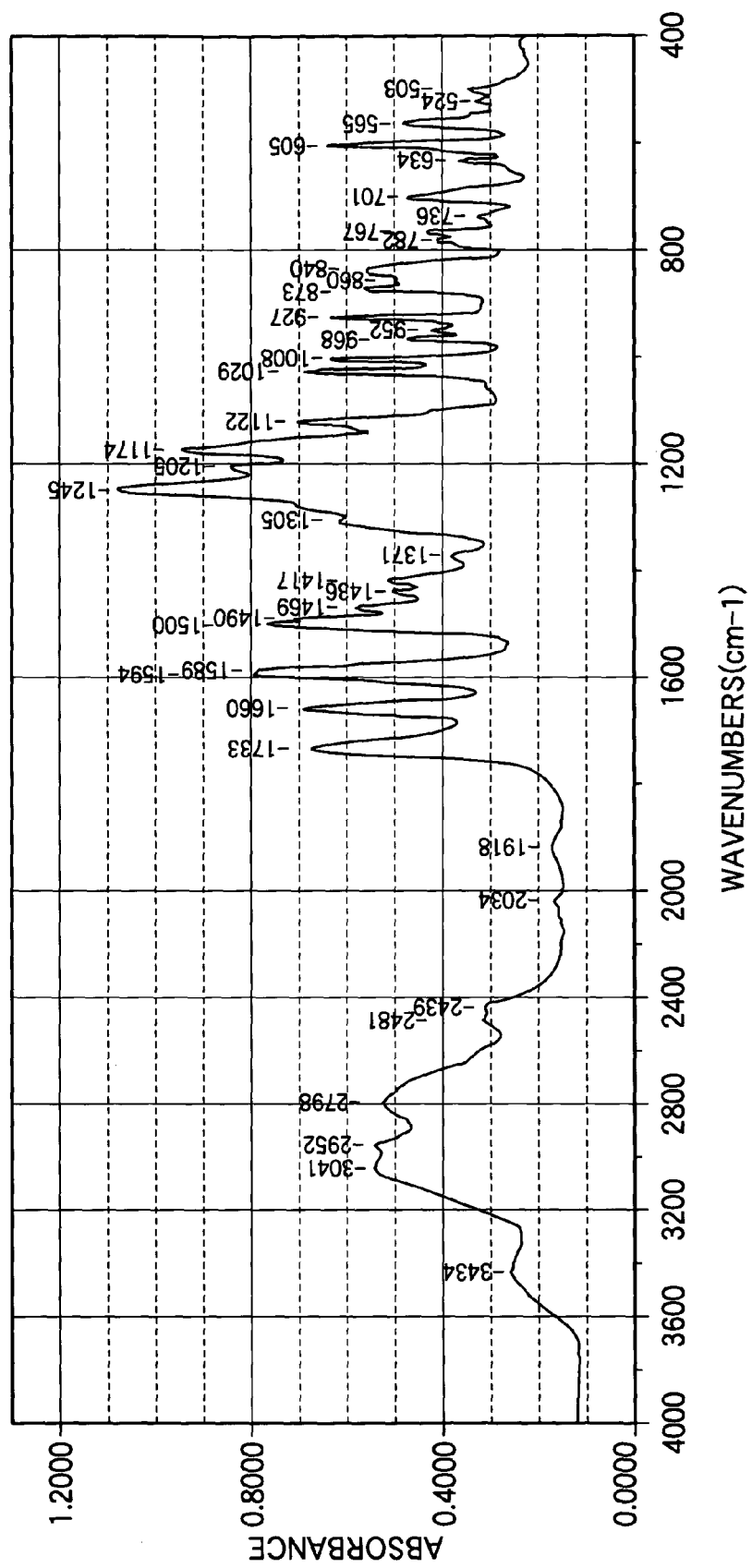
FIG. 19 is an IR spectrum of polyarylene having a sulfonic acid group prepared in Example 6.
Figure 20:
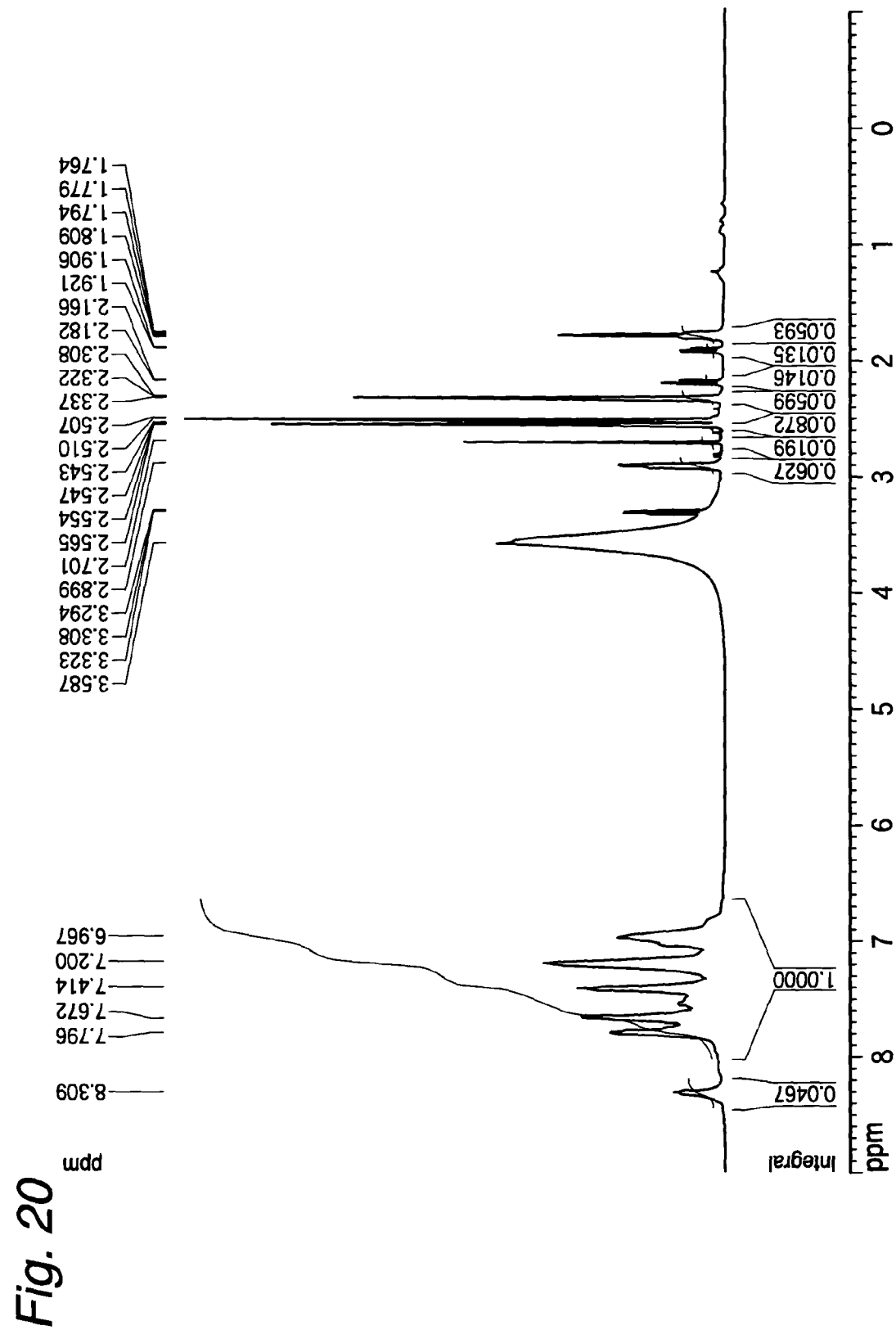
FIG. 20 is an NMR spectrum of polyarylene having a sulfonic acid group prepared in Example 6.

The IR spectrum is shown in FIG. 19 and the NMR spectrum is shown in FIG. 20. The sulfonic acid group-containing polyarylene had a sulfonic acid group content of 1.46 meq/g (the sulfonic acid group content of the monomer prepared in polymerization was 1.47 meq/g).

Example 7

Conversion of Polyarylene having Neo-Pentyl Group as a Protecting Group for Sulfonic Acid (PolyAB—$SO_3$neo-Pe) into Polyarylene having a Sulfonic Acid Group (PolyAB—$SO_3$H)

PolyAB—$SO_3$neo-Pe in an amount of 4.50 g (8 mmol based on $SO_3$neo-Pe) was gradually added to 35 mL of trifluoro acetic acid. The resulting viscous solution was heated to be in a mild refluxing state. During the reaction, 5 mL of trifluoro acetic acid was further added. After 2 hr, a polymer was precipitated, and further the stirring was continued and the reaction was carried out for 4 hr in total. After the reaction, the reaction mixture was left until it became room temperature. The precipitate was collected with filtration as an aggregate. The aggregate was suspended in 400 mL of THF with stirring and washed, and then, the aggregate was collected with filtration and air-dried to obtain a crude product. The crude product was washed with water twice and finally a pale brown powdery polymer was obtained.

A 8% by weight NMP solution of the polymer obtained was cast on a glass plate to form a film. After the film formation, the film was air-dried and vacuum-dried to obtain the film having a dried thickness of 40 μm. It was defined from IR spectrum and quantitative analysis of ion exchange capacity that sulfonic acid ester group (—$SO_3$R) was quantitatively converted to sulfonic acid group (—$SO_3$H).

Figure 21:
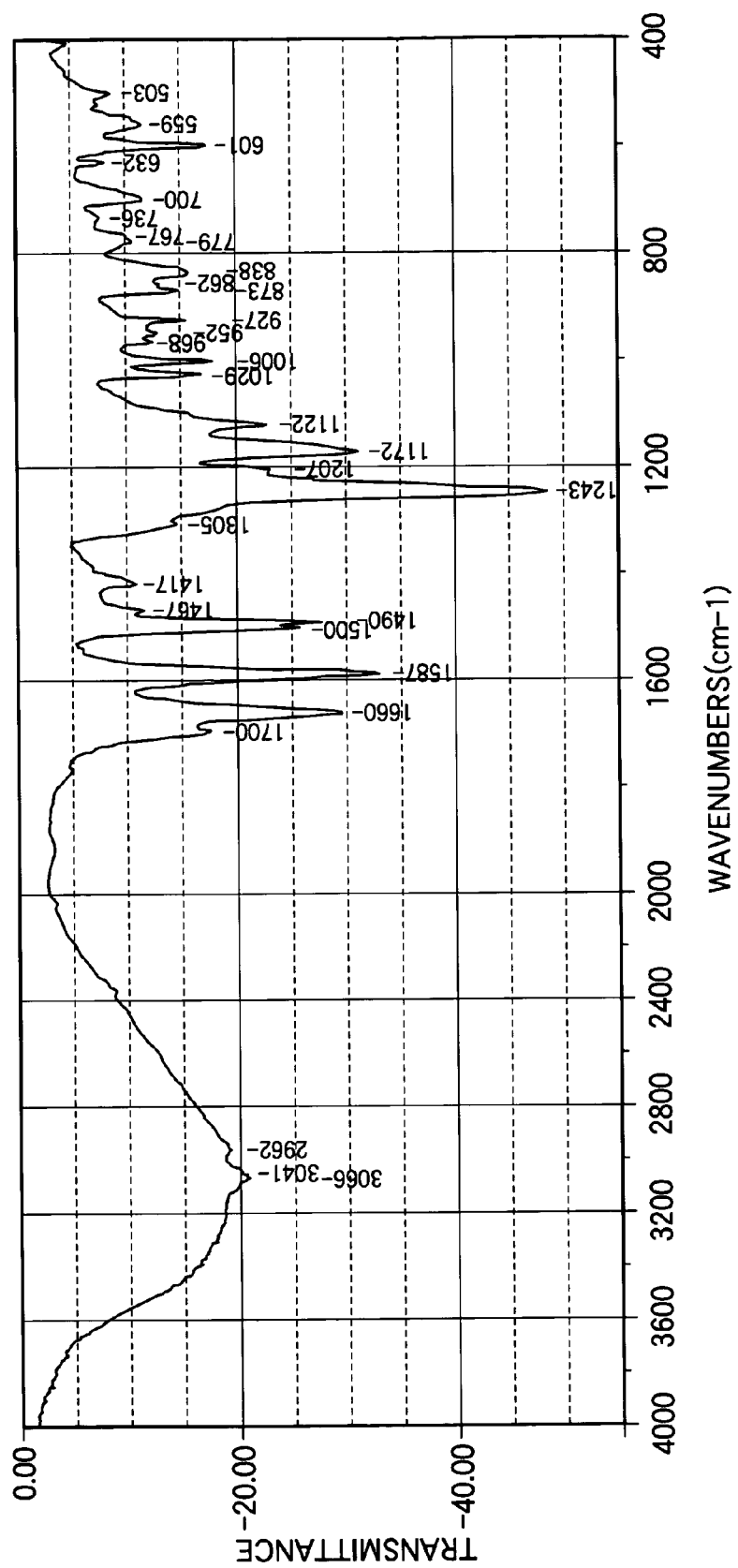
FIG. 21 is an IR spectrum of polyarylene having a sulfonic acid group prepared in Example 7.
Figure 22:
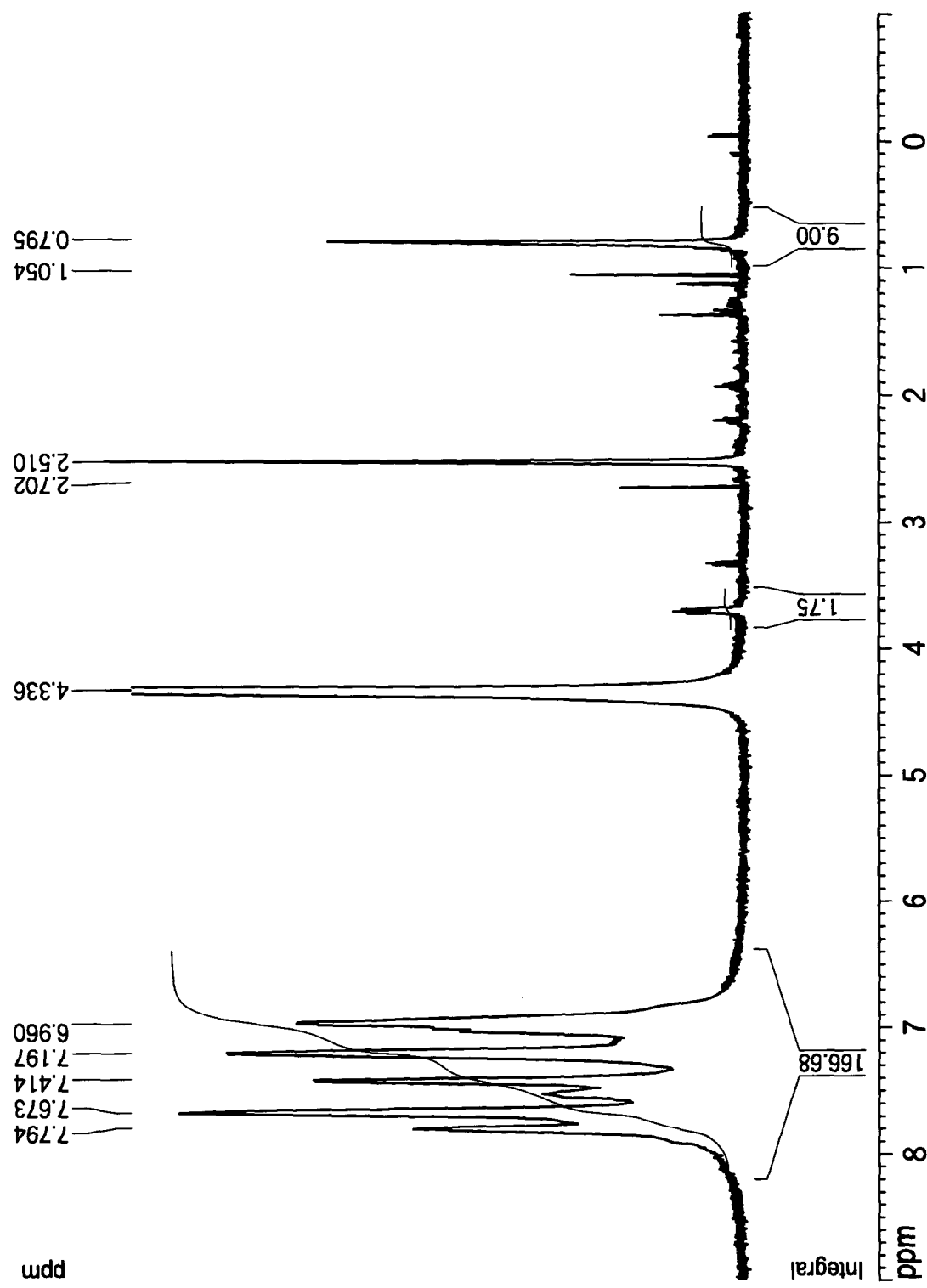
FIG. 22 is an NMR spectrum of polyarylene having a sulfonic acid group prepared in Example 7.

The IR spectrum is shown in FIG. 21 and the NMR spectrum is shown in FIG. 22. The sulfonic acid group-containing polyarylene had a sulfonic acid group content of 2.0 meq/g. (the sulfonic acid group content of the monomer prepared in polymerization was 2.0 meq/g.)

The properties of the resultant film of polyarylene having a sulfonic acid group are shown below.

(1) Proton conductance
  85° C. 95%RH: 0.268 S/cm
  85° C. 70%RH: 0.100 S/cm
  85° C. 30%RH: 0.018 S/cm
(2) Tensile properties
  Room temperature: Modulus of elasticity 4.4 Gpa, Tensile strength 153 Mpa, Yield strength 98 Mpa, Elongation 52%
  120° C.: Modulus of elasticity 4.4 Gpa, Tensile strength 131 Mpa, Elongation 38%

(3) Water content

95° C. 48 hr: 65%

After immersing at 95° C. for 500 hr, the film was stable without change of the sulfonic acid equivalent weight.

(4) Thermal stability

120° C. 500 hr: After heat treatment at 120° C. for 500 hr, insoluble components were not generated and the film was stable without change of the sulfonic acid equivalent weight.

Thermal deformation temperature: 162° C.

Example 8

Conversion of Polyarylene having Neo-pentyl Group as a Protecting Group for Sulfonic Acid (PolyAB—$SO_3$neo-Pe) into Polyarylene having a Sulfonic Acid Group (PolyAB—$SO_3$H)

The procedure of Example 7 was repeated except that instead of PolyAB—$SO_3$neo-Pe used in Example 4, 4.90 g of PolyAB—$SO_3$neo-Pe prepared in Example 5 and 40 mL of trifluoro acetic acid were used and a pale brown powdery polymer was finally obtained.

A 8% by weight NMP solution of the polymer obtained was cast on a glass plate to form a film. After the film formation, the film was air-dried and vacuum-dried to obtain the film having a dried thickness of 40 μm. It was defined from IR spectrum and quantitative analysis of ion exchange capacity that sulfonic acid ester group (—$SO_3$R) was converted to sulfonic acid group (—$SO_3$H).

Figure 23:
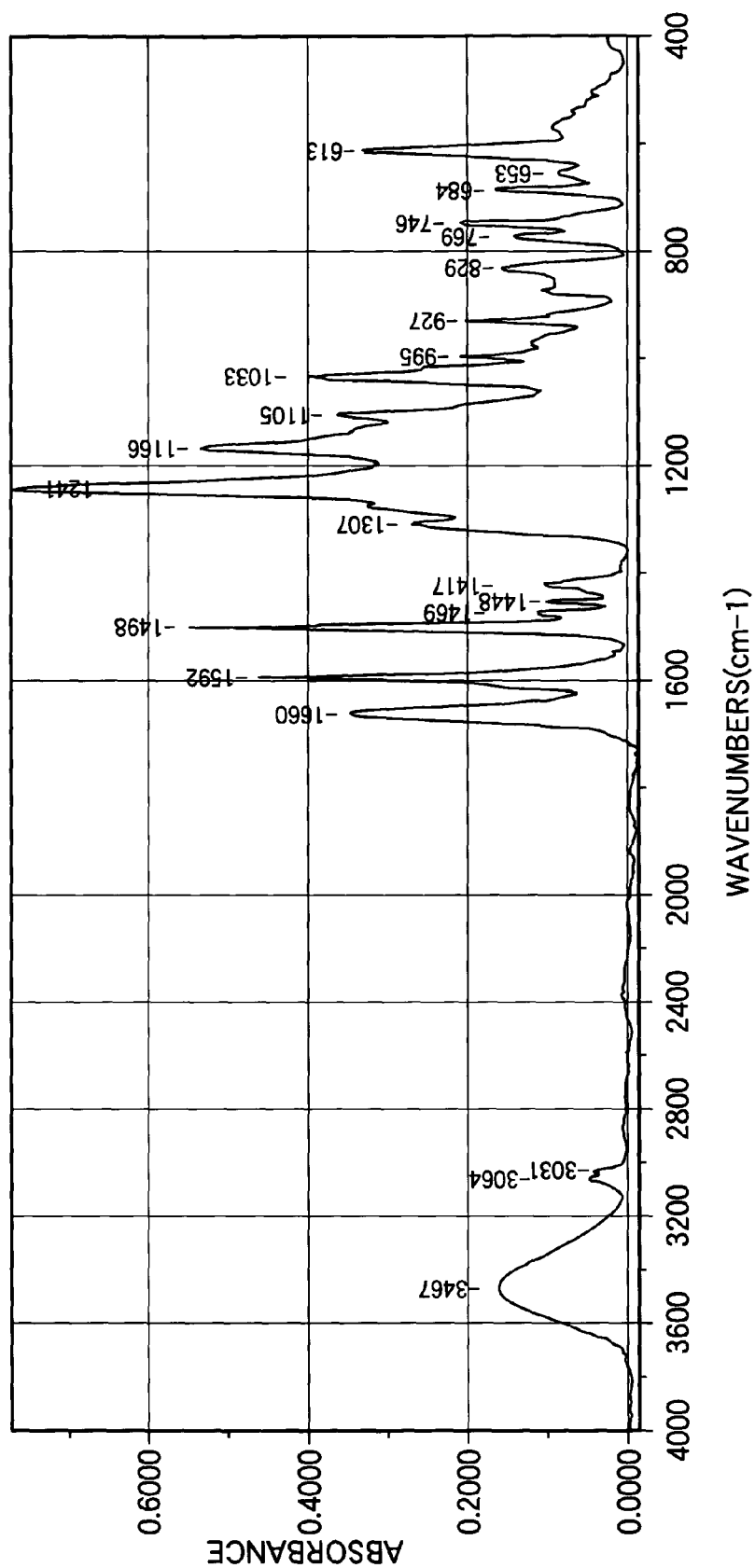
FIG. 23 is an IR spectrum of polyarylene having a sulfonic acid group prepared in Example 8.

The IR spectrum is shown in FIG. 23. The sulfonic acid group-containing polyarylene had a sulfonic acid group content of 1.8 meq/g (the sulfonic acid group content of the monomer prepared in polymerization was 2.2 meq/g).

The properties of the resultant film of polyarylene having a sulfonic acid group are shown below.

(1) Proton conductance

85° C. 95%RH: 0.250 S/cm

85° C. 70%RH: 0.095 S/cm

85° C. 30%RH: 0.018 S/cm (2) Tensile properties

Room temperature: Modulus of elasticity 4.6 Gpa, Tensile strength 136 Mpa, Elongation 44%

120° C.: Modulus of elasticity 4.6 Gpa, Tensile strength 117 Mpa, Elongation 30%

(3) Water content

95° C. 48 hr: 70%

After immersing at 95° C. for 500 hr, the film was stable without change of the sulfonic acid equivalent weight.

(4) Thermal stability

After heat treatment at 120° C. for 500 hr, insoluble components were not generated and the film was stable without change of the sulfonic acid equivalent weight.

Thermal deformation temperature: 170° C.

Example 9

Polymerization of Polyarylene

Dried N,N-dimethylacetoamide (DMAc) in an amount of 100 mL was added to a mixture of 26.66 g (41.7 mmol) of a compound represented by the following formula (3), 17.47 g (1.56 mmol) of BCPAF oligomer prepared in Synthesis Example 1, 0.79 g (1.2 mmol) of Ni($PPh_3$)$_2$$Cl_2$, 4.20 g (16.01 mmol) of $PPh_3$, 0.18 g (1.20 mmol) of NaI and 6.28 g (96.07 mmol) of zinc dust in a nitrogen atmosphere.

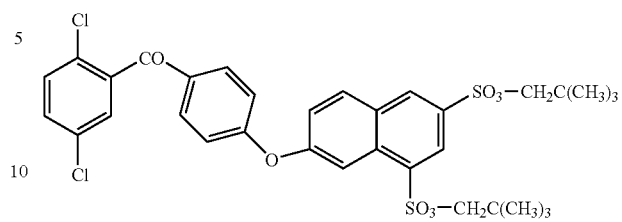

(3)

Figure 24:
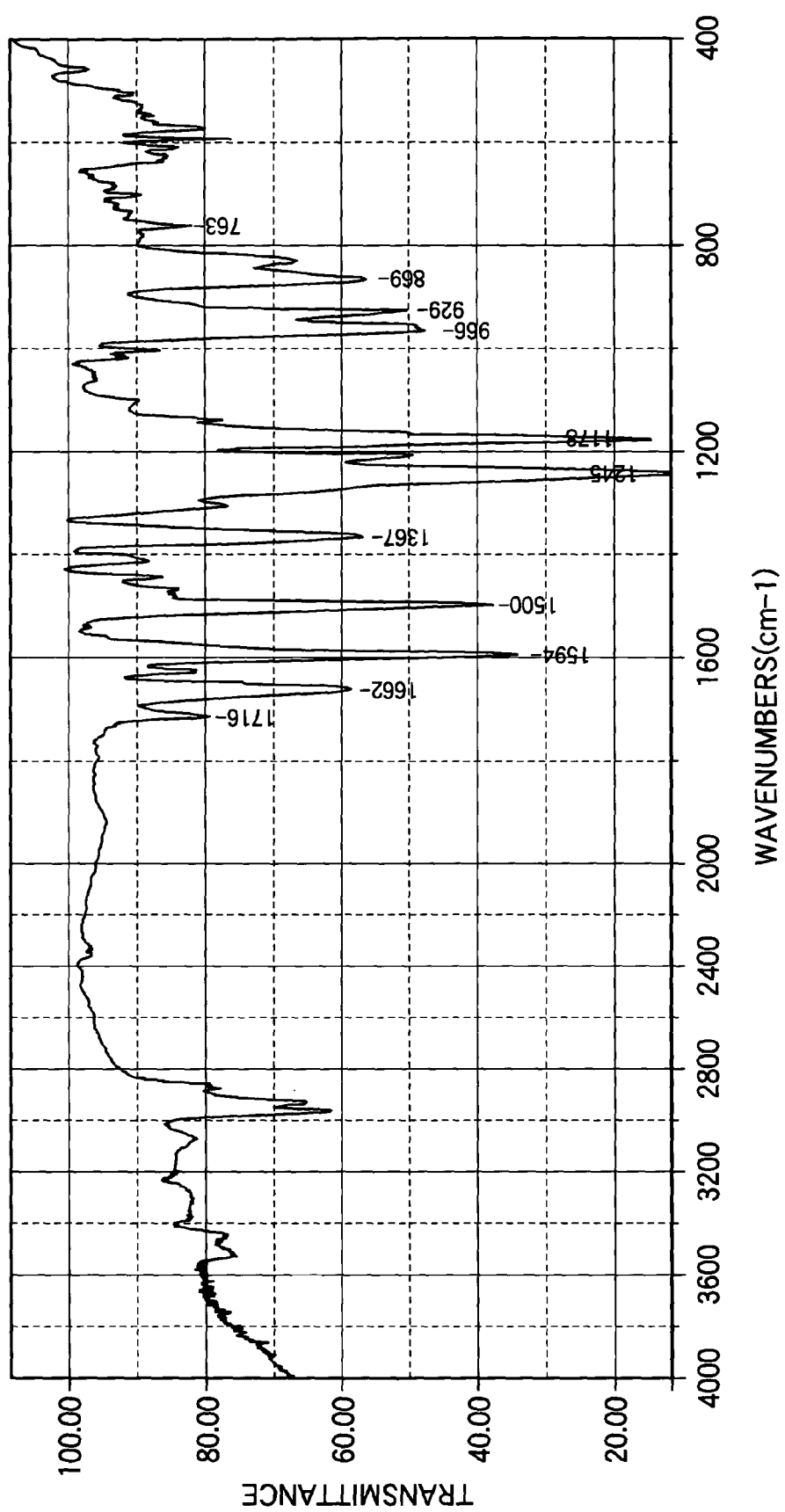
FIG. 24 is an IR spectrum of a copolymer prepared in Example 9.
Figure 25:
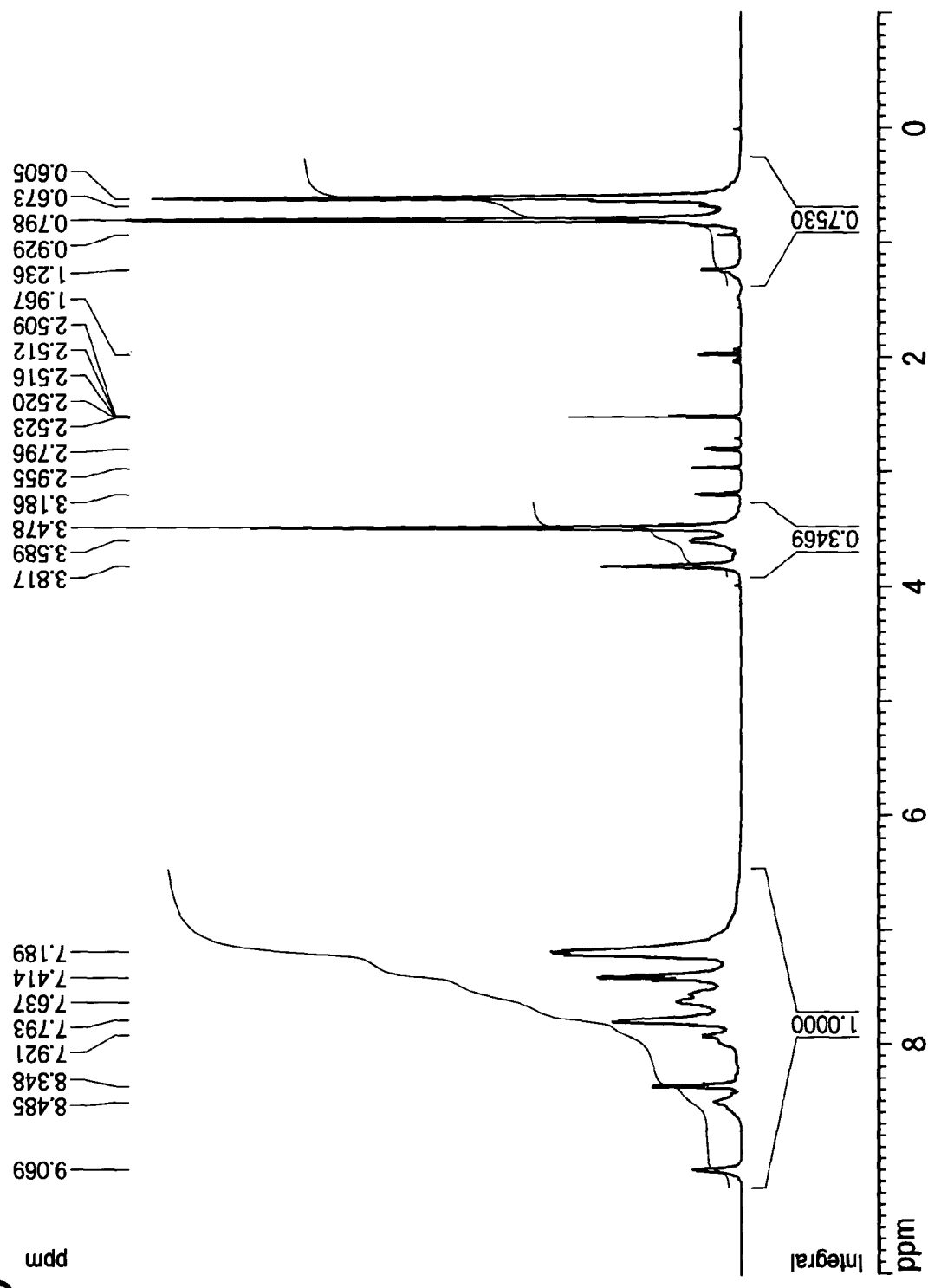
FIG. 25 is an NMR spectrum of a copolymer prepared in Example 9.

The reaction solution was heated with stirring (finally heated to 79° C.), and reacted for 3 hr. During the reaction, the rise of viscosity in the reaction solution was observed. Thereafter, the polymerization reaction solution was diluted with 425 mL of DMAc, stirred for 30 min and filtered using Celite as a filtering assistant. A part of the filtrate was poured into methanol and coagulated. The resultant copolymer of sulfonic acid derivative protected with neo-pentyl group has a number average molecular weight in terms of polystyrene, as determined by GPC(THF solvent), of 59,400 and a weight average molecular weight of 178,300. The IR spectrum of the copolymer is shown in FIG. 24 and the NMR spectrum is shown in FIG. 25.

The above filtrate was concentrated with an evaporator to be in an amount of 344 g and therein 10.00 g (0.12 mol) of LiBr was added and the reaction was carried out at an inner bath temperature of 110° C. (bath temperature 120° C.) in a nitrogen atmosphere for 7 hr. After the reaction, the reaction solution was cooled to room temperature, and poured into 4 L of acetone and coagulated. The resultant coagulum was collected with filtration and air-dried. Thereafter the coagulum was pulverized by a mixer and washed by 1500 mL of 1N hydrochloric acid with stirring. After filtration, the resultant product was washed with ion-exchanged water so as to have a pH of 5 or more, and a powdery polymer was finally obtained.

A 8% by weight NMP solution of the polymer obtained was cast on a glass plate to form a film. After the film formation, the film was air-dried and vacuum-dried to obtain the film having a dried thickness of 40 μm. It was defined from IR spectrum and quantitative analysis of ion exchange capacity that sulfonic acid ester group was quantitatively converted to sulfonic acid group.

Figure 26:
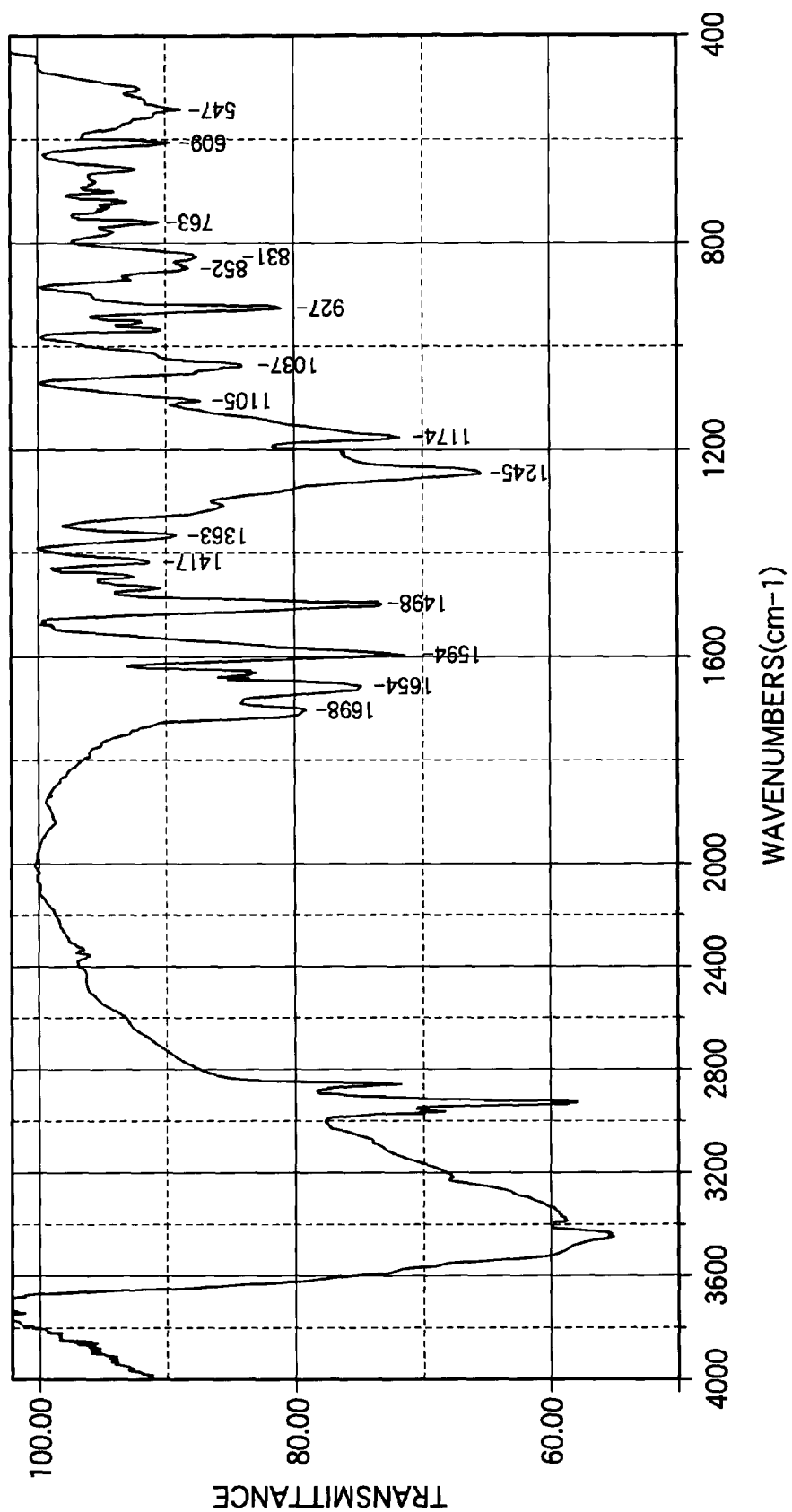
FIG. 26 is an IR spectrum of polyarylene having a sulfonic acid group prepared in Example 9.
Figure 27:
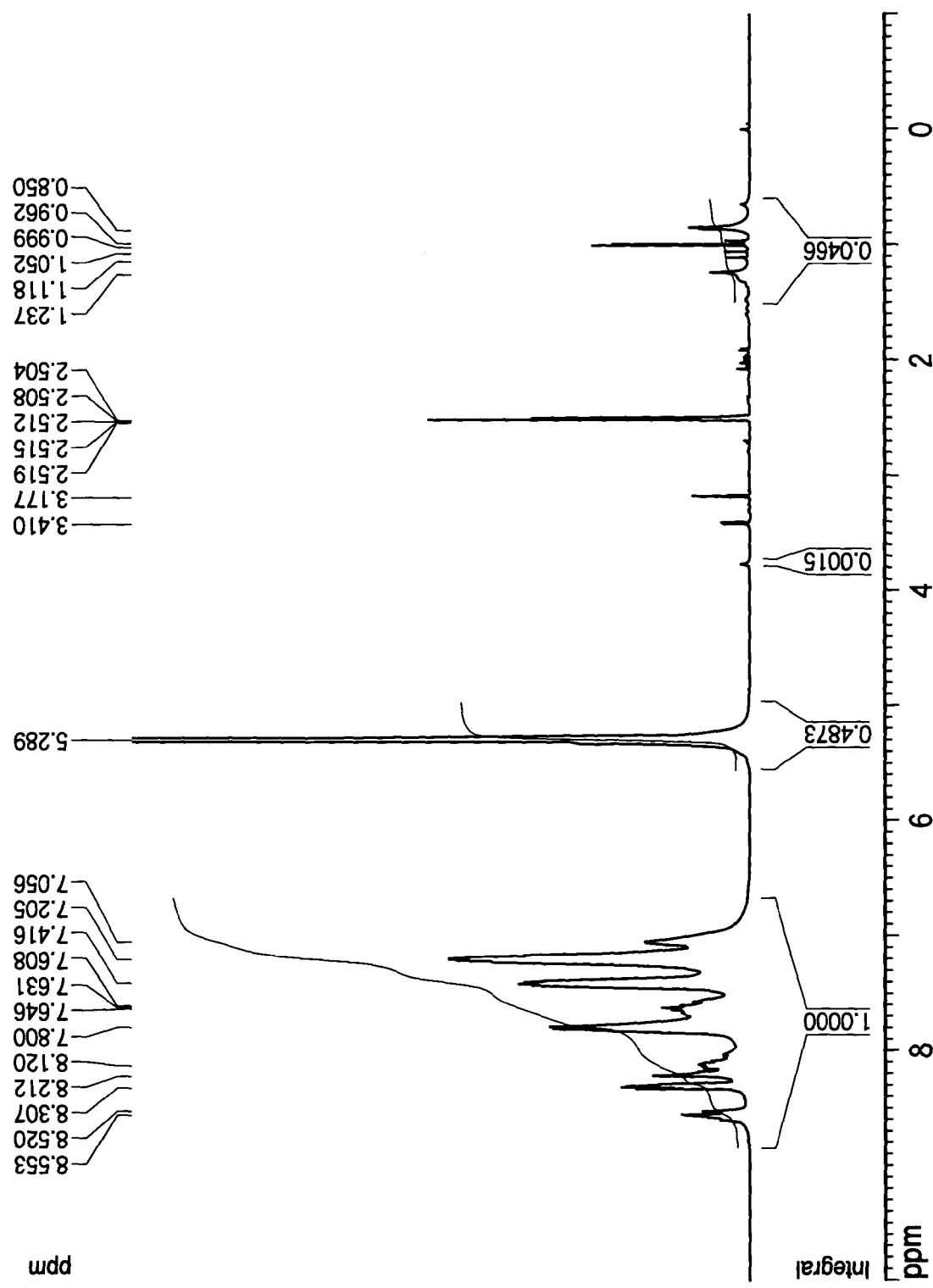
FIG. 27 is an NMR spectrum of polyarylene having a sulfonic acid group prepared in Example 9.

The sulfonic acid group-containing polyarylene had a sulfonic acid group content of 2.0 meq/g (theoretical value of a sulfonic acid group content determined from the molar ratio of the monomer prepared in polymerization was 2.0 meq/g). The IR spectrum of the resultant sulfonic acid group-containing polyarylene is shown in FIG. 26, and the NMR spectrum is shown in FIG. 27.

The properties of the resultant film of polyarylene having a sulfonic acid group are shown below.

(1) Proton conductance

85° C. 95%RH: 0.275 S/cm

85° C. 70%RH: 0.106 S/cm

85° C. 30%RH: 0.022 S/cm (2) Thermal stability

After heat treatment at 120° C. for 500 hr, generation of insoluble components was not observed and the film was stable without change of the sulfonic acid equivalent weight.

Example 10

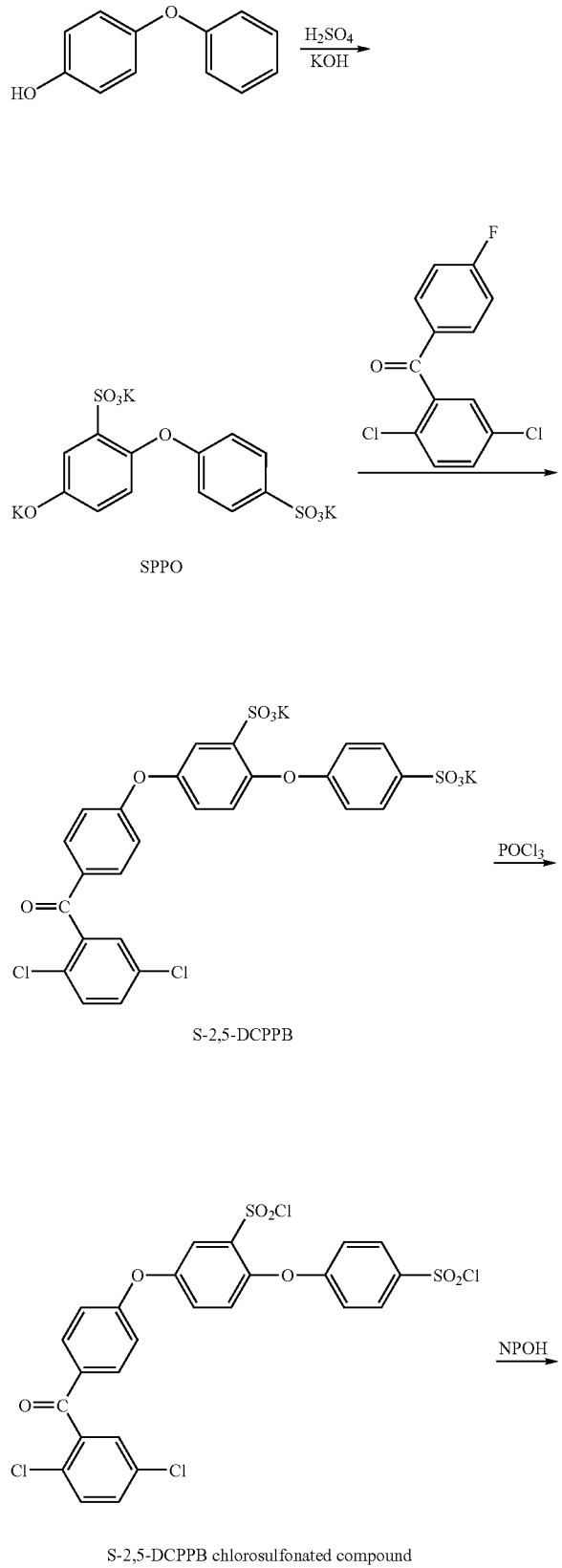

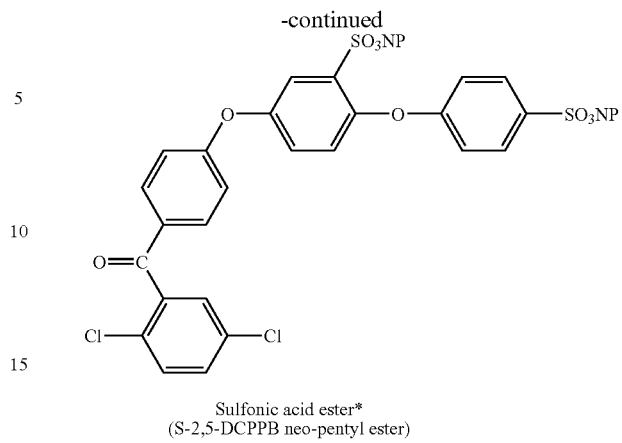

Sulfonic acid ester*
(S-2,5-DCPPB neo-pentyl ester)

In the above formula, Np is a neo-pentyl group.

(1) Synthesis of Disulfonated Compound of Phenoxy Phenol (SPPO)

Figure 28:
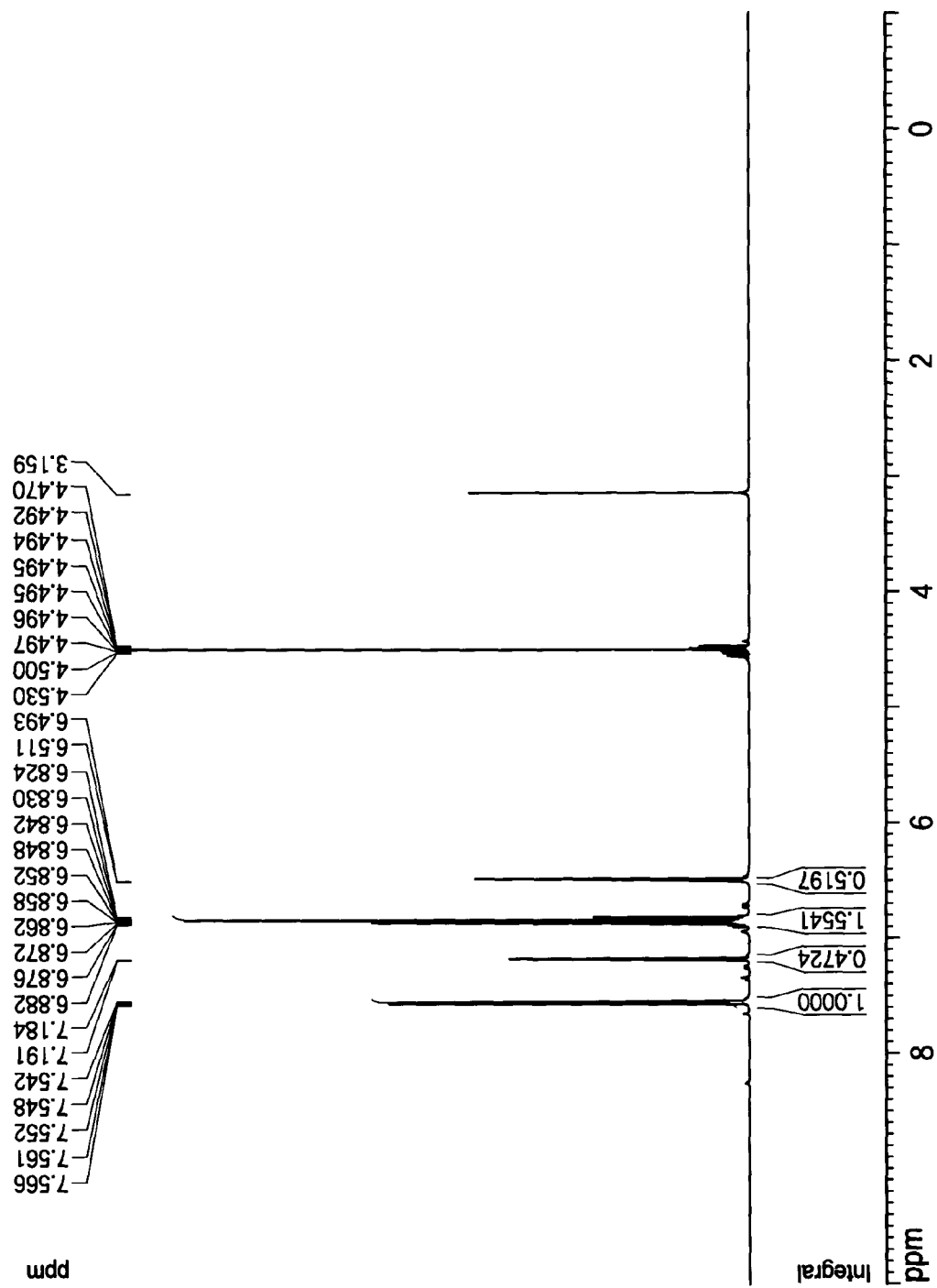
FIG. 28 is an NMR spectrum of a phenoxyphenol disulfonated compound prepared in Example 10.

To a 1 L three-necked flask equipped with a stirring blade, a thermometer and a nitrogen introducing tube, 370 g (0.69 mol) of 4-phenoxyphenol was introduced and 740 mL of concentrated sulfuric acid was added dropwise over about 1 hr. After completion of the dropping, the solution was stirred at 50° C. for 3 hr. After completion of the reaction, the reaction solution was diluted with 200 mL of water and neutralized with a KOH solution (KOH 1.5 Kg/water 750 mL). The thus precipitated solid was filtered and washed with acetone to obtain 1709 g of a white powder. The powder contained potassium salt of phenoxyphenol disulfonated compound (SPPO) and potassium hydroxide. The NMR spectrum of the powder is shown in FIG. 28.

(2) Synthesis of 2,5-dichloro-4'-(4-phenoxyphenoxy)benzophenone Disulfonated Compound (S-2,5-DCPPB)

Figure 29:
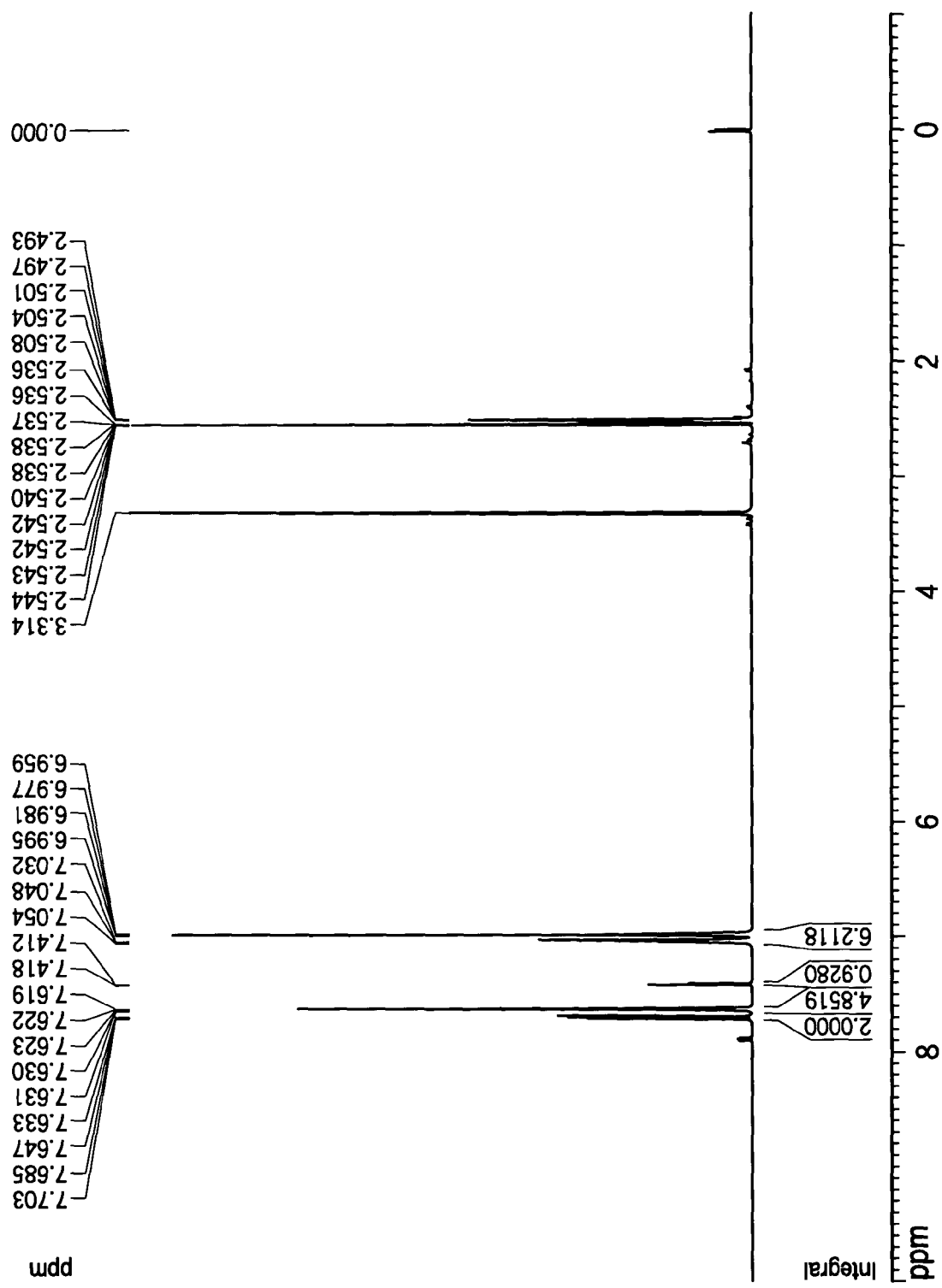
FIG. 29 is an NMR spectrum of a 2,5-dichloro-4'-(4-phenoxyphenoxy)benzophenone disulfonated compound prepared in Example 10.

To a 1 L three-necked flask equipped with a stirring blade, a thermometer and a nitrogen-introducing tube, 43.7 g (0.31 mol) of SPPO, 43.14 g (0.10 mol) of 2,5-dichloro-4'-fluorobenzophenone, 2.6 g (8 mmol) of tetra-n-butylammonium bromide (TBAB) and 200 mL of dimethylsulfoxide were introduced and stirred in a nitrogen atmosphere at 160° C. Further, 30 g (65 mmol) of SPPO and 1.0 g (3 mmol) of TBAB were properly added and the reaction was continued. After 30 hr, the resultant salt was filtered and a filtrate was poured into 4.5 L of acetone. The thus deposited solid was filtered and washed with 1 to 1.5 L of acetone four to five times. The solid was vacuum-dried to obtain 81 g of S-2,5-DCPPB (yield 70%). The NMR spectrum of the compound is shown in FIG. 29.

(3) Synthesis of S-2,5-DCPPB Chlorosulfonylated Compound

Figure 30:
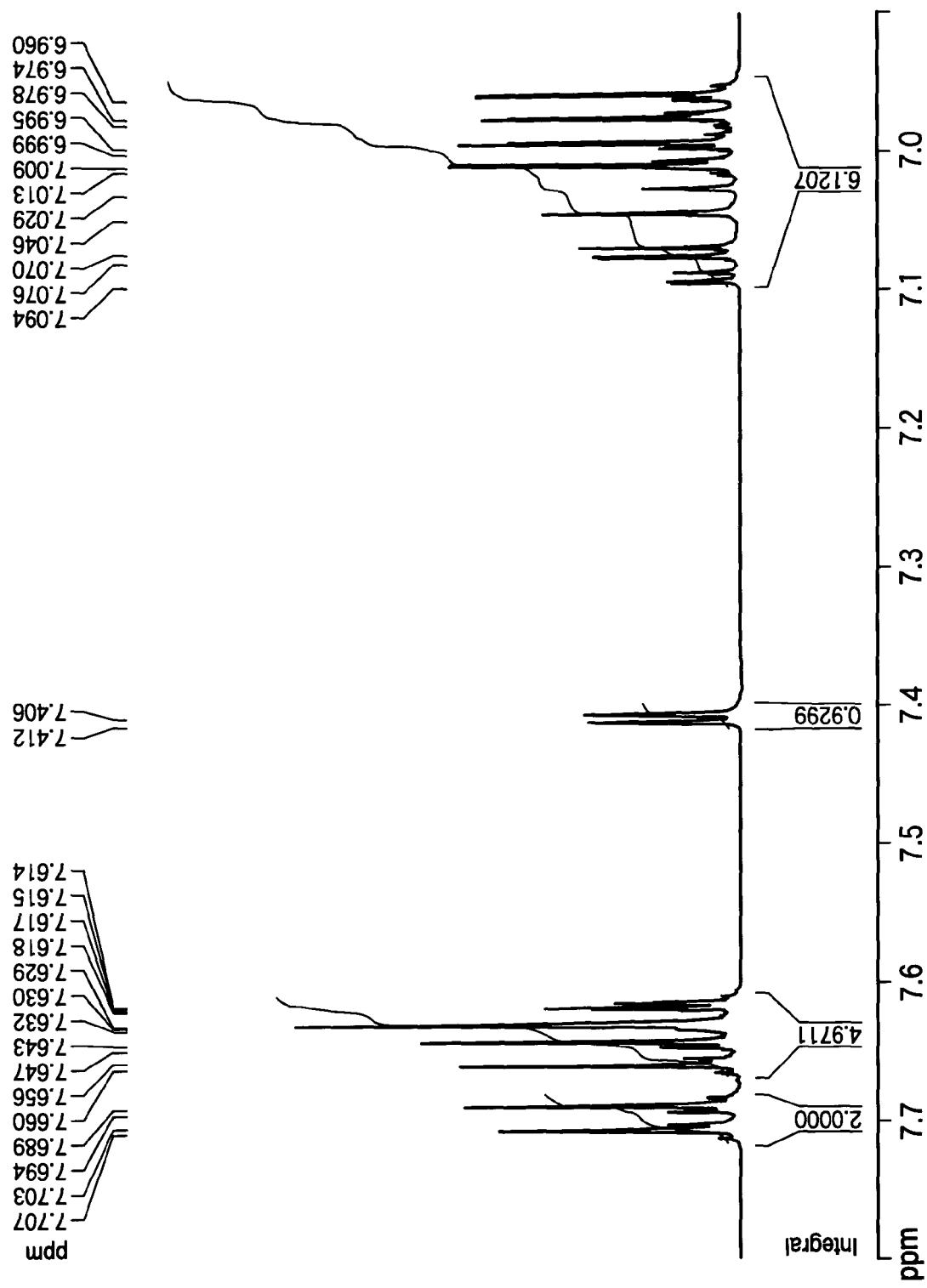
FIG. 30 is an NMR spectrum of a S-2,5-DCPPB chlorosulfonylated compound prepared in Example 10.

To a 1 L three-necked flask equipped with a stirring blade, a thermometer and a nitrogen-introducing tube, 146.5 g (0.22 mol) of S-2,5-DCPPB and 650 mL of acetonitrile were introduced and stirred at 70°. To the solution, 220 g of phosphoryl chloride was added dropwise over 15 min and then stirred for 5 hr. After completion of the reaction, 1.3 Kg of ice water was added dropwise to the reaction solution and diluted with 2.5 L of toluene. The organic phase was dried with anhydrous magnesium sulfate. After the remained inorganic salt was removed with a silica gel column chromatography (development solvent: toluene), the residue was re-crystallized with toluene/hexane to obtain 71 g of the aimed compound (yield: 52%). The NMR spectrum of the compound is shown in FIG. 30.

(4) Synthesis of S-2,5-DCPPB Neo-pentyl Ester

Figure 31:
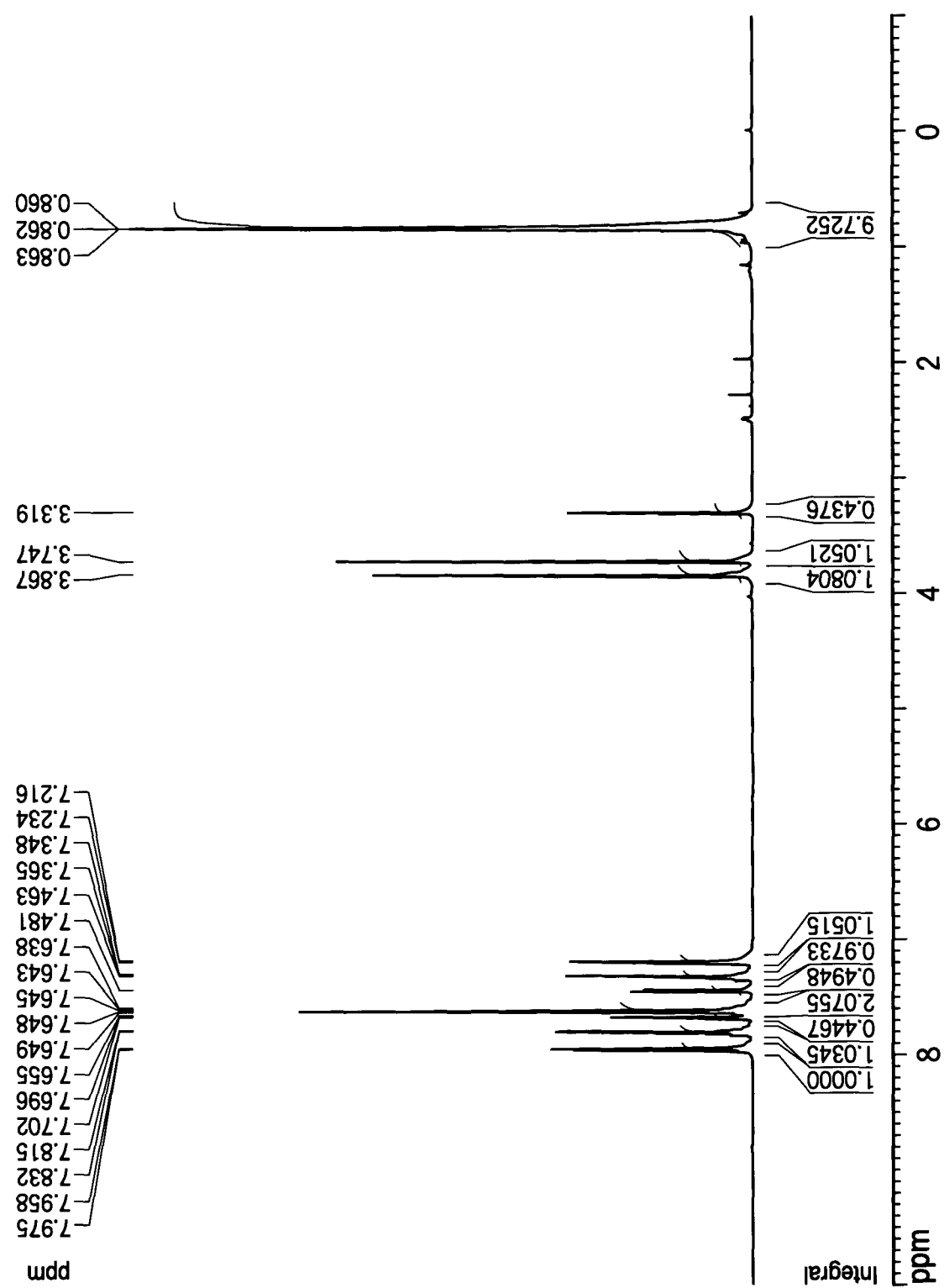
FIG. 31 is an IR spectrum of S-2,5-DCPPB neo-pentyl ester prepared in Example 10.
Figure 32:
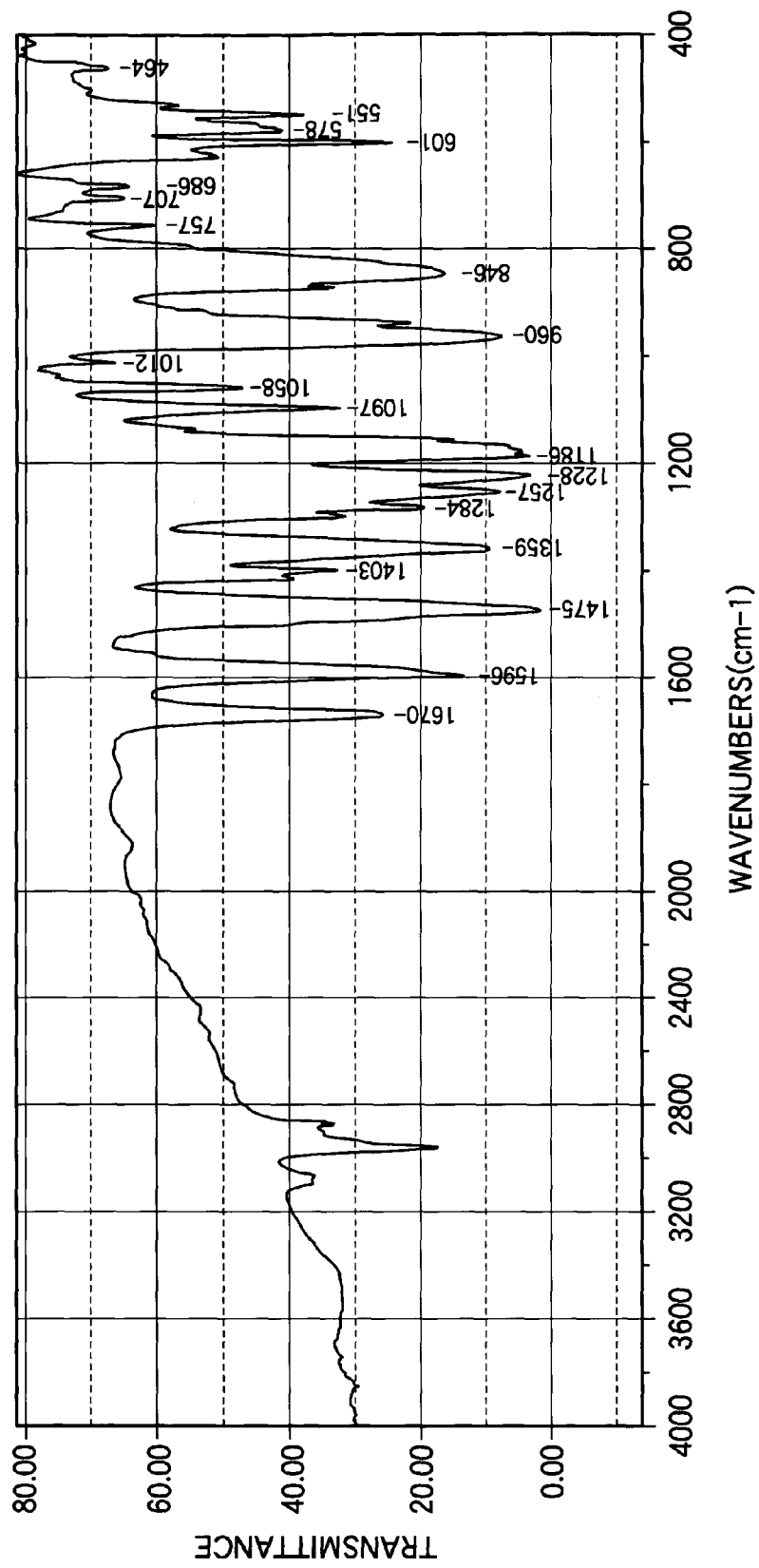
FIG. 32 is an NMR spectrum of S-2,5-DCPPB neo-pentyl ester prepared in Example 10.

To a 1 L three-necked flask equipped with a stirring blade, a thermometer and a nitrogen-introducing tube, 59.5 g (94 mol) of S-2,5-DCPPB chlorosulfonylated compound and 400 mL of pyridine were introduced and cooled in an ice bath. To the solution, 20.5 g (233 mmol) of neo-pentyl alchol was added and stirred. Thereafter, the ice bath was taken off and the solution was stirred at room temperature for 5 hr. The thus precipitated pyridine salt was removed with filtration, and the residue was extracted with toluene/ethyl acetate (600 mL/600 mL). The extracted solution was washed with a hydrochloric aqueous solution (concentrated hydrochloric acid 300 mL/water 300 mL) several times and then washed with a 5% hydrogencarbonate sodium aqueous solution and saturated sodium chloride water several times. The solvent was distilled off, and 36 g of S-2,5-DCPPB neo-pentyl ester was obtained by separation with silica gel chromatography (development solvent: toluene). The IR spectrum of the ester is shown in FIG. 31 and the NMR is shown in FIG. 32.

Example 11

Synthesis of Polyarylene

In a 500 mL three-necked flask equipped with a stirring blade, a thermometer and a nitrogen-introducing tube, 21.4 g (29 mmol) of 2,5-DCPB neo-pentyl ester prepared in Example 10, 9.90 g (0.9 mmol) of BCPAF oligomer prepared in Synthesis Example 1, 0.59 g (0.9 mmol) of bis (triphenyl phosphine) nickel dichloride, 0.13 g(0.9 mmol) of sodium iodide, 3.15 g(12 mmol) of triphenylphosphine and 4.71 g(72 mmol) of zinc were weighed and vacuum dried for 2 hr. Thereafter, the flask was purged with dried nitrogen and 73 mL of dehydrated dimethyl acetoamide was added to the flask, and then polymerization was started.

The polymerization was continued for 3 hr while the reaction temperature was regulated to be not higher 90° C. Subsequently, the polymerization solution was diluted by adding 80 mL of tetrahydrofuran and then poured into a methanol/concentrated hydrochloric acid solution (methanol 2.7 L/concentrated hydrochloric acid 0.3 L).

The thus precipitated product was filtered, washed with methanol and then air-dried. The dried polymer was dissolved in tetrahydrofuran and insoluble components were removed with filtration and thereafter the remainder was re-precipitated in 3.5 L of methanol. A polymer was filtered and vacuum dried to obtain 23.5 g of polyarylene (yield 80%). The resultant polymer had a number average molecular weight in terms of polystyrene, as determined by GPC (THF solvent), of 61,000 and a weight average molecular weight of 278,000.

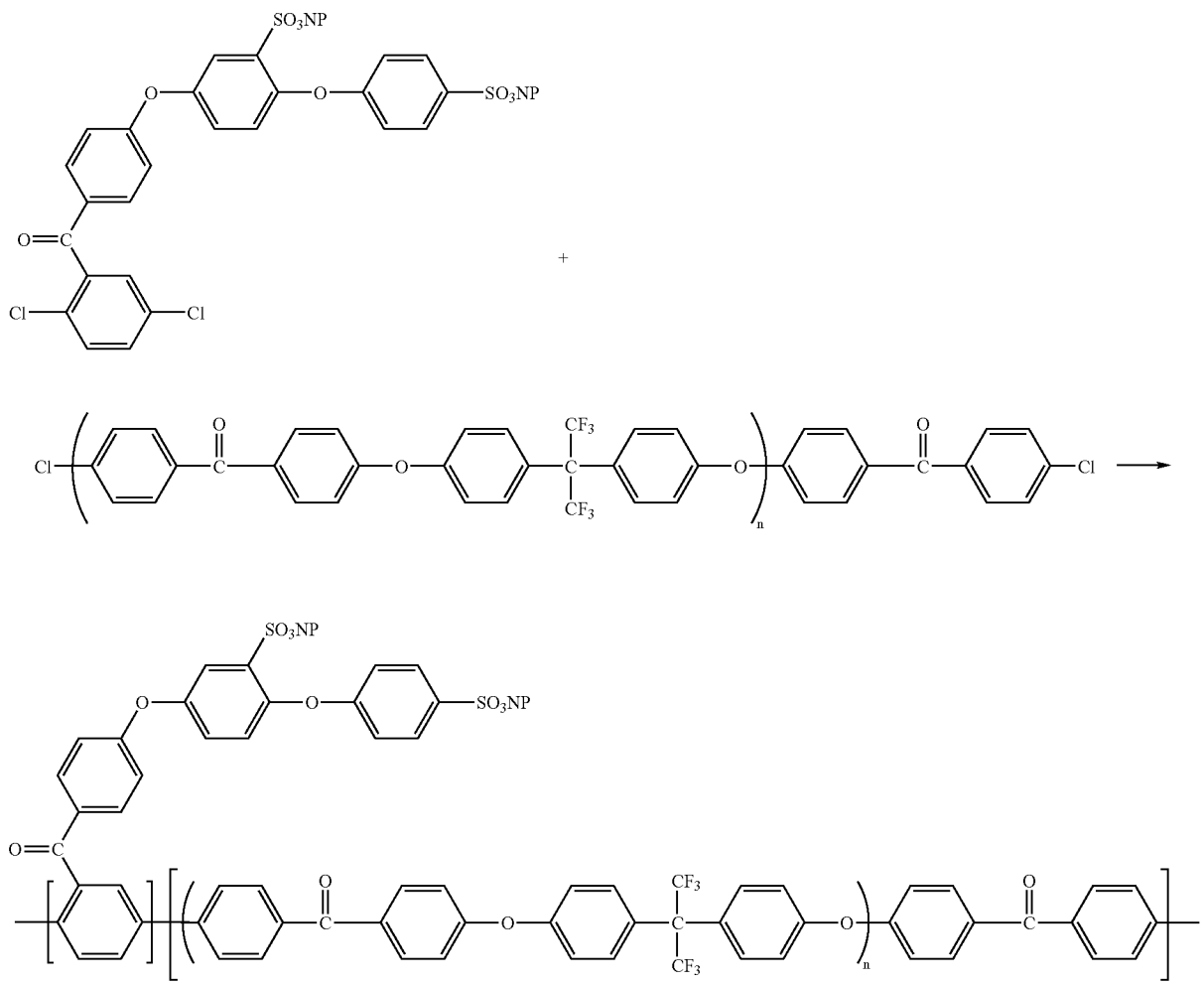

In the formula, NP is a neo-pentyl group.

Example 12

Synthesis of Polyarylene Having a Sulfonic Acid

To a 300 mL three-necked flask equipped with a stirring blade, a thermometer and a nitrogen-introducing tube, 23.5 g of polyarylene prepared in Example 11, 6.34 g (73 mmol) of lithium bromide were introduced and stirred at 120° C. for 7 hr. The resulting reaction solution was poured into acetone to coagulate a polymer. The resultant solid polymer was treated with a distilled water/concentrated hydrochloric acid solution (3.0 L/0.37 L) twice and then washed with distilled water until the pH was neutralized. The solid polymer was dried at 70° C. for 12 hr to obtain 19.9 g of polyarylene having a sulfonic acid group represented by the following formula.

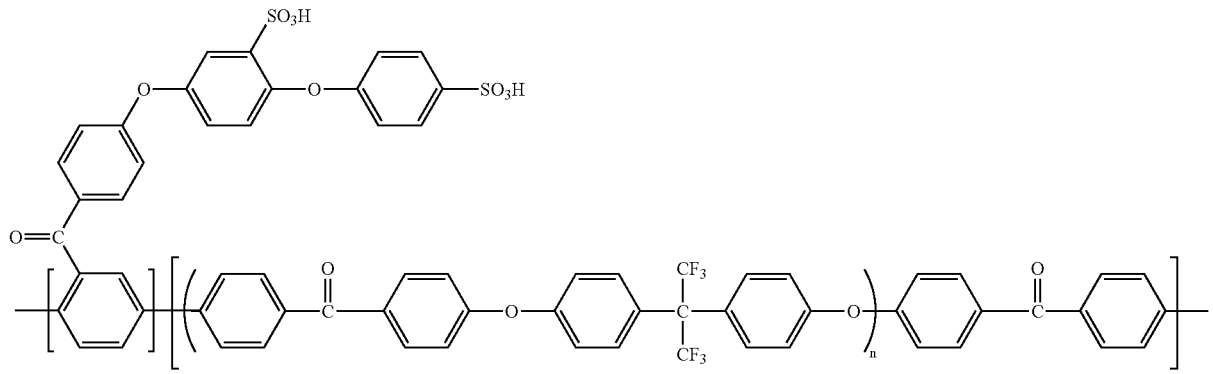

The resultant polymer had a number average molecular weight in terms of polystyrene, as determined by GPC (THF solvent), of 78,000 and a weight average molecular weight of 230,000. The polyarylene having a sulfonic acid group had an ion exchange capacity of 2.19 meq/g. Using a N-methyl pyrrolidone solution, a film having a thickness of 40 μm was prepared by a cast method.

Evaluation on Properties

With regard to the resulting film, the properties were evaluated. The results are summarized in Table 1.

TABLE 1

| Evaluation items | Unit | |
|---|---|---|
| Proton conductance (85° C., 90% RH) | S/cm | 0.25 |
| Modulus of elasticity | Gpa | 3.5 |
| Breaking strength | Mpa | 84 |
| Elongation | % | 46 |
| Resistance to hot water (120° C., 100 hr) | Weight retention rate, % | 100 |
| Resistance to Fenton reagent (3% $H_2O_2$, 20 ppm $Fe^{2+}$, 45° C., 20 hr) | Weight retention rate, % | 100 |
| Thermal decomposition starting temperature | ° C. | 240 |

EFFECT OF THE INVENTION

The polyarylene having a sulfonic acid group according to the present invention and the process for producing the same have high safety and a low load in recovering a polymer because in converting polyarylene into polyarylene having a sulfonic acid group, a sulfonating agent is not used. Further, the amount of sulfonic acid group introduced into a polymer and the introducing position thereof are easily controlled.

The aromatic sulfonic acid ester derivative and polyarylene according to the present invention are used for the above-described polyarylene having a sulfonic acid and the process for producing the same.

The proton conductive membrane of the present invention has excellent proton conductance.

The invention claimed is:

1. An aromatic sulfonic acid ester derivative represented by the formula (1);

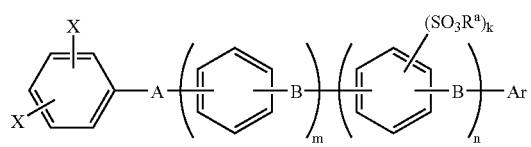

(1)

in which X is an atom or a group selected from a halogen atom excluding fluorine, —$OSO_3CH_3$ and —$OSO_3CF_3$, A is a divalent electron attractive group, B is a divalent electron donating group or a direct bonding, $R^a$ is a hydrocarbon group of 1 to 20 carbon atoms, Ar is an aromatic group having a substituent represented by —$SO_3R^b$ (wherein $R^b$ is a hydrocarbon group of 1 to 20 carbon atoms), m is an integer of 0 to 10, n is an integer of 0 to 10 and k is an integer of 1 to 4.

2. An aromatic sulfonic acid ester derivative according to claim 1 wherein the aromatic group in the aromatic group having a substituent represented by —$SO_3R^b$ is a group selected from phenyl group, naphthyl group, anthracenyl group and phenanethyl group.

3. An aromatic sulfonic acid ester derivative according to claim 1 wherein $R^a$ and $R^b$ is a group of 4 to 20 carbon atoms selected from a linear hydrocarbon group, a branched hydrocarbon group, an alicyclic hydrocarbon group and a hydrocarbon group having a 5-membered hetero ring.

4. An aromatic sulfonic acid ester derivative according to claim 1 wherein the divalent electron attractive group is selected from —CO—, —CONH—, —$(CF_2)_p$— (wherein p is an integer of 1 to 10), —C(CF₃)₂—, —COO—, —SO— and —SO₂—, and the divalent electron donating group is a group selected from —O—, —S—, —CH=CH—, —C≡C—,

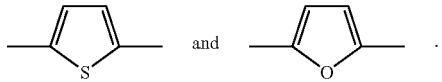

.

5. A polyarylene comprising repeating structural units derived from an aromatic compound, which contains at least repeating structural units represented by the formula (1');

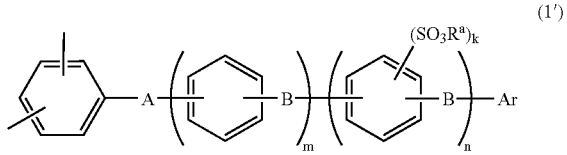

(1')

in which A is a divalent electron attractive group, B is a divalent electron donating group or a direct bonding, $R^a$ is a hydrocarbon group of 1 to 20 carbon atoms, Ar is an aromatic group having a substituent represented by —SO³$R^b$ (wherein $R^b$ is a hydrocarbon group of 1 to 20 carbon atoms), m is an integer of 0 to 10, n is an integer of 0 to 10 and k is an integer of 1 to 4.

6. A polyarylene according to claim 5 comprising 0.5 to 100% by mole of repeating structural units represented by the formula (1') and 0 to 99.5% by mole of repeating structural units represented by the following formula (A');

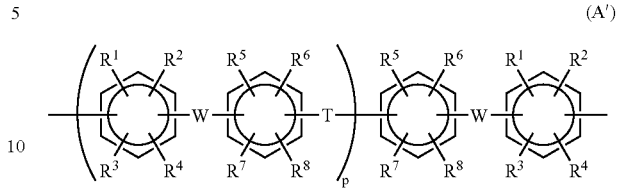

(A')

in which $R^1$ to $R^8$ is identically or differently at least one atom or group selected from hydrogen, fluorine atom, alkyl group, fluorine substituted alkyl group, allyl group and aryl group, W is a divalent electron attractive group, T is a divalent organic group and p is 0 or a positive integer.

7. A process for producing a polyarylene having a sulfonic acid group which process comprises the steps of coupling polymerizing an aromatic compound containing an aromatic sulfonic acid ester derivative as claimed in claim 1 to prepare a polyarylene, and hydrolyzing the resulting polyarylene.

8. A polymer solid electrolyte comprising a polyarylene having a sulfonic acid group prepared by a process as claimed in claim 7.

9. A proton-conductive membrane for fuel cells which membrane comprises a polymer solid electrolyte as claimed in claim 8.

* * * * *